United States Patent
Farrow et al.

(10) Patent No.: US 12,220,533 B2
(45) Date of Patent: Feb. 11, 2025

(54) INTERFACE ASSEMBLIES FOR RESPIRATORY THERAPY

(71) Applicant: Fisher & Paykel Healthcare Limited, Auckland (NZ)

(72) Inventors: Abby Rebecca Farrow, Auckland (NZ); Peter David Alexander Bearne, Auckland (NZ); Dana Willfroth, Auckland (NZ); Jae Yun Lim, Auckland (NZ); Matthew James Pedersen, Auckland (NZ); Roheet Patel, Auckland (NZ); Birgit Wuestenhagen, Auckland (NZ); Paul Mathew Freestone, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1044 days.

(21) Appl. No.: 15/734,541

(22) PCT Filed: Jun. 4, 2019

(86) PCT No.: PCT/NZ2019/050063
§ 371 (c)(1),
(2) Date: Dec. 2, 2020

(87) PCT Pub. No.: WO2019/235939
PCT Pub. Date: Dec. 12, 2019

(65) Prior Publication Data
US 2021/0228830 A1    Jul. 29, 2021

Related U.S. Application Data

(60) Provisional application No. 62/680,333, filed on Jun. 4, 2018.

(51) Int. Cl.
*A61M 16/06*    (2006.01)
*A61M 16/08*    (2006.01)
(Continued)

(52) U.S. Cl.
CPC .... *A61M 16/0683* (2013.01); *A61M 16/0622* (2014.02); *A61M 16/0816* (2013.01);
(Continued)

(58) Field of Classification Search
CPC .............. A61M 16/00; A61M 16/0605; A61M 16/0622; A61M 16/0683; A61M 2205/0216
See application file for complete search history.

(56) References Cited

U.S. PATENT DOCUMENTS 6,561,190 B1    5/2003 Kwok
2006/0042629 A1   3/2006 Geist
(Continued)

FOREIGN PATENT DOCUMENTS

CA    3037853 A1    4/2018
EP    1163923       11/2005
(Continued)

OTHER PUBLICATIONS

Patent Cooperation Treaty, International Search Report, Application No. PCT/NZ2019/050063, dated Sep. 9, 2019, in 18 pages.

*Primary Examiner* — Kendra D Carter
*Assistant Examiner* — Maap Ahmed Ellabib
(74) *Attorney, Agent, or Firm* — VIA LLP

(57) ABSTRACT

In some embodiments there is provided a headgear assembly for a full-face under-nose respiratory mask comprising a strap assembly including a rear panel, a crown strap, a pair of opposing upper side straps, and a pair of opposing lower side straps. The assembly further comprises a flexible headgear connector element, wherein a free end of each of the upper straps is coupled to the headgear connector element, and wherein the headgear connector element is configured to extend laterally across and be removably fastened to a frame of the respiratory mask below a tip of a user's nose.

(Continued)

There is also provided a respiratory mask assembly comprising a mask frame and a cushion module, the mask frame comprising a breathing gas inlet configured to receive a supply of breathable gas and to deliver the breathable gas to the cushion module, the cushion module being configured to form a seal with a user's face. The mask assembly can further comprise a bias vent in communication with the cushion module, and configured to allow air to be exhausted from the cushion module through the bias vent. the bias vent can be provided with a diffuser comprising diffuser material configured to extend over the bias vent, the diffuser material providing a tortuous air path from the bias vent through the diffuser. Embodiments are disclosed in which the bias vent and/or diffuser are provided on various components of the assembly.

15 Claims, 64 Drawing Sheets

(51) Int. Cl.
    *A61M 16/10*        (2006.01)
    *A61M 16/20*        (2006.01)

(52) U.S. Cl.
    CPC ....... *A61M 16/1095* (2014.02); *A61M 16/208* (2013.01); *A61M 2205/0216* (2013.01); *A61M 2205/42* (2013.01)

(56) References Cited

U.S. PATENT DOCUMENTS

| | | |
|---|---|---|
| 2009/0050156 A1 | 2/2009 | Ng et al. |
| 2010/0051034 A1 | 3/2010 | Howard et al. |
| 2016/0184544 A1* | 6/2016 | Patel ................ A61M 16/0683 128/206.24 |
| 2016/0271351 A1 | 9/2016 | Frater et al. |
| 2016/0367778 A1 | 12/2016 | Eves et al. |
| 2017/0065786 A1 | 3/2017 | Stephenson et al. |
| 2017/0304577 A1 | 10/2017 | Bearne et al. |
| 2018/0236198 A1 | 8/2018 | Veliss et al. |

FOREIGN PATENT DOCUMENTS

| | | | | |
|---|---|---|---|---|
| EP | 2954920 | 9/2017 | | |
| WO | WO 2005/018523 | 3/2005 | | |
| WO | WO 2007/012140 | 2/2007 | | |
| WO | WO 2007/053878 | 5/2007 | | |
| WO | WO 2008/017100 | 2/2008 | | |
| WO | WO 2011/077254 | 6/2011 | | |
| WO | WO 2012/040791 | 4/2012 | | |
| WO | WO-2012040791 A1 * | 4/2012 | ........ | A61M 16/0057 |
| WO | WO 2014/183167 A1 | 11/2014 | | |
| WO | WO-2015193821 A1 * | 12/2015 | ............ | A61M 16/06 |
| WO | WO 2017/158747 | 9/2017 | | |
| WO | WO 2017/216708 | 12/2017 | | |
| WO | WO 2017/216708 A1 | 12/2017 | | |

\* cited by examiner

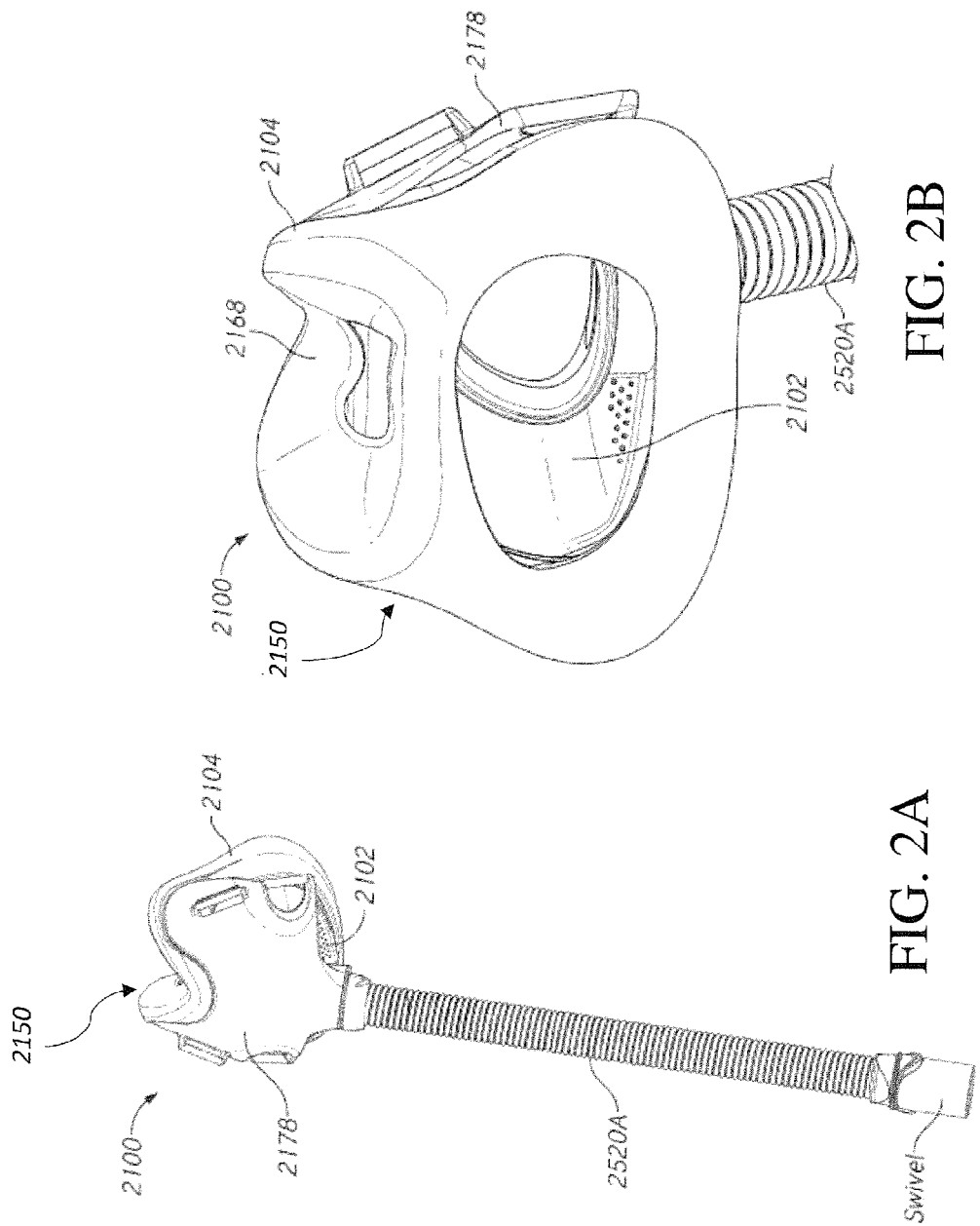

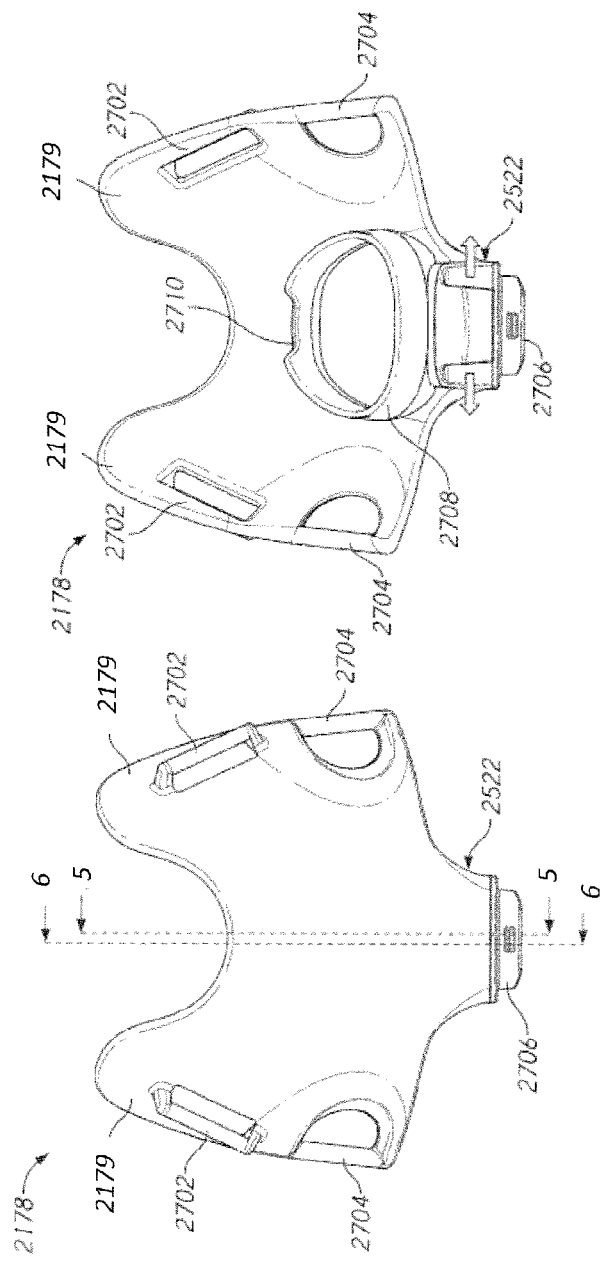

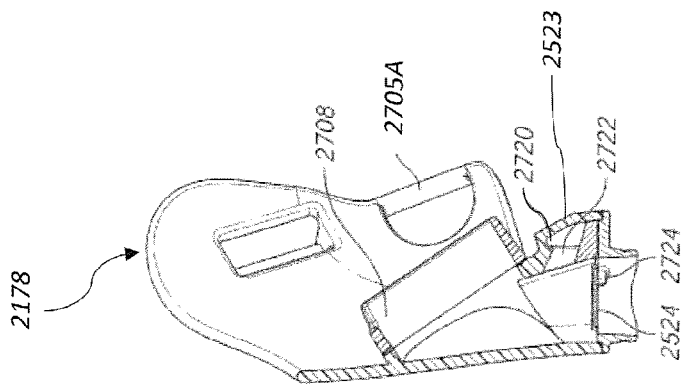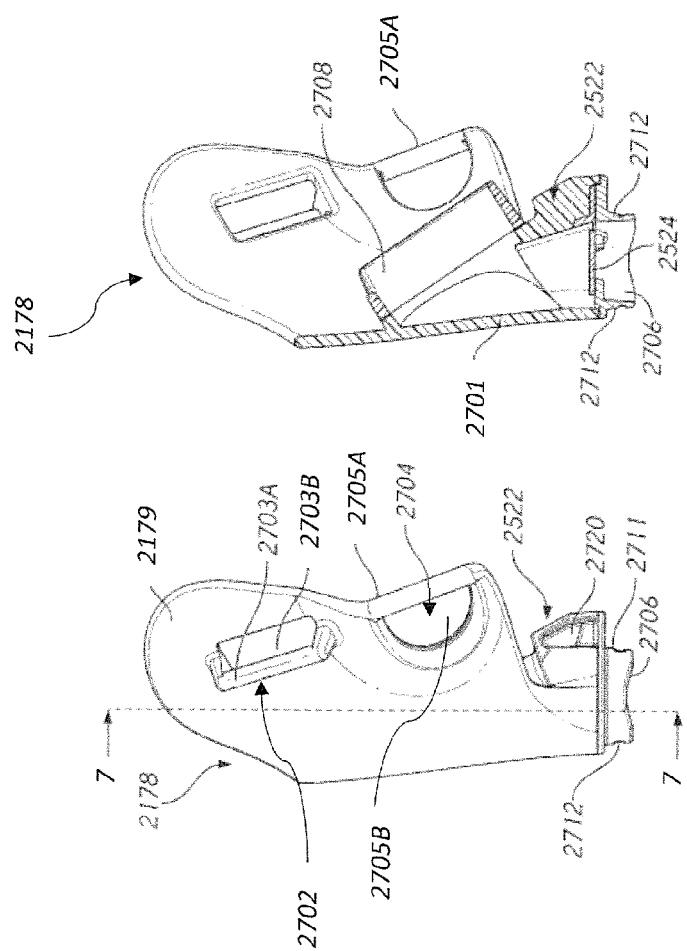

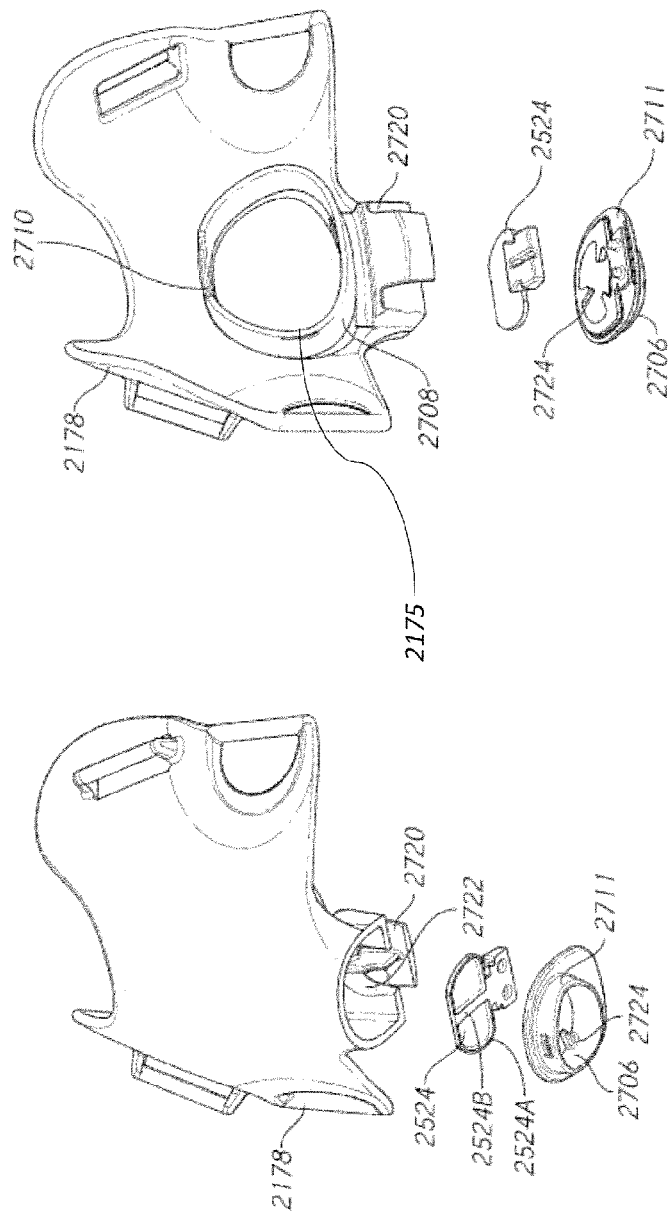

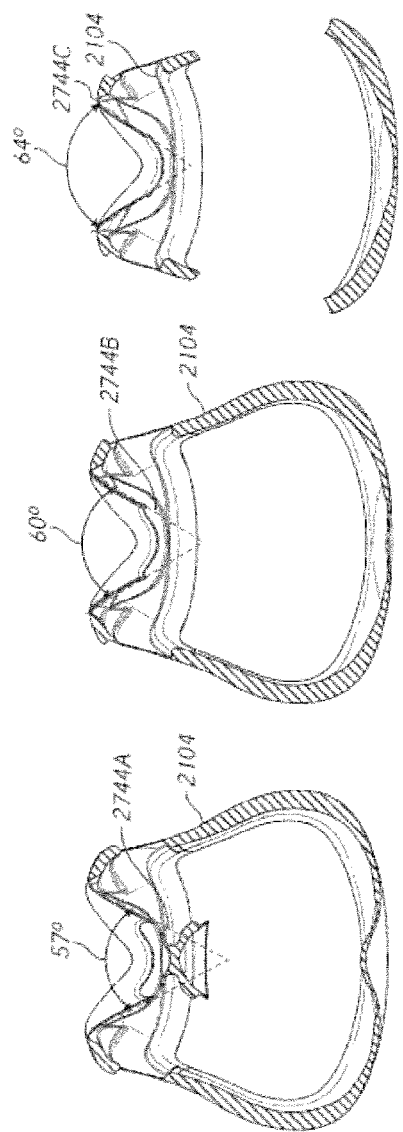

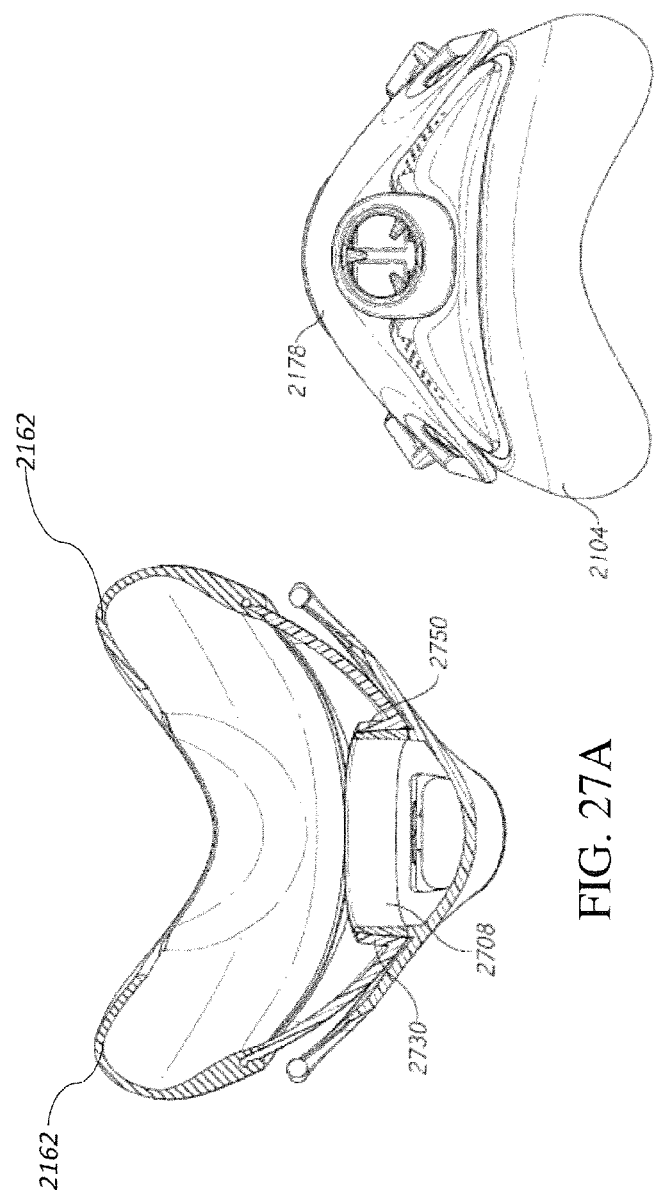

INTERFACE ASSEMBLIES FOR RESPIRATORY THERAPY

BACKGROUND

Field

The present disclosure relates to interface assemblies for respiratory therapy. In particular, the present disclosure relates to under-nose interface assemblies that do not cover the bridge of the user's nose.

Description of Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

One common type of patient interface assembly used with PAP therapy or other respiratory therapies involving the administration of gas includes a seal that contacts the bridge of the nose of a user of the interface assembly. The bridge of the nose is sensitive to pressure applied by the seal of the interface assembly. More recently, interface assemblies have become available that do not contact the bridge of the nose. Such interface assemblies can be referred to as "under-nose" interface assemblies. A need exists to provide improved under-nose interface assemblies with improved comfort and/or sealing performance, or to provide the public with a useful choice.

SUMMARY

The systems, methods and devices described herein have innovative aspects, no single one of which is indispensable or solely responsible for their desirable attributes. Without limiting the scope of the claims, some of the advantageous features will now be summarized.

A preferred embodiment involves a headgear assembly for a full-face under-nose respiratory mask. The headgear assembly comprises a strap assembly including a rear panel, a crown strap, a pair of opposing upper side straps, and a pair of opposing lower side straps. The headgear assembly comprises a flexible headgear connector element. A free end of each of the upper straps is coupled to the headgear connector element. The headgear connector element is configured to extend laterally across and be removably fastened to a frame of the respiratory mask below a tip of a user's nose.

In some configurations, the pair of upper side straps, the headgear connector element, and the crown strap forms a closed loop when the headgear connector element is removed from the frame.

In some configurations, the upper straps are adjustably coupled to the headgear connector element, such that a user can adjust the length of the upper straps when the upper straps are coupled to the headgear connector element.

In some configurations, the headgear connector element is configured to be coupled to and removed from the frame without removing the upper straps from the headgear connector element.

In some configurations, the headgear connector element comprises one or more apertures each configured to receive and removably retain a post on the frame.

In some configurations, the headgear connector element further comprises thickened portions at least partially surrounding each of the apertures.

In some configurations, the headgear connector element comprises a flexible material, such that the headgear connector element is able to conform to a curvature of the frame when removably fastened to the frame.

In some configurations, the headgear connector element comprises an elastomeric material.

In some configurations, the headgear connector element comprises a thermoplastic elastomer material.

In some configurations, the headgear connector element has a substantially upward-concave shape.

In some configurations, the headgear connector element comprises a pair of strap loops, each configured to retain one of the upper straps.

A preferred embodiment involves a respiratory mask assembly. The respiratory mask assembly comprises a frame, a cushion module carried by the frame, and a headgear assembly. The cushion module includes a seal and a housing. The seal comprises a nasal portion having a pair of upward extensions that extend upwardly from opposite sides of a central sealing surface, and an oral portion. The upward extensions may be referred to as paddles. The headgear assembly comprises a strap assembly including a rear panel, a crown strap, a pair of opposing upper side straps, and a pair of opposing lower side straps. The headgear assembly comprises a flexible headgear connector element. A free end of each of the upper straps is coupled to the headgear connector element. The headgear connector element is configured to extend laterally across and be removably fastened to the frame below the upward extensions of the seal.

In some configurations, the frame is removably connectable to the cushion module.

In some configurations, the pair of upper side straps, the headgear connector element, and the crown strap forms a closed loop when the headgear connector element is removed from the frame.

In some configurations, the upper straps are adjustably coupled to the headgear connector element, such that a user can adjust the length of the upper straps when the upper straps are coupled to the headgear connector element.

In some configurations, the respiratory mask assembly further comprises an inlet tube connected to the frame.

In some configurations, the headgear connector element is configured to be removably connected to the frame above the inlet tube.

In some configurations, the headgear connector element comprises one or more apertures each configured to receive and removably retain a post on the frame.

In some configurations, the post comprises an enlarged head that has a greater cross-sectional area than the cross-sectional area of the aperture of the headgear connector element.

In some configurations, the headgear connector element comprises a flexible material, such that the headgear connector element is able to conform to a curvature of the frame when removably connected to the frame.

A preferred embodiment involves a headgear connector element for connecting a headgear assembly to a respiratory mask assembly. The headgear connector element comprises an elongate flexible main body having a first end and a second end. The headgear connector element comprises a pair of strap loops. A first one of the pair of strap loops is attached to the first end and a second one of the pair of strap loops is attached to the second end of the main body. Each of the strap loops is configured to adjustably receive a strap of the headgear assembly. The headgear connector element comprises at least one aperture that extends through the main body of the headgear connector element. The aperture is configured to receive and removably retain a post of a frame of the mask assembly. The main body further comprises a thickened portion at least partially surrounding the at least one aperture.

In some configurations, the thickened portion is integrally formed with the main body.

In some configurations, the thickened portion is constructed of the same material as the main body.

In some configurations, the thickened portion is over-moulded to the main body.

In some configurations, the strap loops and the main body are constructed of different materials.

In some configurations, the main body is constructed of a thermoplastic elastomer material, such as for example silicone.

In some configurations, the strap loops are constructed of nylon.

In some configurations, each of the strap loops comprise a tab and wherein the main body is over-moulded over the tab.

In some configurations, the strap loops and the main body are attached by a welded joint.

In some configurations, the headgear connector element further comprises a concave portion along a central portion of a lower edge of the headgear connector element.

In some configurations, the headgear connector element is substantially flat when the headgear connector element is not coupled to the mask assembly.

A preferred embodiment involves a seal for a respiratory mask. The seal comprises an oral sealing portion configured to seal around a user's mouth. The seal comprises a nasal sealing portion configured to seal on the lower surface of a user's nose and be fully positioned below a bridge of the user's nose. The nasal sealing portion comprises a first and second upward extensions that extend upwardly from opposite sides of a central sealing surface. Each of the first and the second upward extensions has an internal wall configured to engage with a lateral side of the user's nose, and an external wall configured to provide structure to the nasal sealing portion, the internal and external walls being joined along an upper edge of the seal. The external walls comprise a pocket having a wall thickness that is less than the surrounding wall thickness.

In some configurations, the external walls further comprise a thickened rib extending along an upper portion of the external wall. The thickened rib is proximate to but spaced from the upper edge of the seal. The thickened rib has a wall thickness that is greater than the surrounding wall thickness. The thickened rib extends from a rear end of the external wall towards the front of the seal.

In some configurations, the thickened rib narrows at opposed ends.

In some configurations, the thickened rib has a curved or serpentine shape along its length.

In some configurations, the pocket is at least partially defined by the thickened rib.

In some configurations, the pocket is substantially teardrop shaped.

In some configurations, the pocket is located on an interior surface of the external walls.

In some configurations, the thickened rib is located on an interior surface of the external walls.

In some configurations, the thickened rib has varying thickness along its length.

According to an aspect of this disclosure, there is provided a respiratory mask assembly comprising
- a mask frame and a cushion module, the mask frame comprising a breathing gas inlet configured to receive a supply of breathable gas and to deliver the breathable gas to the cushion module, the cushion module being configured to form a seal with a user's face; and
- a bias vent on the mask frame and in communication with the cushion module, and configured to allow air to be exhausted from the cushion module through the bias vent;

wherein the mask assembly further comprises:
- a diffuser comprising diffuser material configured to extend over the bias vent, the diffuser material providing a tortuous air path from the bias vent through the diffuser; and
- a headgear connector element configured to be removably mounted on a front part of the mask frame so as to extend laterally across the mask frame to define opposed distal ends, each opposed distal end being configured to be connected to headgear, the headgear connector element comprising at least one aperture which is aligned with the bias vent when the headgear connector element is mounted on the mask frame.

The diffuser may be positioned between the mask frame and the headgear connector element. The diffuser may be positioned on the headgear connector element. The diffuser may be positioned on a front surface of the headgear connector element, that is, a surface of the headgear connector element that does not face the mask frame. At least a portion of the diffuser may be spaced from the bias vent so that the portion of the bias vent is not in direct contact with the bias vent. The diffuser may be provided on the headgear connector element and may be spaced away from the mask frame by the headgear connector element. The diffuser may be provided on the mask frame.

The diffuser may comprise a diffuser frame, configured to be mounted on the mask frame, and the diffuser material may be held by the diffuser frame. The diffuser material may be held by the diffuser frame so as to be spaced from the bias vent so that the portion of the bias vent is not in direct contact with the bias vent. The diffuser frame and/or the diffuser material may comprise at least one raised portion and at least one recessed portion, the raised portion being configured to space the recessed portion away from the bias vent. A plurality of raised portions and/or a plurality of recessed portions may be provided.

The diffuser may be of substantially the same shape and size as the bias vent.

The diffuser may be removably mounted on the mask assembly.

The diffuser may be removably mounted on the headgear connector element.

The diffuser may be removably mounted on the mask frame via a clip on one of the diffuser and mask frame which engages the other of the diffuser and the mask frame.

The diffuser may be permanently mounted on the mask assembly.

The headgear connector element may comprise a plurality of apertures. The plurality of apertures may be arranged in a U or V shaped vent array symmetrically about a vertical centre line of the mask frame, when the mask frame is viewed from the front. The or each aperture of the headgear connector element may be located above the breathing gas inlet when the headgear connector element is mounted on the mask frame.

The bias vent may comprise a plurality of vent holes. The plurality of vent holes may be arranged in a vent hole array. There may be a plurality of vent hole arrays. The vent hole arrays may be arranged symmetrically about a vertical centre line of the mask frame, when viewed from the front.

The headgear connector element may comprise an elongate flexible member that couples upper side straps of the headgear to the frame. The headgear connector element may extend laterally across the mask frame below a tip of a user's nose, when coupled to the mask frame.

The headgear connector element may comprise a central body portion, and a pair of opposed laterally extending arms extending from the central body portion, the arms terminating in the opposed distal ends for connection to the headgear, the aperture being provided in the central body portion. The central body portion may be arcuate so as extend downwardly from the arms in a U or V shape. The headgear connector element may comprise a laterally extending brace element, extending between the laterally extending arms, above the central body portion. The laterally extending arms may be inclined upwardly away from the central body portion.

The mask assembly may comprise a locating feature, configured to locate the headgear connector element against the mask frame to resist movement of the headgear connector element relative to the mask frame. The locating feature may be configured to locate the headgear connector element against the mask frame to resist vertical movement of the headgear connector element relative to the mask frame in a direction generally aligned with a vertical central line of the mask frame when viewed from the front. The locating feature may comprise a recess or protrusion on the mask frame, against which the headgear connector element abuts or otherwise engages.

According to another aspect of this disclosure there is provided a respiratory mask assembly comprising:
    a mask frame and a cushion module, the mask frame comprising a breathing gas inlet configured to receive a supply of breathable gas and to deliver the breathable gas to the cushion module, the cushion module being configured to form a seal with a user's face; and
    a bias vent on the mask frame and in communication with the cushion module, and configured to allow air to be exhausted from the cushion module through the bias vent;
wherein the mask assembly further comprises:
    a diffuser comprising a diffuser frame which holds diffuser material configured to extend over the bias vent, the diffuser material providing a tortuous air path from the bias vent through the diffuser, the diffuser frame being mounted on a front surface of the mask frame.

According to a further aspect of this disclosure there is provided a respiratory mask assembly comprising
    a mask frame and a cushion module, the mask frame comprising a breathing gas inlet configured to receive a supply of breathable gas and to deliver the breathable gas to the cushion module, the cushion module being configured to form a seal with a user's face;
    the mask frame being connected to the cushion module via a cushion connector comprising a gas flow duct extending from the mask frame into the cushion module and arranged to deliver breathable gas to the cushion module from the breathing gas inlet; and
    a bias vent in communication with the cushion module, and configured to allow air to be exhausted from the cushion module through the bias vent;
    wherein the bias vent is provided on the gas flow duct.

The mask assembly may comprise a diffuser comprising diffuser material configured to extend over the bias vent, the diffuser material providing a tortuous air path from the bias vent through the diffuser. The diffuser may be arcuate and configured to extend around part of the exterior of the gas flow duct. The diffuser may be configured to be concentrically mounted on the gas flow duct. The diffuser may be arranged as a ring of diffuser material configured to receive the gas flow duct.

The bias vent may comprise a plurality of vent holes. The vent holes may be spaced around at least a portion of the perimeter of the gas flow duct, when viewed along the longitudinal axis of the gas flow duct. The vent holes may be spaced around an upper portion of the perimeter of the gas flow duct. The vent holes may be provided only on the top half of the gas flow duct, when viewed along the longitudinal axis of the gas flow duct. In some examples, the vent holes may not be provided around a bottom portion of the perimeter of the gas flow duct. The vent holes may be equi-spaced. The mask assembly may comprise at least ten vent holes, preferably at least fifteen vent holes, and more preferably at least twenty vent holes. The vent holes may be arranged in a line, the line extending around at least a portion of the perimeter of the gas flow duct. The line of vent holes may be spaced along the longitudinal axis of the gas flow duct, so as to be spaced from an interior surface of the cushion module. There may be provided a plurality of lines of vent holes, each line being spaced along the longitudinal axis of the gas flow duct.

The vent holes may each comprise an inlet and an outlet, and a bore extending between the inlet and the outlet through the wall of the gas flow duct, a vent axis being defined between the centre of the vent inlet and the centre of the vent outlet, wherein the vent axis is inclined relative to the longitudinal axis of the gas flow duct. The vent axis may be angled between 10 and 85° from the longitudinal axis of the gas flow duct. The angle of the vent axis of all vent holes may be the same. The angle of the vent axis of at least one vent hole may be different from the angle of the vent axis of at least one other vent hole. The bias vent may be provided on a portion of the gas flow duct that is in a space between the mask frame and the cushion module.

A bias vent flow path may be defined for each vent hole, between an inner surface of the mask frame and an outer surface of the cushion module. The bias vent flow path may extend radially outwardly of the longitudinal axis of the gas flow duct. The bias vent flow path may be inclined relative to the longitudinal axis of the gas flow duct, when the mask assembly is viewed from the side.

According to a further aspect of this disclosure there is provided a respiratory mask assembly comprising
- a mask frame and a cushion module, the mask frame comprising a breathing gas inlet configured to receive a supply of breathable gas and to deliver the breathable gas to the cushion module, the cushion module being configured to form a seal with a user's face; and
- the cushion module comprising a bias vent in communication with the cushion module, and configured to allow air to be exhausted from the cushion module through the bias vent;
- the mask frame being connected to the cushion module via a cushion connector comprising a gas flow duct extending from the mask frame into the cushion module and arranged to deliver breathable gas to the cushion module from the breathing gas inlet;

wherein the mask assembly further comprises:
- a diffuser comprising a diffuser frame, and diffuser material held by the diffuser frame and configured to extend over the bias vent, the diffuser material providing a tortuous air path from the bias vent through the diffuser; the diffuser frame comprising a mounting portion being configured to be mounted on the cushion connector.

The cushion module may comprise an mounting aperture configured to receive the gas flow duct of the cushion connector, the mounting portion of the diffuser frame comprising a mounting ring, the mounting ring being configured to be mounted on the cushion module concentrically with the mounting aperture.

The cushion module may comprise an annular recess which is concentric with, and extends around the periphery of, the mounting aperture, the mounting ring of the diffuser frame being received in the annular recess.

The bias vent may be located below the mounting aperture, when the cushion module is viewed along the axis of the inlet aperture.

The bias vent may comprise a plurality of vent holes. The plurality of vent holes may be arranged in a vent hole array. A plurality of vent hole arrays may be provided. The vent hole arrays may be arranged symmetrically about a vertical centre line of the cushion module, when viewed from the front. Each vent hole array may be laterally spaced away from a vertical centre line of the cushion module. Each vent hole array may be adjacent a respective side of the inlet aperture of the cushion module. Each vent hole array may be adjacent a respective side of a valve recess of the cushion module, the valve recess being a region below the inlet aperture which is recessed to receive part of a gas delivery inlet tube or connector assembly.

The diffuser frame may comprise a plurality of sub-frames, each of which holds a respective portion of diffuser material, each sub-frame being aligned with a respective vent hole array when the diffuser is mounted on the cushion module. The sub-frames may extend laterally outwardly from the mounting portion. The sub-frames may extend laterally outwardly from a lower part of the mounting portion. The diffuser may comprise a brace element which extends between the sub-frames, below the mounting portion. The mounting portion and the sub-frames may together define an omega shape. The sub-frames may be substantially triangular.

The diffuser may be permanently or removably mounted on the cushion module. The diffuser may be retained on the cushion module by frictional engagement with the cushion module. The diffuser may be retained on the cushion module by the cushion connector, that is by being sandwiched between the mask frame and the cushion module.

The diffuser may comprise a rear surface, the rear surface being shaped to be complimentary to a front surface of the cushion module against which the diffuser is adjacent, when the diffuser is mounted on the cushion module.

The diffuser frame and/or the mounting portion, may be of at least partially hollow construction and/or of at least partially solid construction.

The diffuser material may be permanently or removably mounted on the diffuser frame.

The diffuser frame and/or the diffuser material may be shaped to define at least one recess which forms an alternative gas flow path through the diffuser.

The diffuser mounting portion may comprise the diffuser frame which holds the diffuser material, the diffuser frame being mounted on the cushion module.

The diffuser frame and/or the cushion module may comprise mounting features configured to mount the diffuser frame on the cushion module to retain the diffuser frame on the cushion module.

According to another aspect of this disclosure, there is provided a respiratory mask assembly comprising
- a mask frame and a cushion module, the mask frame comprising a breathing gas inlet configured to receive a supply of breathable gas and to deliver the breathable gas to the cushion module, the cushion module being configured to form a seal with a user's face; the cushion module comprising a mounting aperture;
- the mask frame being connected to the cushion module via a cushion connector comprising a gas flow duct extending from the mask frame and into the cushion module through the mounting aperture, and arranged to deliver breathable gas to the cushion module from the breathing gas inlet;
- the cushion module comprising a bias vent in communication with the cushion module, and configured to allow air to be exhausted from the cushion module through the bias vent;
- wherein the cushion module comprises a recess adjacent the mounting aperture, the recess forming a cavity defined between the cushion module and the mask frame when the mask frame is connected to the cushion module, the bias vent comprising at least one vent hole located in the recess.

The recess may be an annular recess, extending around the perimeter of, and being concentric with, the mounting aperture.

The vent hole may comprise an inlet and an outlet, and a bore extending between the inlet and the outlet through the wall of the recess, a vent axis being defined between the centre of the vent inlet and the centre of the vent outlet, wherein the vent axis extends substantially in the direction of the longitudinal axis of the mounting aperture of the cushion module.

The vent axis may be substantially parallel to the longitudinal axis of the mounting aperture of the cushion module. The vent axis may be inclined relative to the longitudinal axis of the mounting aperture of the cushion module.

The bore of the or each vent hole may comprise a side wall, when the vent hole is viewed in transverse cross section, the side wall being inclined relative to the longitudinal axis of the mounting aperture of the cushion module. A radially outer and/or a radially inner part of the side wall of the bore may be inclined.

The vent hole may comprise an inlet and an outlet, and a bore extending between the inlet and the outlet through the wall of the recess, a vent axis being defined between the centre of the vent inlet and the centre of the vent outlet, wherein the vent axis extends substantially perpendicularly to the longitudinal axis of the mounting aperture of the cushion module, such that each vent axis extends radially outwardly from the mounting aperture, the gas flow duct of the cushion connector also comprising at least one vent hole, aligned with the vent hole in the recess, such that air can vent from the cushion connector and into the recess through the aligned vent holes.

The mask assembly may comprise a diffuser, the diffuser comprising an annulus of diffuser material configured to be received in the annular recess to cover the or each vent hole of the bias vent.

The cavity may be defined by the recess between the mask frame and the cushion module has a cavity volume, the volume of the diffuser being less than the cavity volume.

The diffuser may be shaped and dimensioned such that when received in the cavity, the diffuser is not substantially compressed, and does not substantially deform.

The diffuser material and the recess may be configured such that the diffuser material is spaced from the vent hole.

An abutment feature may be provided against which the diffuser abuts when mounted in the recess, the abutment feature limiting movement of the diffuser material towards the vent hole.

The bias vent may comprise a plurality of vent holes. The vent holes may extend around the entire perimeter of the mounting aperture. The bias vent holes may be equi-spaced.

A bias vent flow path may be defined for the or each vent hole, between an inner surface of the mask frame and an outer surface of the cushion module. The bias vent flow path may extend radially outwardly of the longitudinal axis of the mounting aperture. The bias vent flow path may be inclined relative to the longitudinal axis of the mounting aperture, when the mask assembly is viewed from the side.

According to another aspect of this disclosure there is provided a respiratory mask assembly comprising
- a mask frame and a cushion module, the mask frame comprising a breathing gas inlet configured to receive a supply of breathable gas and to deliver the breathable gas to the cushion module, the cushion module comprising a housing and a cushion seal configured to form a seal with a user's face; and
- a bias vent on the mask frame or the cushion module configured to allow air to be exhausted from the cushion module through the bias vent; the bias vent comprising a plurality of vent holes arranged in at least one vent hole array;
- the mask frame being removably connected to the cushion module via a cushion connector comprising a gas flow duct extending from the mask frame into the cushion module and arranged to deliver breathable gas to the cushion module from the breathing gas inlet;
- wherein the mask assembly further comprises:
- a diffuser comprising diffuser material configured to extend over the bias vent, the diffuser material providing a tortuous air path from the bias vent through the diffuser; the diffuser being of complementary shape to the vent hole array; and
- a headgear connector element configured to be removably mounted on a front part of the mask frame so as to extend laterally across the mask frame to define opposed distal ends, each end being configured to be connected to headgear;
- wherein the diffuser is mounted on one or more of the mask frame, cushion module, cushion connector, and headgear connector element.

According to a further aspect of this disclosure there is provided a respiratory mask assembly comprising
- a mask frame and a cushion module, the mask frame comprising a breathing gas inlet configured to receive a supply of breathable gas and to deliver the breathable gas to the cushion module, the cushion module being configured to form a seal with a user's face; and
- a bias vent in communication with the cushion module, and configured to allow air to be exhausted from the cushion module through the bias vent;
- the mask frame being connected to the cushion module via a cushion connector comprising a gas flow duct extending from the mask frame into the cushion module and arranged to deliver breathable gas to the cushion module from the breathing gas inlet;
- wherein the mask assembly further comprises:
- a diffuser comprising diffuser material configured to extend over the bias vent, the diffuser material providing a tortuous air path from the bias vent through the diffuser; wherein the diffuser is located between the mask frame and the cushion module.

According to another aspect of this disclosure there is provided a respiratory mask assembly comprising
- a mask frame and a cushion module, the mask frame comprising a breathing gas inlet configured to receive a supply of breathable gas and to deliver the breathable gas to the cushion module, the cushion module being configured to form a seal with a user's face; and
- a bias vent in communication with the cushion module, and configured to allow air to be exhausted from the cushion module through the bias vent;
- the mask frame being connected to the cushion module via a cushion connector comprising a gas flow duct extending from the mask frame into the cushion module and arranged to deliver breathable gas to the cushion module from the breathing gas inlet;
- wherein the mask assembly further comprises:
- a diffuser comprising diffuser material configured to extend over the bias vent, the diffuser material providing a tortuous air path from the bias vent through the diffuser; wherein the diffuser is located between the mask frame and another component of the mask assembly.

The mask assembly may further comprise a headgear assembly. The headgear assembly may comprise a strap assembly including at least a pair of opposing side straps, and/or a rear strap or panel, and/or a crown strap. The pair of opposing side straps may be a pair of opposing upper side straps; the mask assembly further comprising a pair of opposing lower side straps. A free end of each of the upper straps may be coupled to a or the headgear connector element. A free end of each of the lower side straps may be coupled to the mask frame.

The cushion module may comprise a cushion seal and a cushion housing. The cushion seal may comprise a nasal portion having a pair of upward extensions that extend upwardly from opposite sides of a central sealing surface, and an oral portion.

The mask assembly may further comprise any one or more of:
a) a tube connector for connecting a breathing gas delivery tube to the breathing gas inlet
b) a breathing gas delivery tube.

The breathing gas delivery tube may comprise:

a) a tube heater wire; and/or
b) a sensor wire; and/or
c) a connector cuff at an end of the tube.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 2A is a front, top and side perspective view of a mask assembly with the headgear omitted and an entirety of the air supply conduit shown.

FIG. 2B is a rear, top and side perspective close-up view of the mask assembly of FIG. 2A.

FIG. 3A is a front view of a frame of the mask assembly of FIG. 2A.

FIG. 3B is a rear view of the frame of the mask assembly of FIG. 2A.

FIG. 4 is a side view of the frame of the mask assembly of FIG. 2A.

FIG. 5 is a side cross-sectional view of the frame of the mask assembly of FIG. 2A taken along the line 5-5 of FIG. 3A.

FIG. 6 is a side cross-sectional view of the frame of the mask assembly of FIG. 2A taken along the line 6-6 of FIG. 3A.

FIG. 9 is a front, bottom, and side perspective exploded view of the frame of the mask assembly of FIG. 2A.

FIG. 10 is a rear, bottom, and side perspective exploded view of the frame of the mask assembly of FIG. 2A.

FIG. 19A is a rear cross-sectional view of the mask seal of the mask assembly of FIG. 2A taken along the line 19A-19A of FIG. 18.

FIG. 19B is a rear cross-sectional view of the mask seal of the mask assembly of FIG. 2A taken along the line 19B-19B of FIG. 18.

FIG. 19C is a rear cross-sectional view of the mask seal of the mask assembly of FIG. 2A taken along the line 19C-19C of FIG. 18.

FIG. 27A is a top cross-sectional view of the mask assembly of FIG. 2A.

FIG. 27B is a bottom view of the mask assembly of FIG. 2A.

yoke, with diffuser material omitted.

Figure 45:
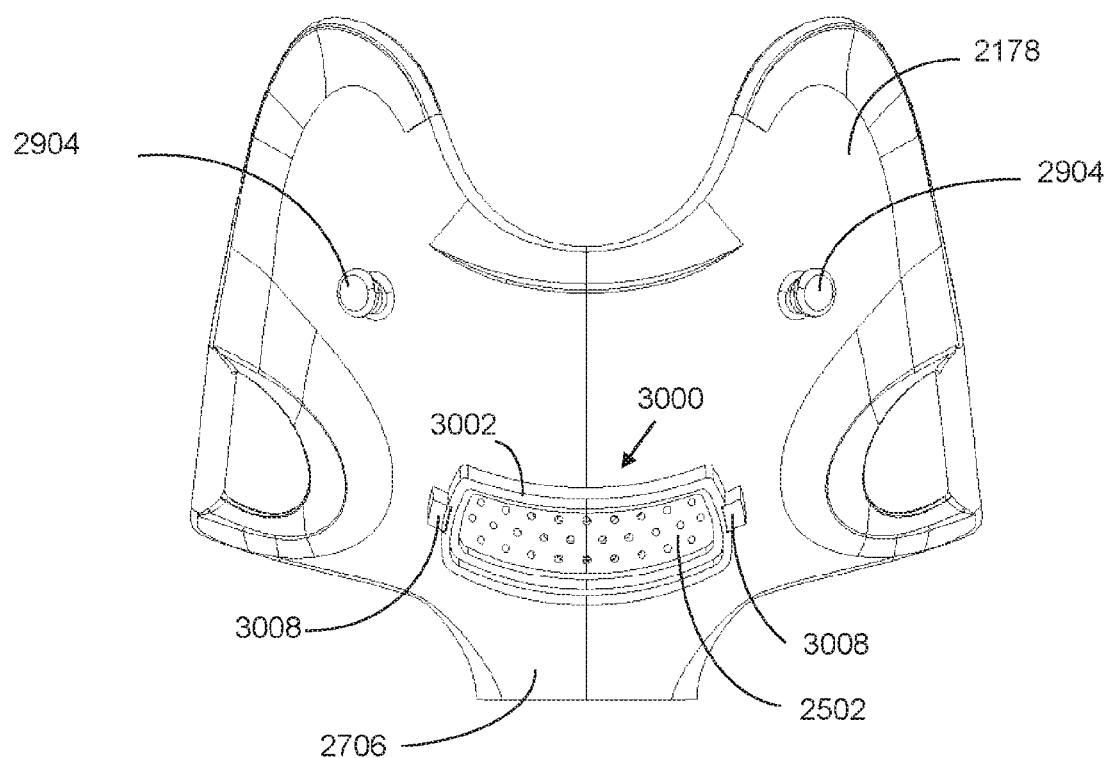
FIG. 45 is front view of another mask frame of an interface assembly in accordance with aspects of this disclosure.
Figure 46:
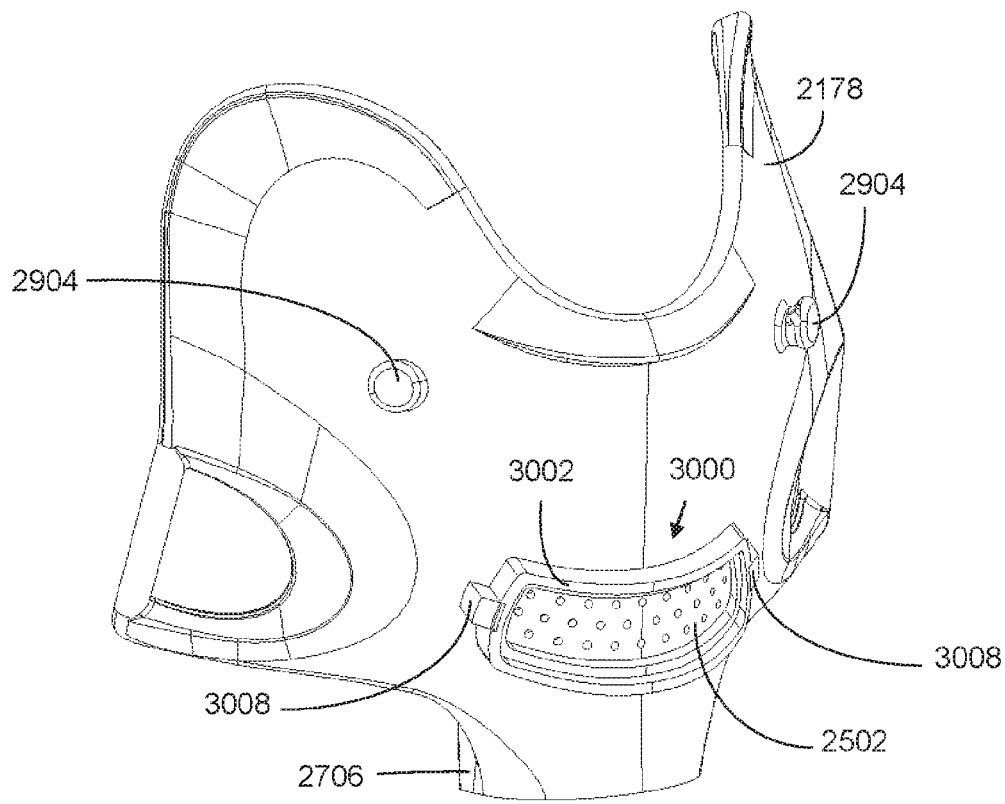
FIG. 46 is a perspective view of the mask frame of FIG. 45.
Figure 47:
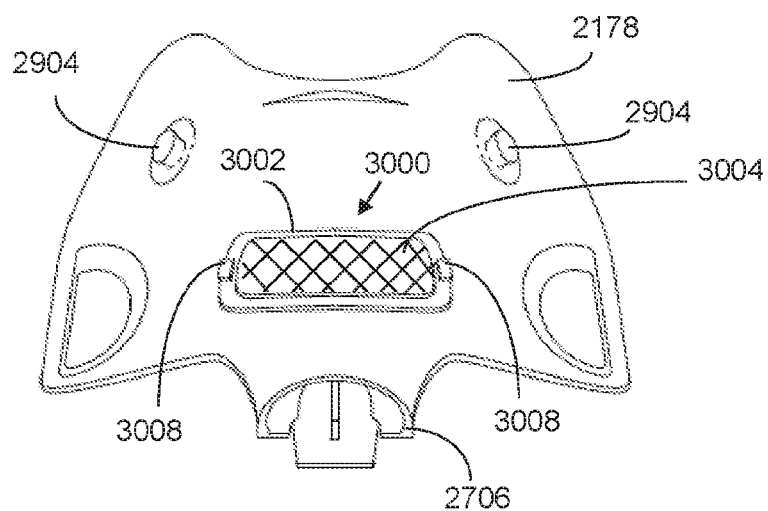

FIG. 47 is a front perspective view of the mask frame of FIGS. 45 to 46, with diffuser material shown.

Figure 48:
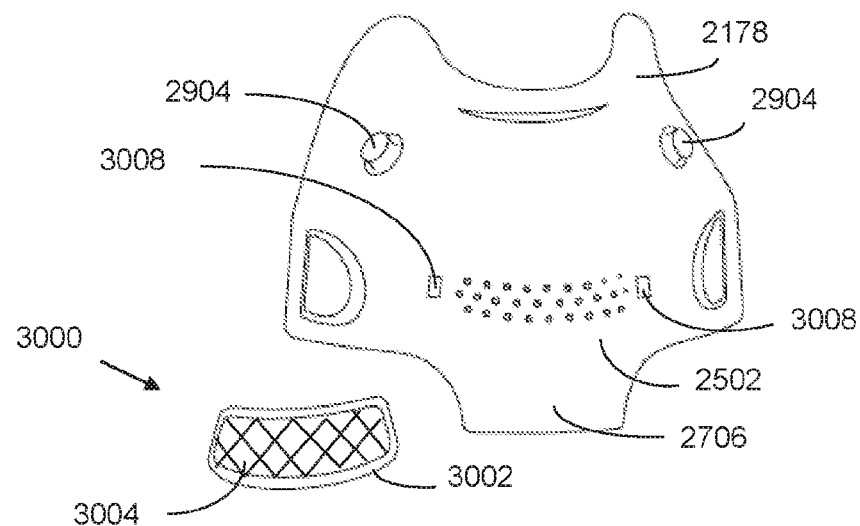

FIG. 48 is a front perspective view of the mask frame of FIGS. 45 to 46, with a diffuser and diffuser material removed from the mask frame.

Figure 49:
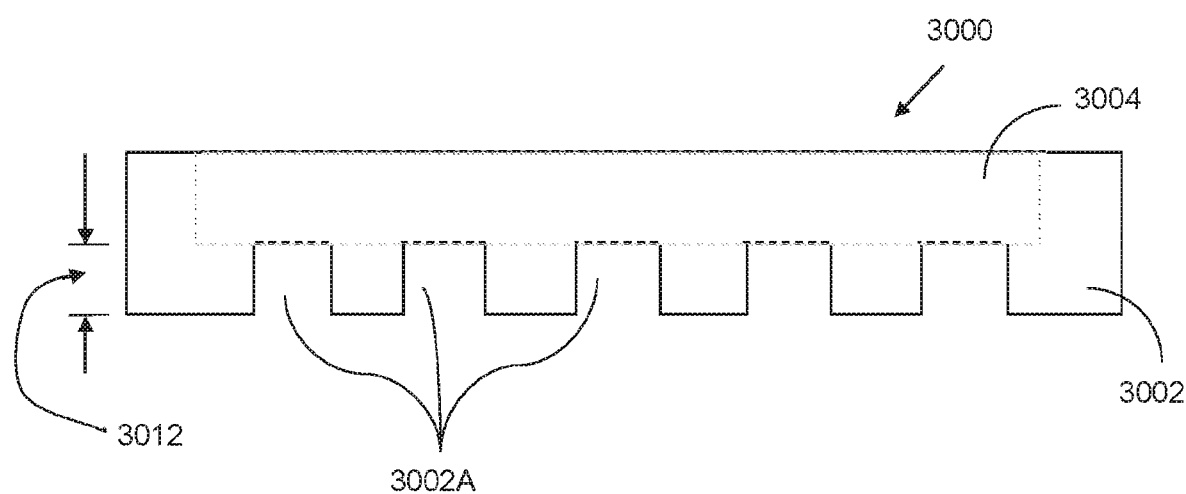

FIG. 49 is a sectional view through the diffuser of FIG. 48.

Figure 50:
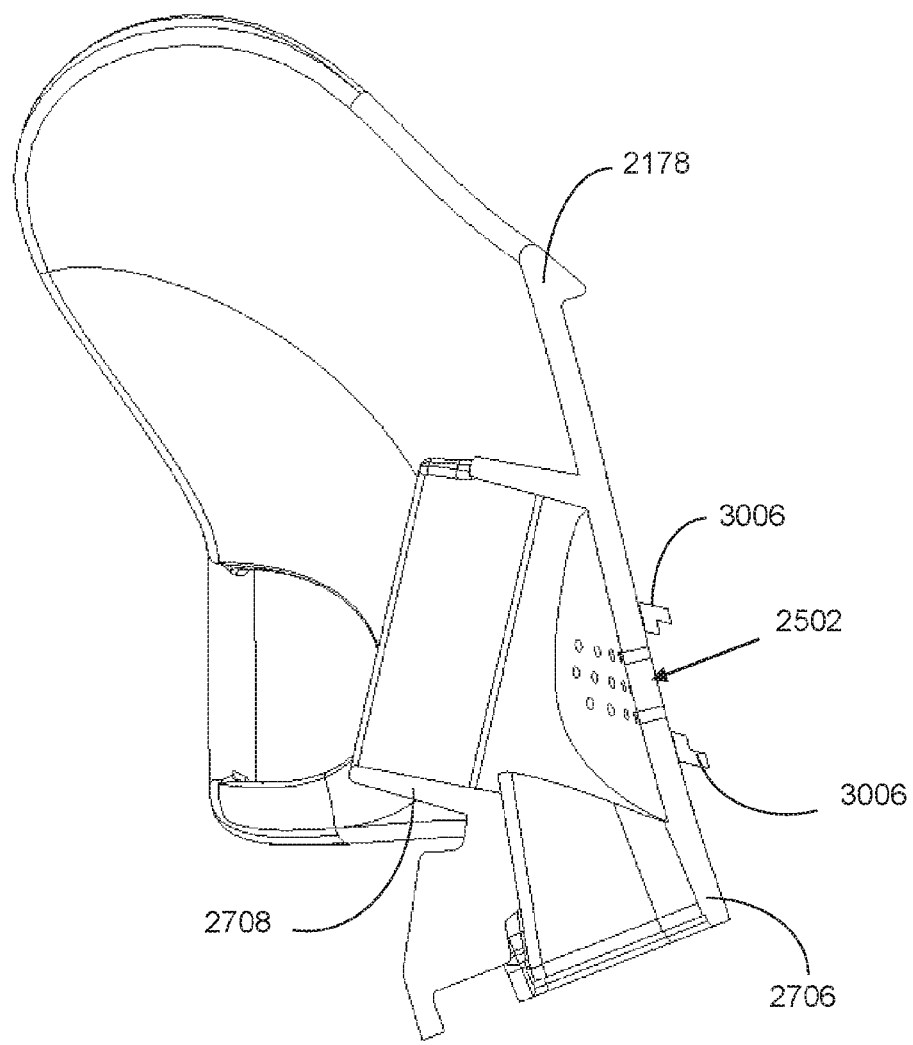

FIG. 50 is a sectional side view of the mask frame of FIGS. 45 to 46, with a diffuser and diffuser material removed from the mask frame.

Figure 51:
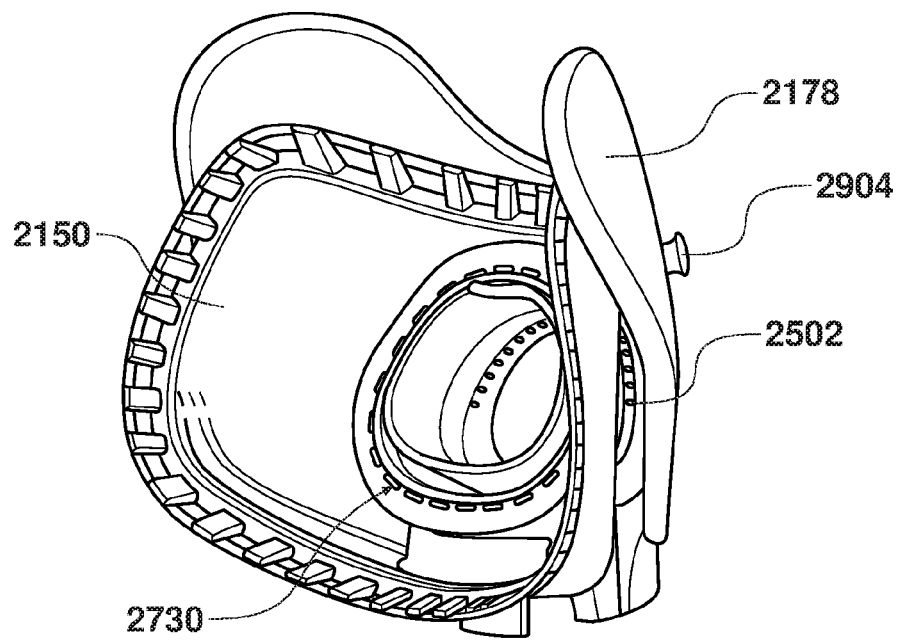

FIG. 51 is a perspective view from the rear of a mask frame and mask seal in accordance with aspects of this disclosure.

Figure 52:
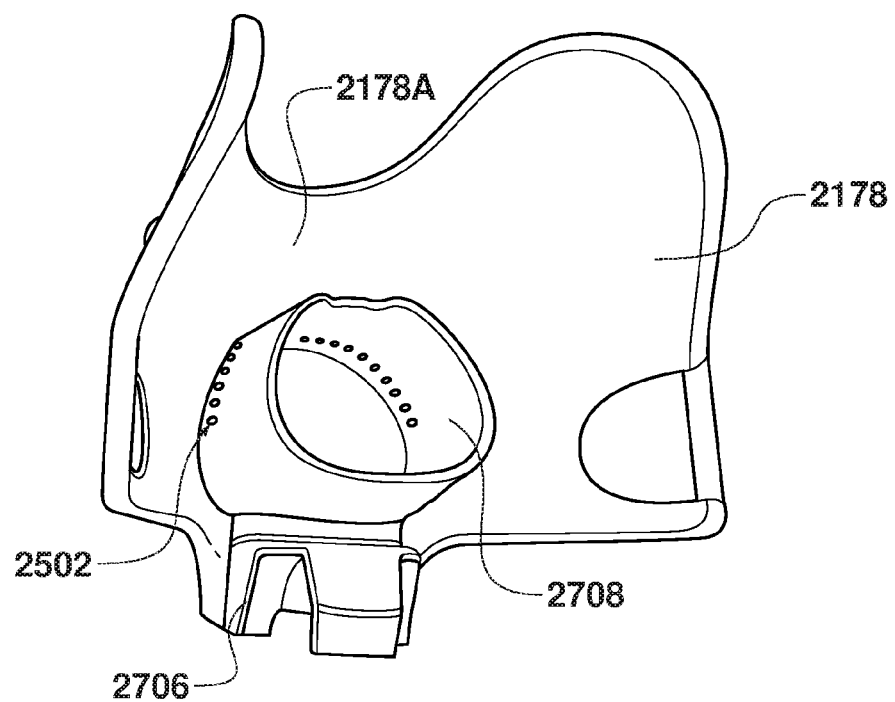

FIG. 52 is a perspective view from the rear of the mask frame of FIG. 51.

Figure 53:
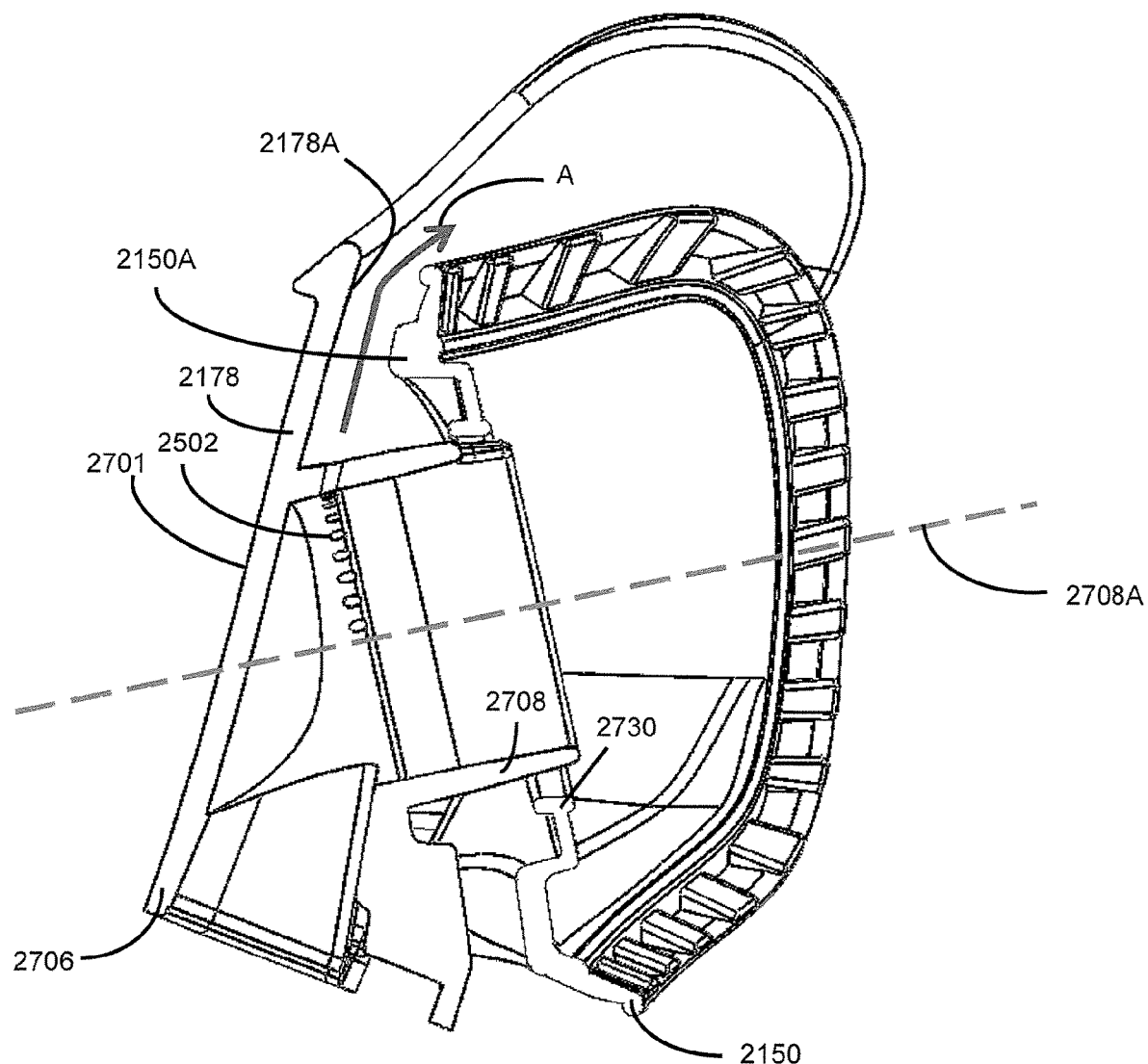

FIG. 53 is a sectional side view of the mask frame and mask seal of FIG. 51.

Figure 54:
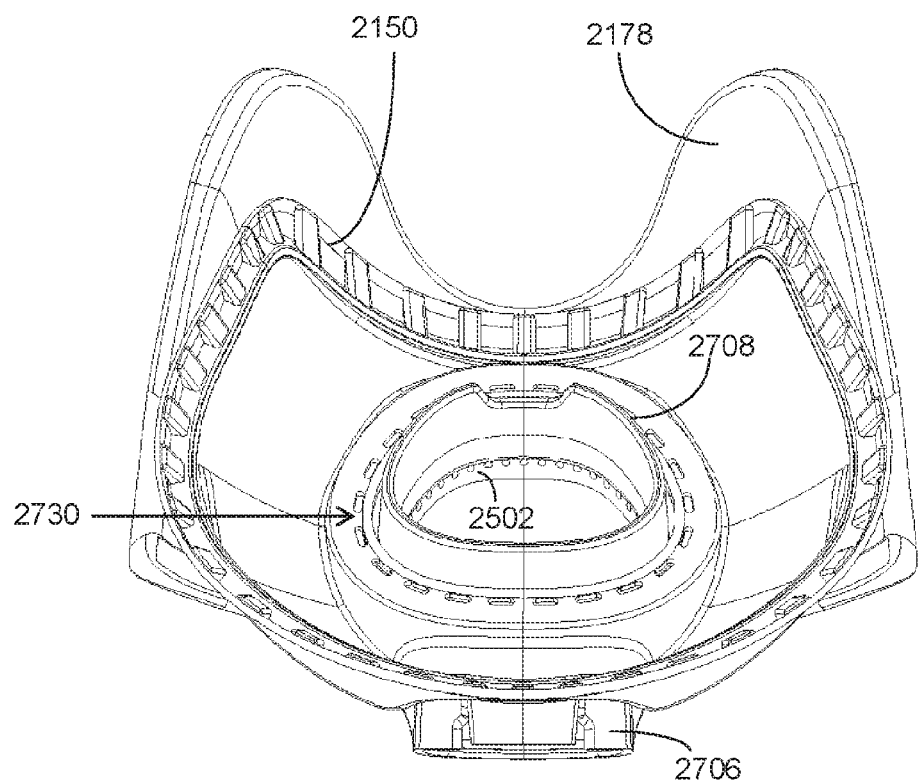

FIG. 54 is a rear perspective view of the mask frame and mask seal of FIG. 51.

Figure 55:
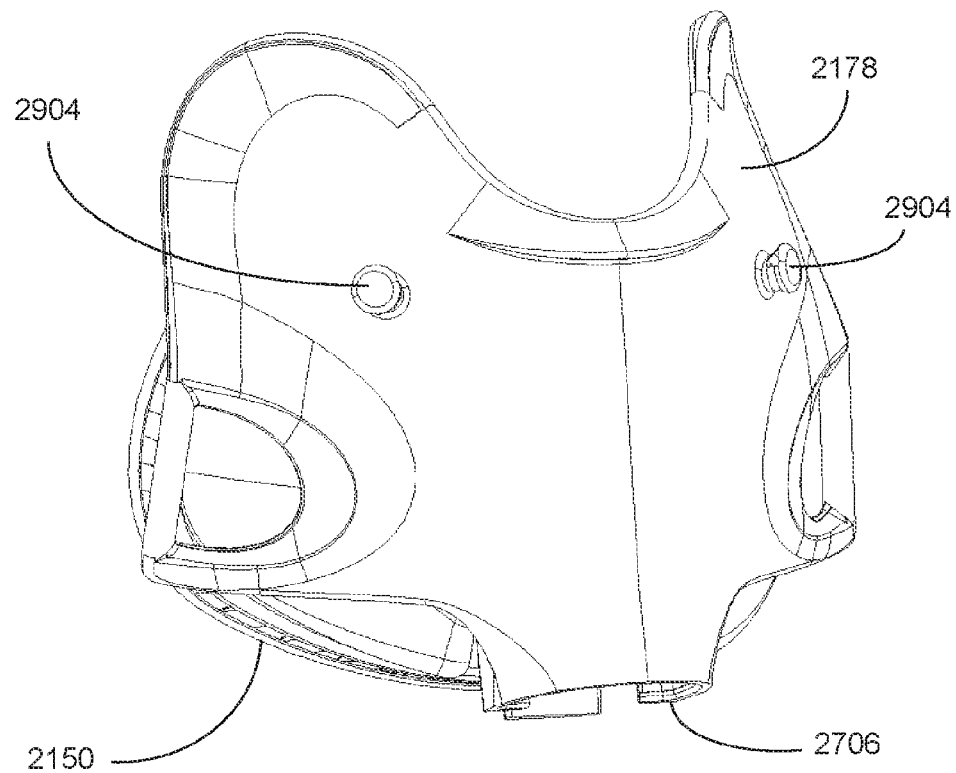

FIG. 55 is a perspective view from the front of the mask frame and mask seal of FIG. 50.

Figure 56:
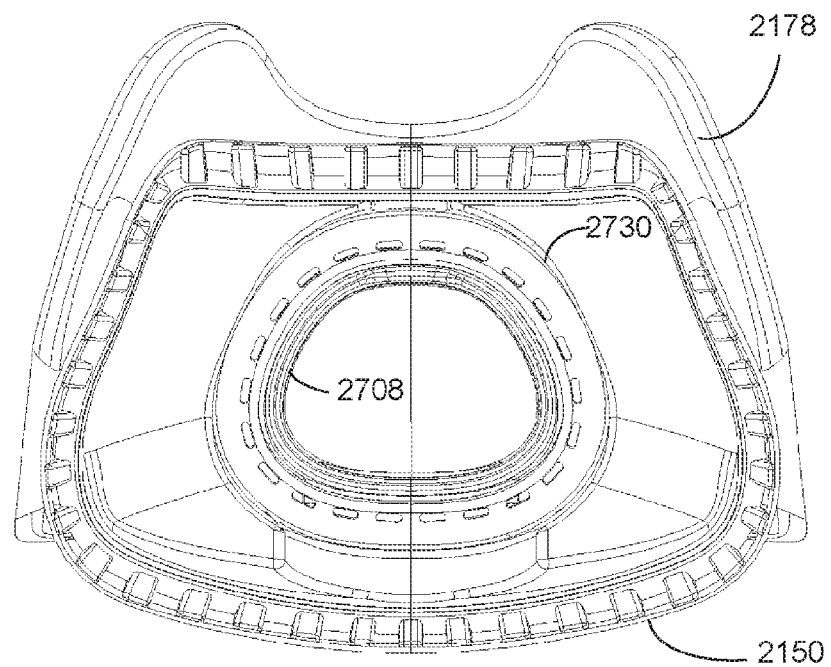

FIG. 56 is a rear view of the mask frame and mask seal of FIG. 50.

Figure 57:
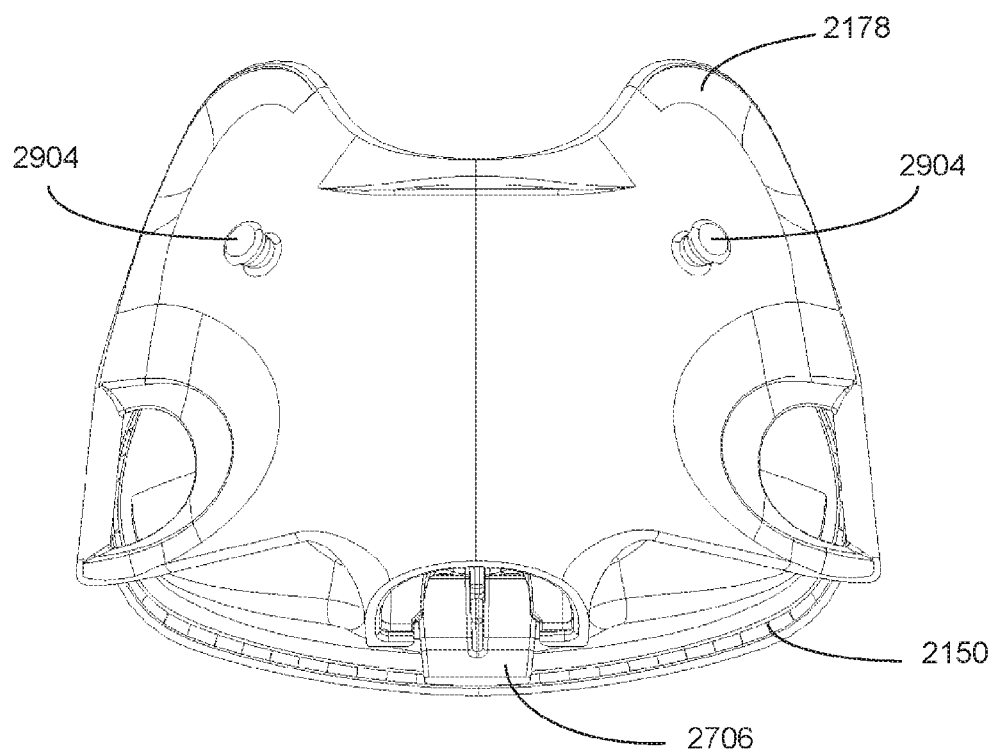

FIG. 57 is a front view of the mask frame and mask seal of FIG. 50.

Figure 58:
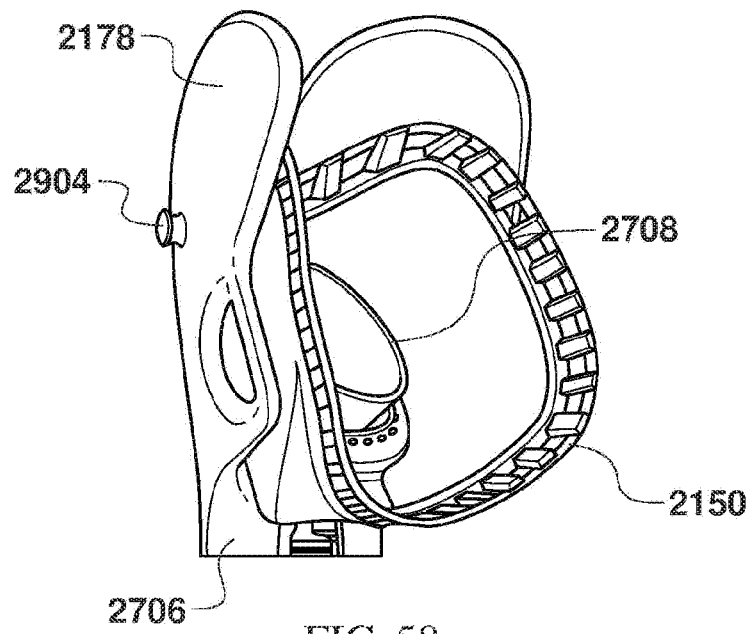
Figure 59:
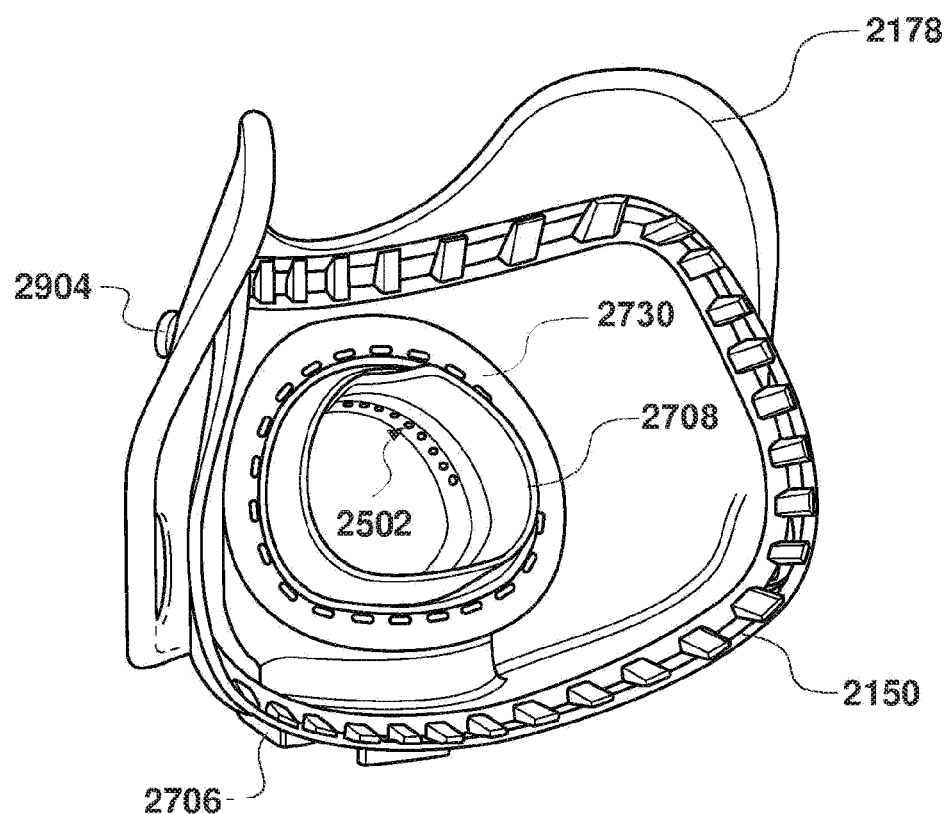

FIGS. 58 and 59 are perspective views from the rear of the mask frame and mask seal of FIG. 50.

Figure 60:
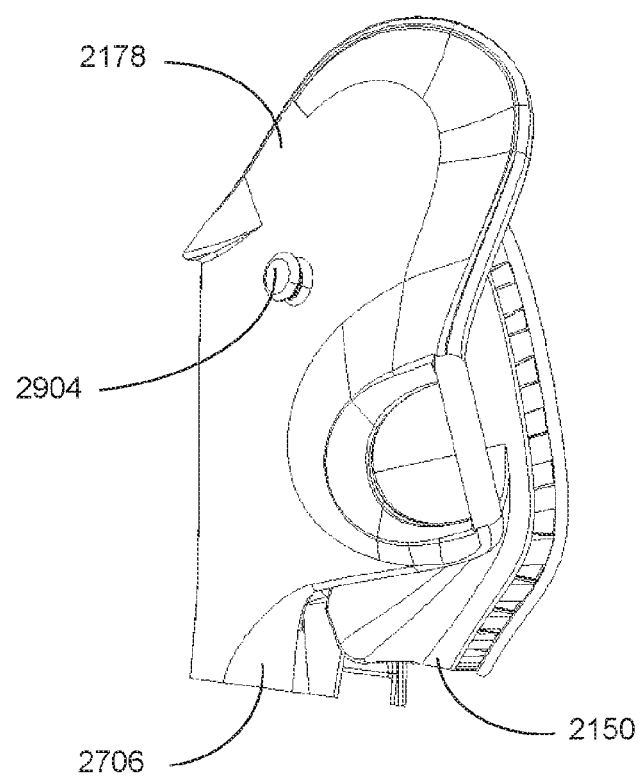

FIG. 60 is a side view of the mask frame and mask seal of FIG. 50.

Figure 61:
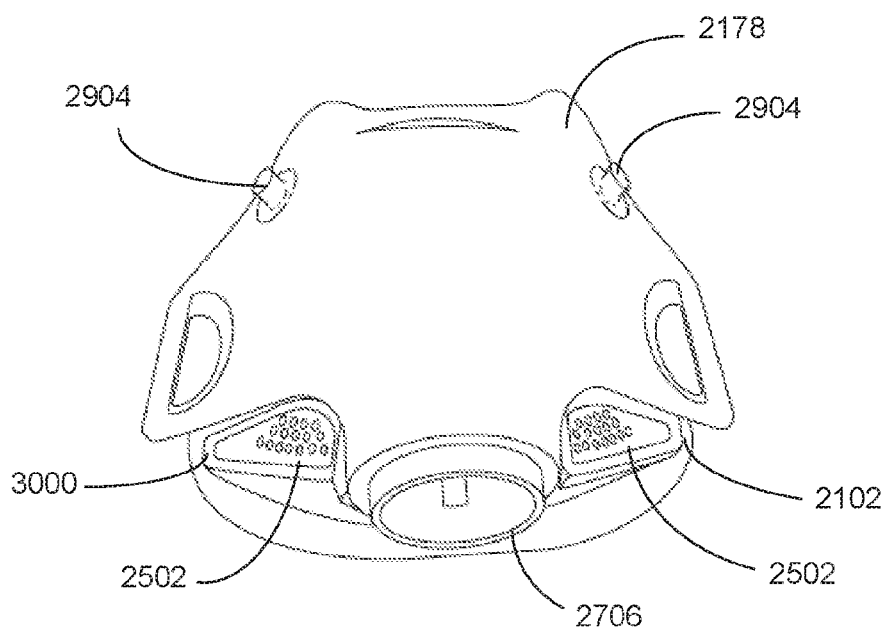

FIG. 61 is a front perspective view of another mask frame and mask seal in accordance with aspects of this disclosure.

Figure 62:
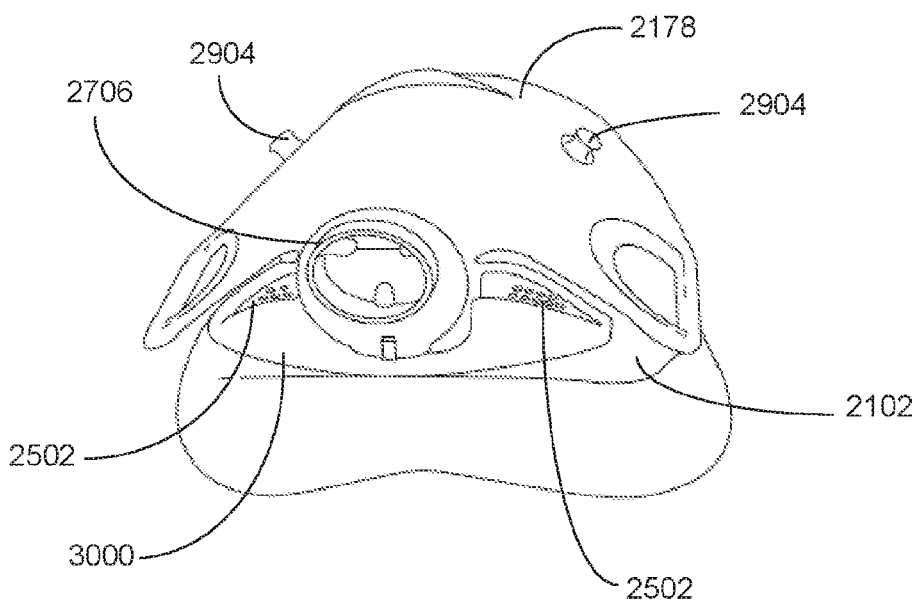

FIG. 62 is a view from underneath of the mask frame and mask seal of FIG. 61.

Figure 63:
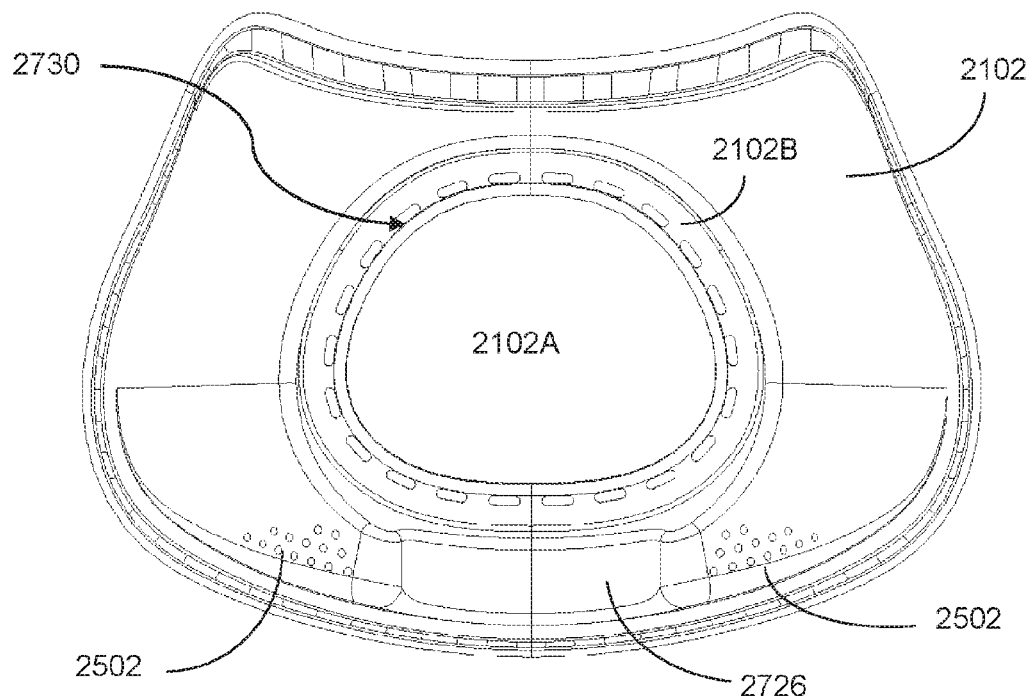

FIG. 63 is a front view of the mask seal of FIG. 62.

Figure 64:
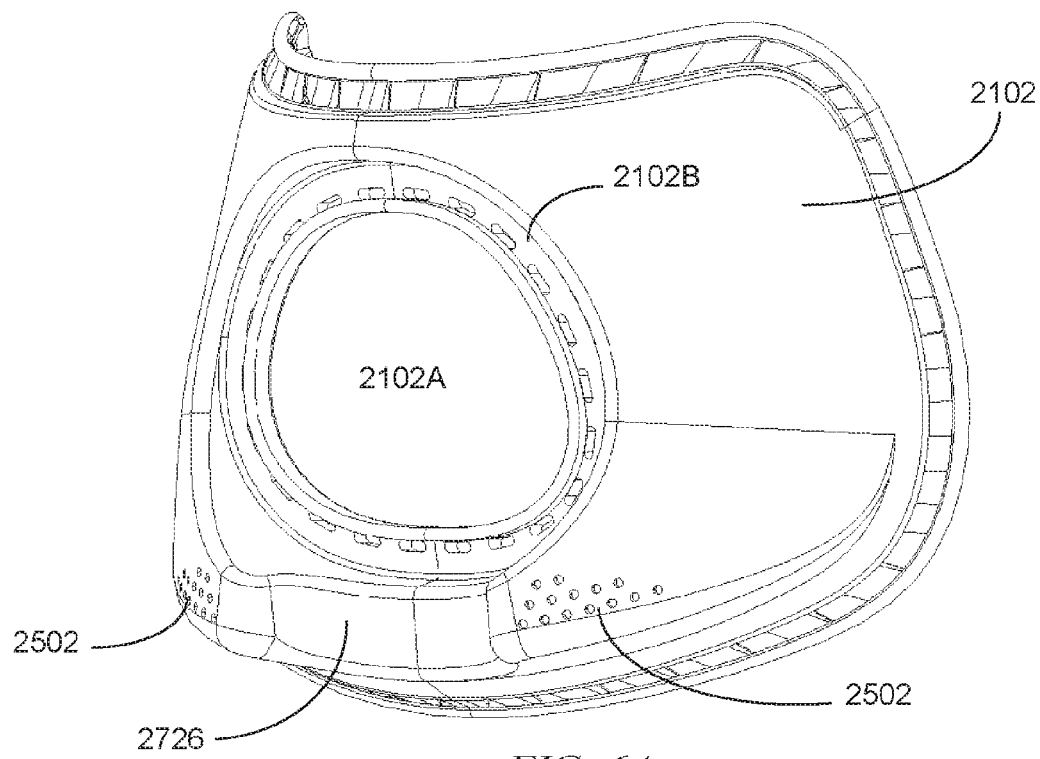
Figure 65:
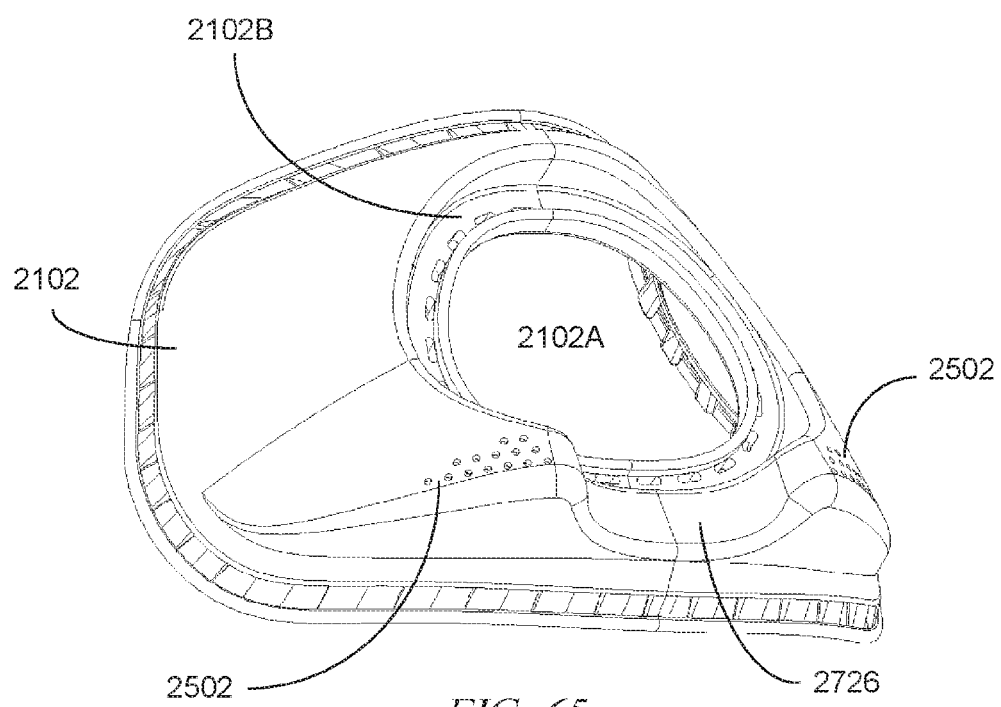

FIGS. 64 and 65 are perspective views of the mask seal of FIG. 62.

FIGS. 66a and 66b are front and rear views of a diffuser for use with the mask seal of FIG. 61.

Figure 66:
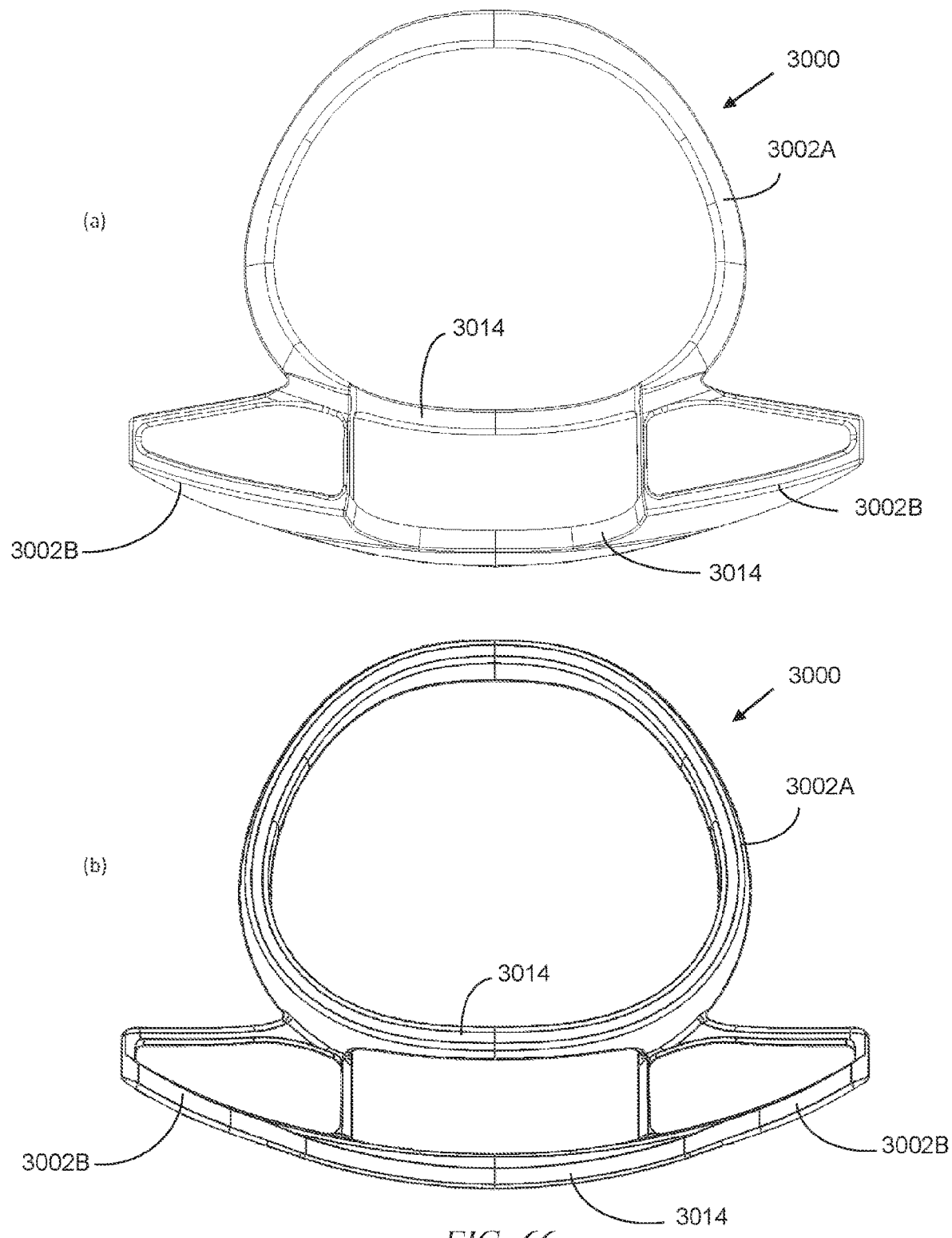
Figure 67:
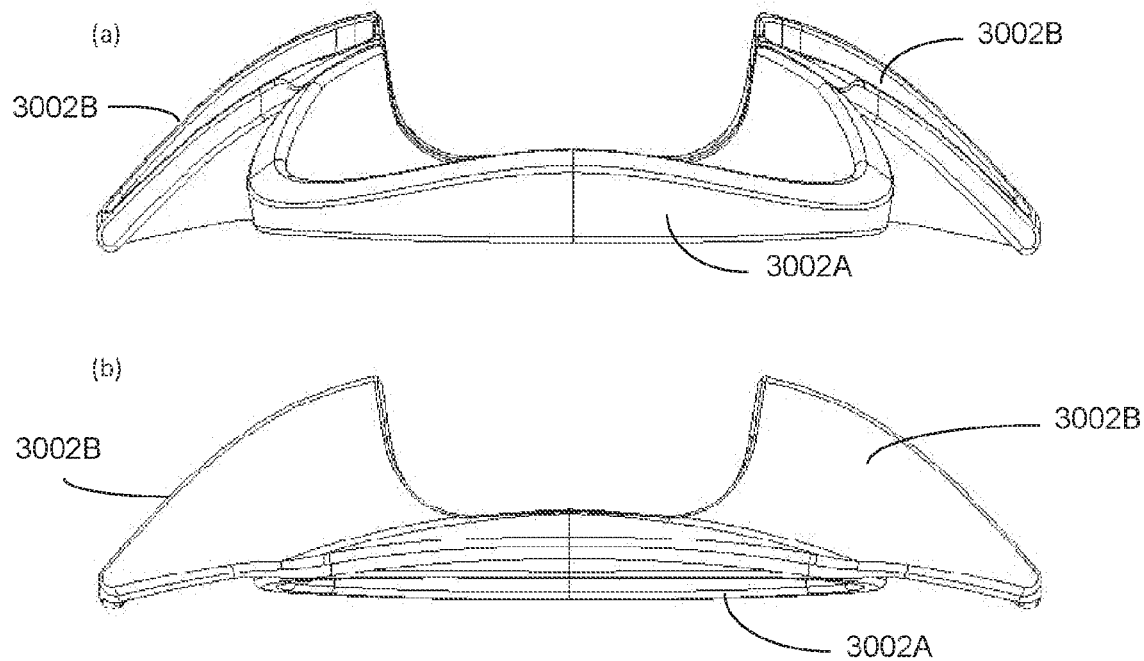

FIGS. 67a and 67b are top and bottom views of the diffuser of FIG. 66.

Figure 68:
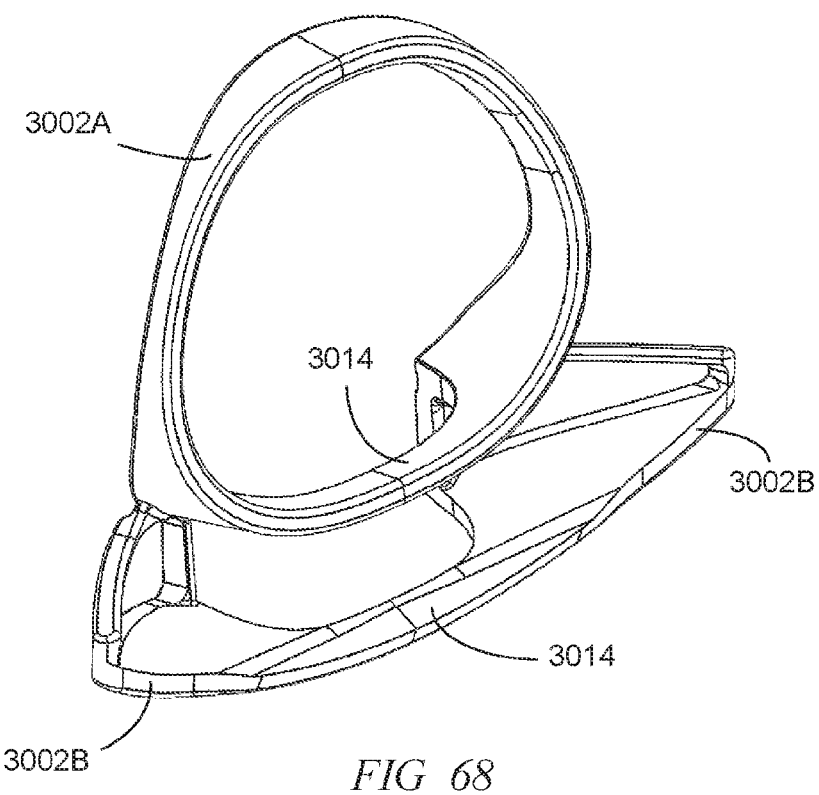

FIG. 68 is a rear perspective view of the diffuser of FIG. 68.

Figure 69:
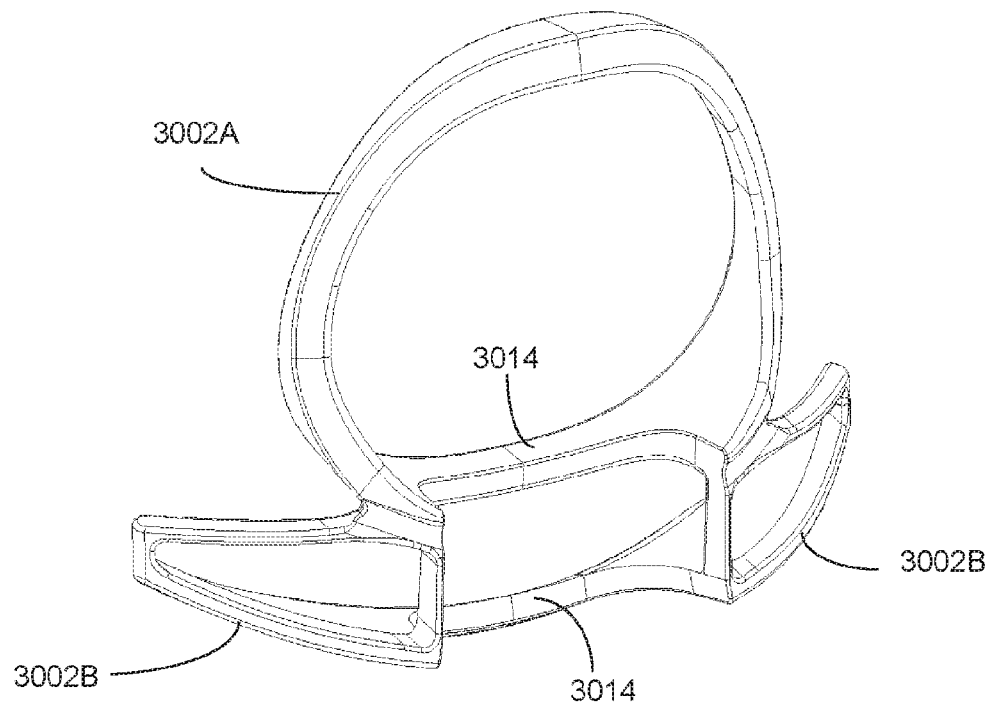
Figure 70:
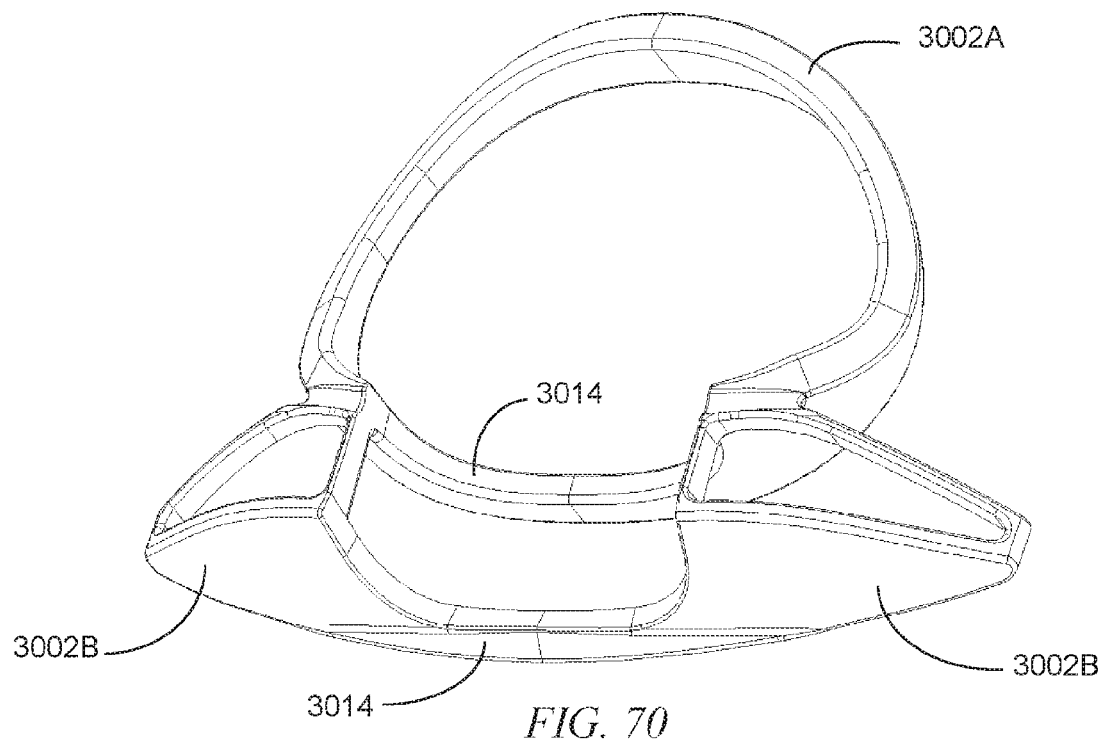

FIGS. 69 and 70 are front perspective views of the diffuser of FIG. 68.

Figure 71:
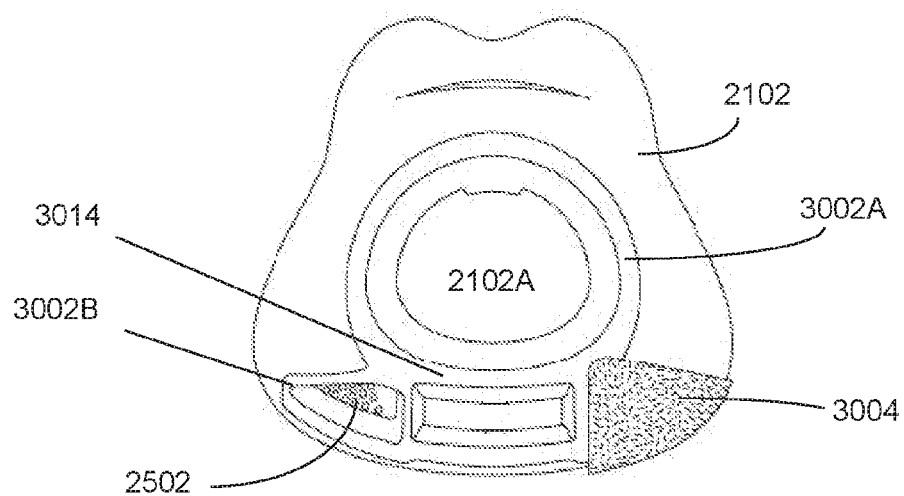

FIG. 71 is a front view of the diffuser and mask seal of FIG. 68.

Figure 72:
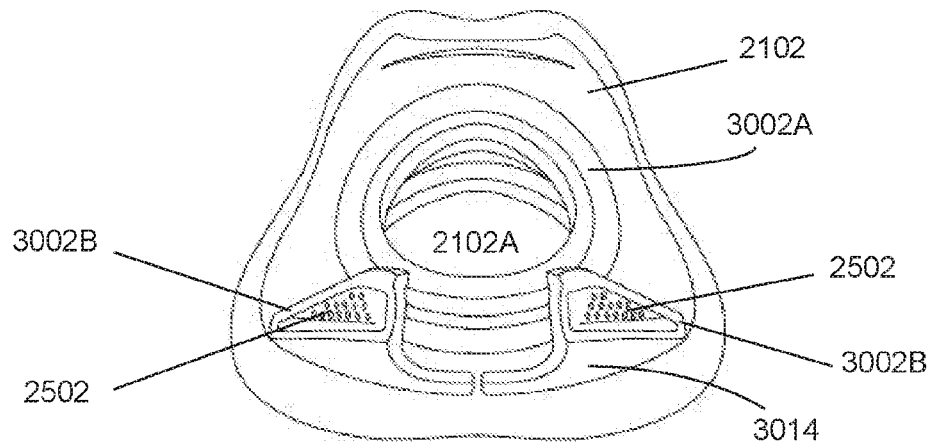

FIG. 72 is a front view of another diffuser for use with the mask seal of FIG. 62.

Figure 73:
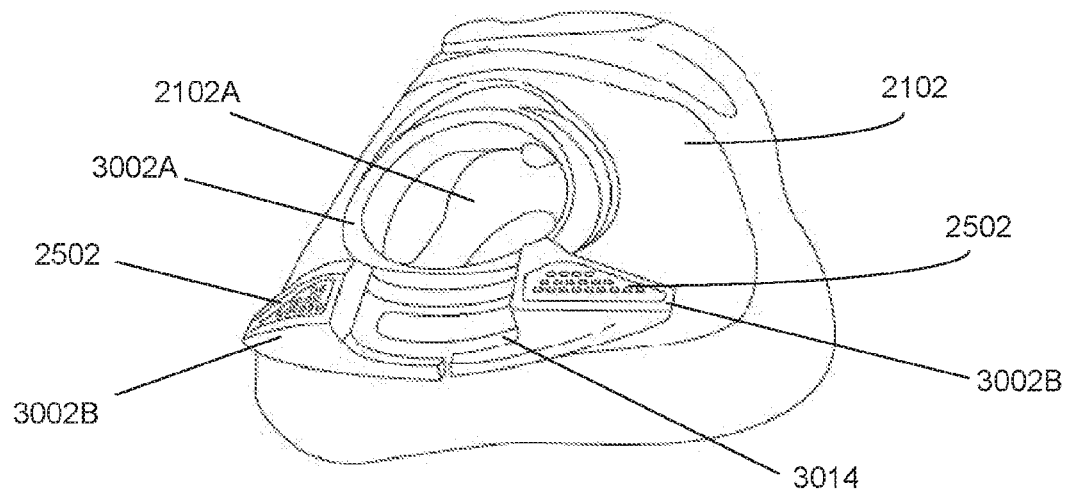

FIG. 73 is a perspective front view of the diffuser and mask seal of FIG. 72.

Figure 74:
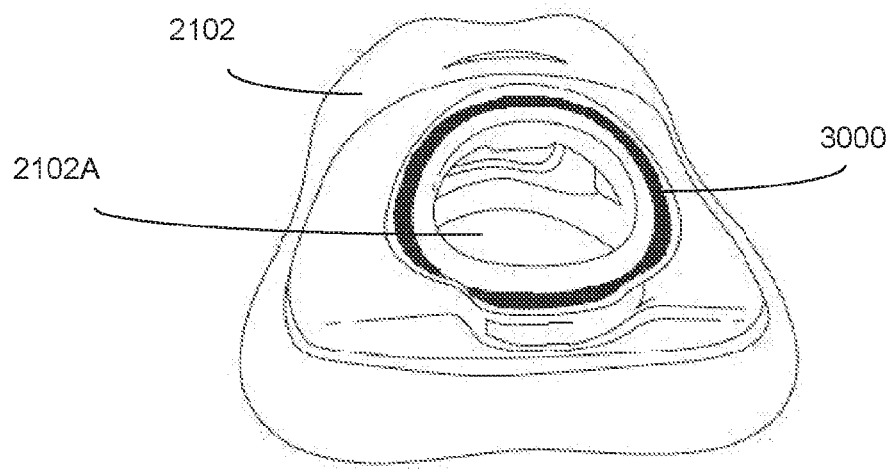

FIG. 74 is a perspective front view of another diffuser and mask seal.

Figure 75A:
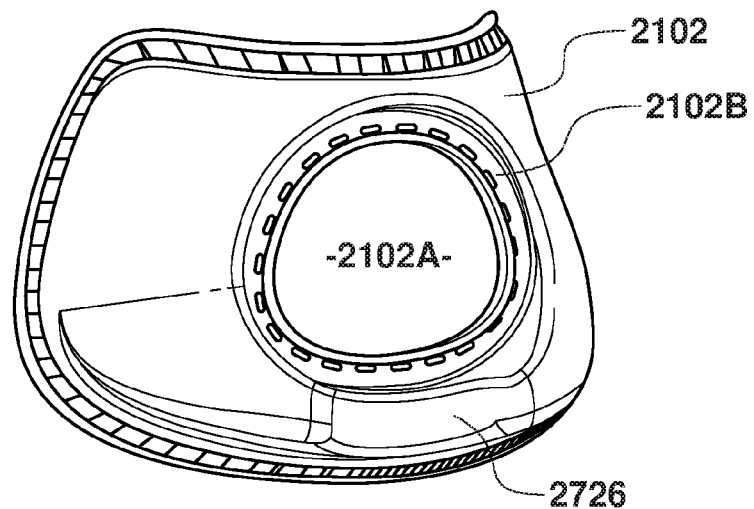
Figure 75B:
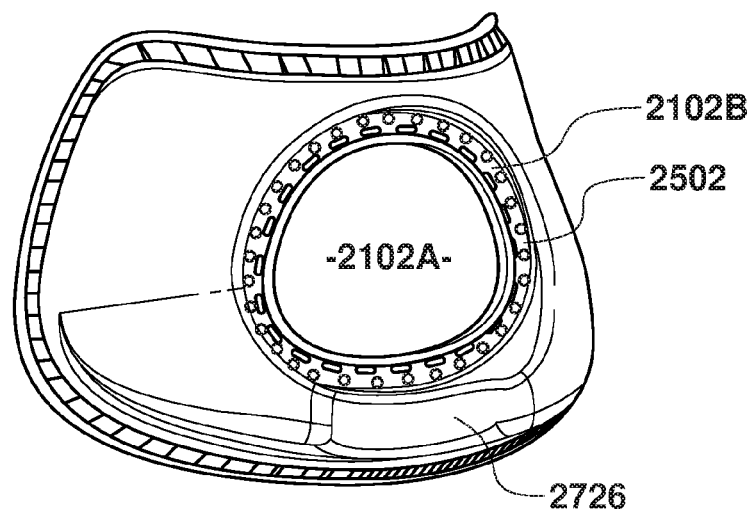

FIGS. 75a and 75b are front views of the mask seal of FIG. 74.

Figure 76:
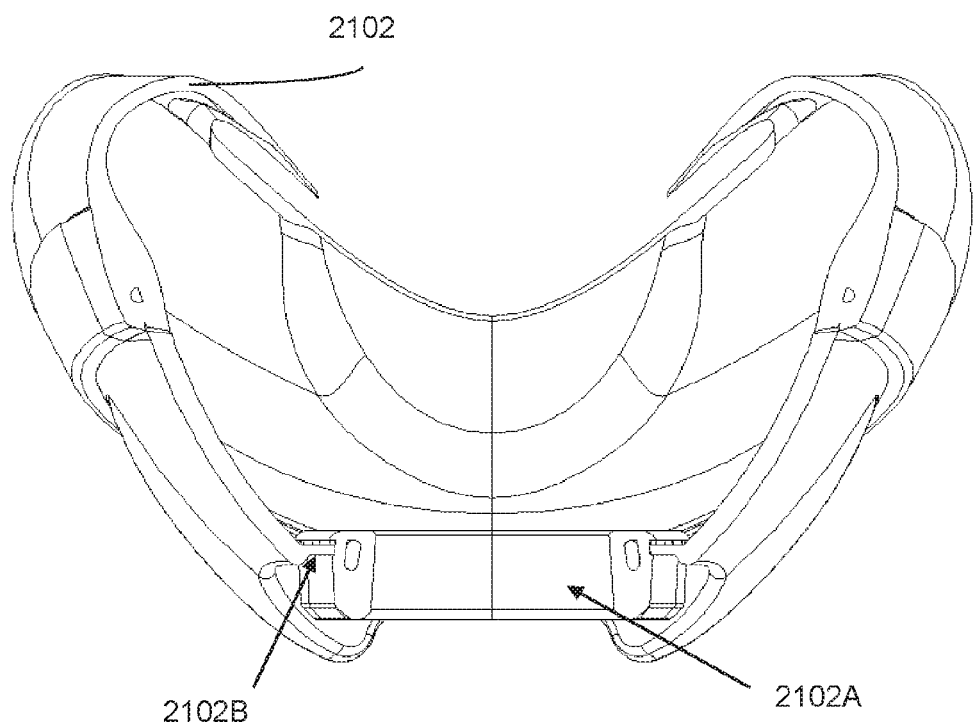

FIG. 76 is a cross sectional top view of the mask seal of FIG. 75.

Figure 77:
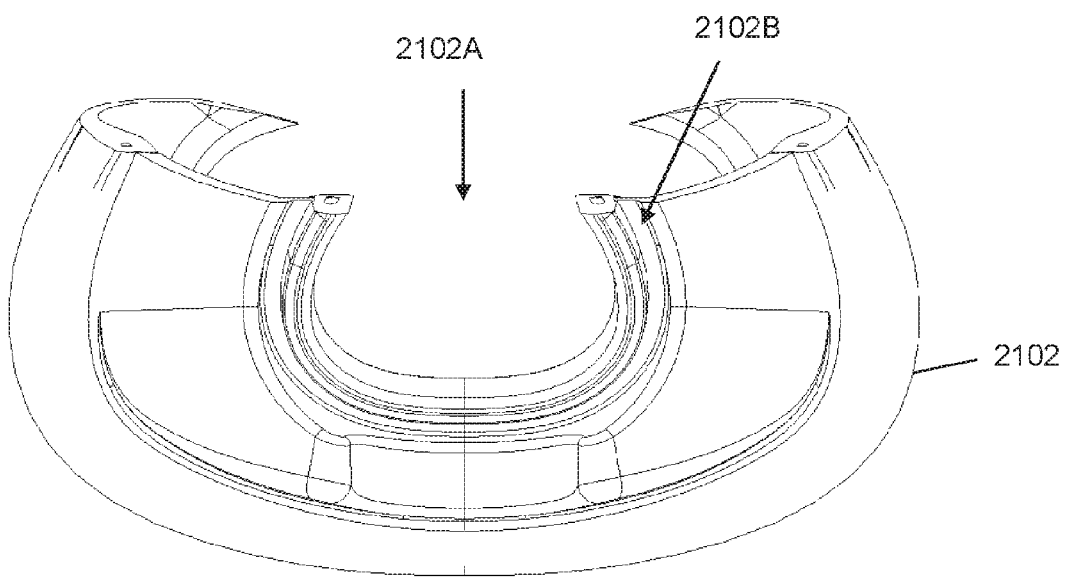

FIG. 77 is a cross sectional front view of the mask seal of FIG. 75.

Figure 78A:
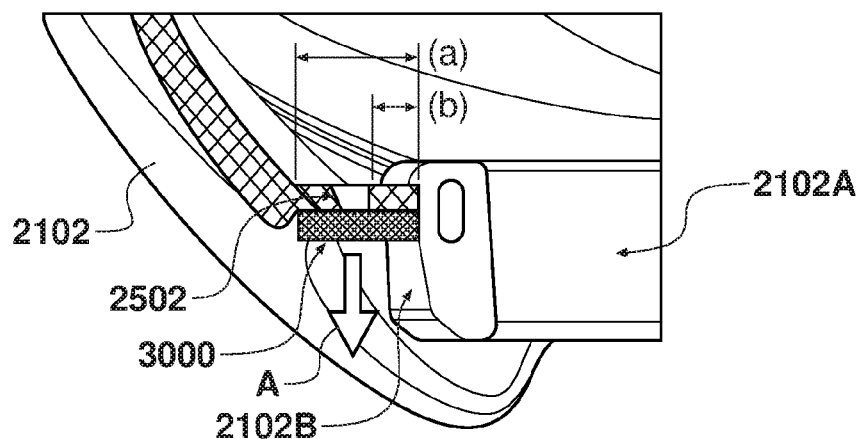
Figure 78B:
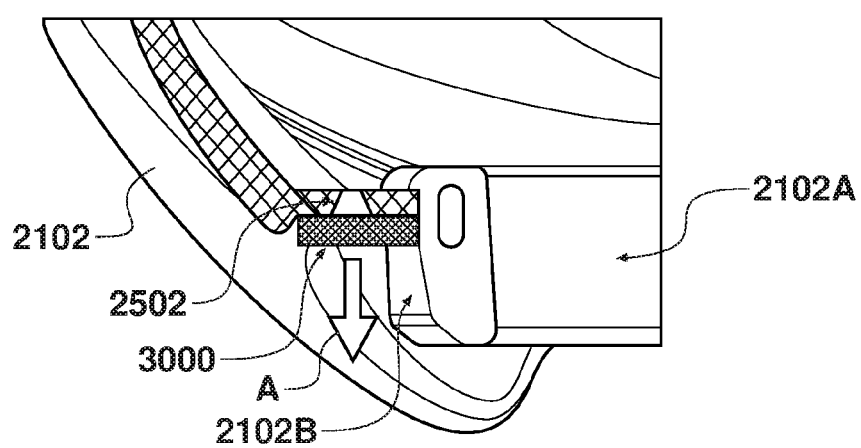

FIGS. 78a and 78b are enlarged cross sectional top views of the part of the mask seal of FIG. 75 shown in Box A of FIG. 76.

Figure 79A:
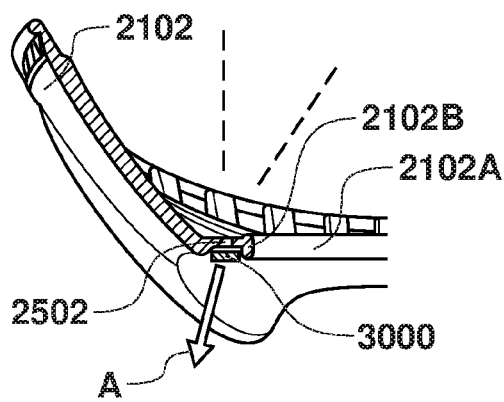
Figure 79B:
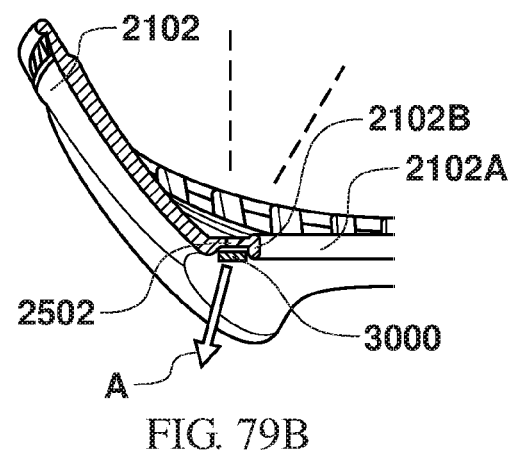
Figure 79C:
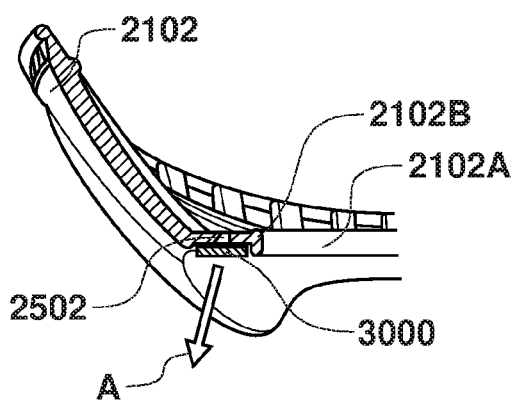
Figure 79D:
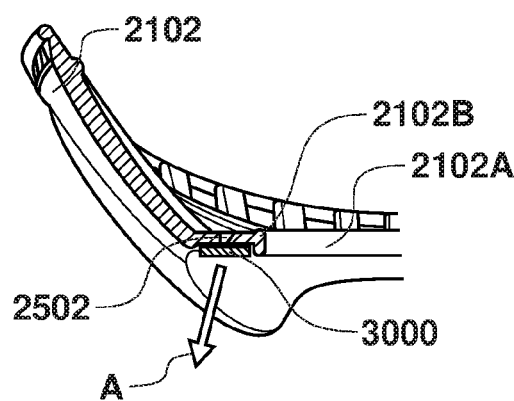

FIGS. 79a and 79b are enlarged cross sectional top views of the mask seal of FIG. 75, with first and second vent hole configurations, and FIGS. 79c and 79d are similar views but with a wider recess and diffuser.

Figure 80:
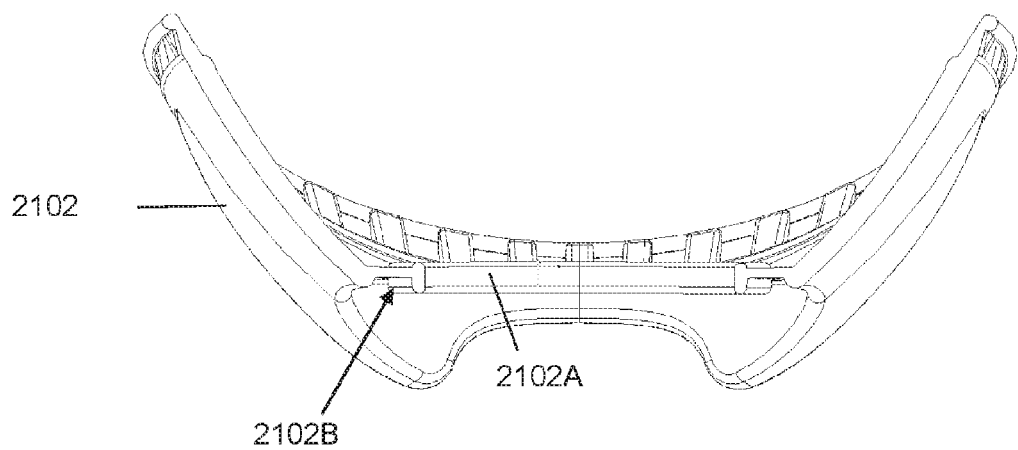

FIG. 80 is an enlarged cross sectional top views of the mask seal of FIG. 75.

Figure 81:
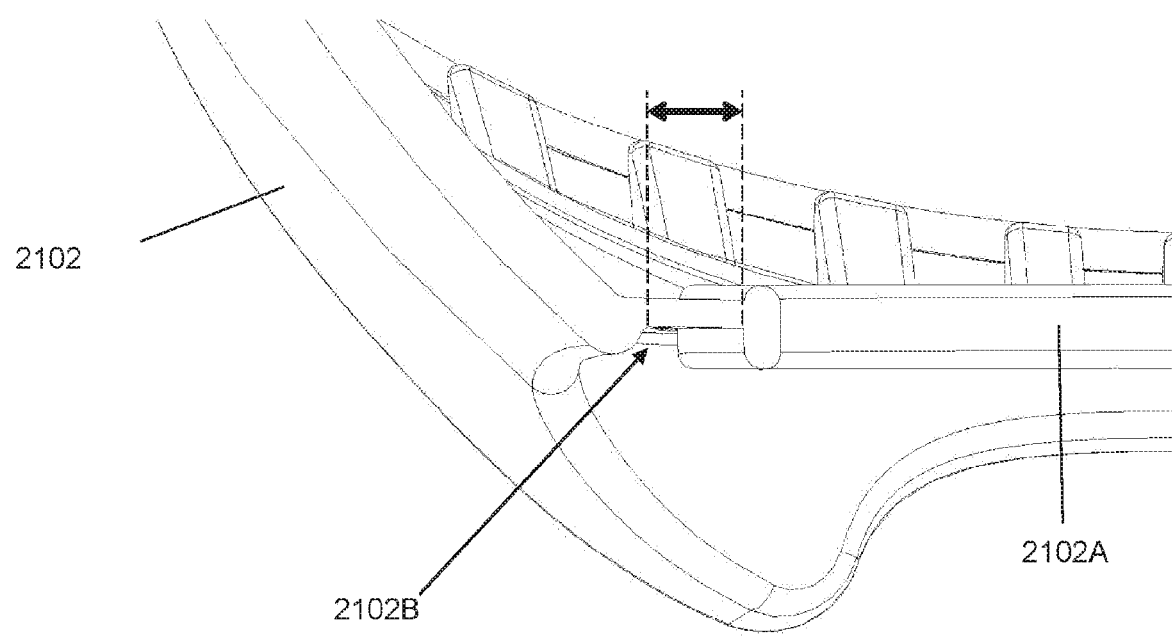

FIG. 81 is an enlarged cross sectional top view of the mask seal of FIG. 75.

Figure 82:
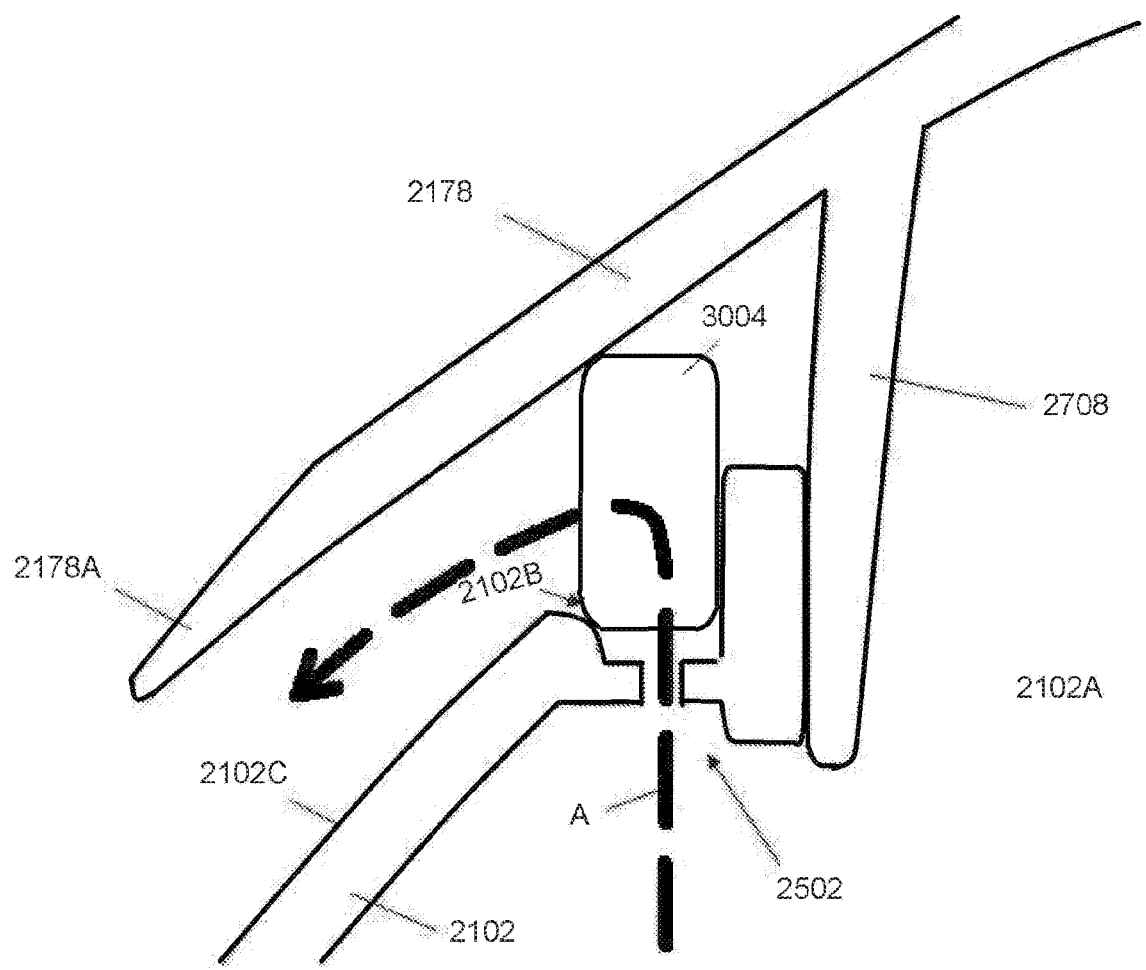

FIG. 82 are enlarged cross sectional side views of the mask seal of FIG. 87.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. For example, as the context may dictate, the terms "front" and/or forward can be used relative to components described herein positioned relatively or entirely distal to the user's face when the mask assembly as described herein is worn by the user. As the context may dictate, the terms "rear" and/or "back" can be used relative to components described herein positioned relatively or entirely proximal to the user's face and/or components that are forward or at the front of the mask assembly when the mask assembly as described herein is worn by the user. Moreover, terms such as "first," "second," "third," and so on may be used to describe separate components. Such terminology may include the words specifically mentioned above, derivatives thereof, and words of similar import.

One or more of the embodiments described herein address issues with sealing and fitting a variety of facial (e.g., nasal) geometries that can be experienced with face masks. In particular, at least some of the embodiments are directed toward patient interfaces, such as face masks, which seal below the bridge of the user's nose and around the nares. However, the embodiments disclosed herein could also be adapted to other full face masks (e.g., those that partially cover and/or seal on the bridge of the user's nose), or an under-nose nasal mask.

One or more of the embodiments described herein address issues with creating a satisfactory seal on a variety of facial geometries with an under-nose seal. The reduced foot print of an under-nose nasal or combined nasal and oral mask on the user's face compared to conventional nasal or full face masks that contact the nasal bridge can make it more difficult to maintain a seal with the user's face and be configured to adapt to various facial geometries. Sealing around and below the nose can present challenges due to the variation seen in facial geometries from user to user. One or more of the embodiments illustrated herein can allow for expansion of, for example, a nasal portion of the mask seal in response to fitment on a particular user or in response to pressure within the mask seal. In some configurations, the nasal portion of the mask seal can be configured to allow for relatively low resistance to an increase in width. Such an arrangement can allow a single mask seal to create a satisfactory seal with a user having a relatively narrow nose and a user having a relatively wide nose. For example, the width of the nasal portion may not expand or increase in width, or may expand or increase in width only slightly, when used with a user having a relatively narrow nose. The width of the nasal portion may expand or increase in width significantly or to a maximum extent when used with a user having a relatively wide nose. However, in at least some configurations, even when expanded, the nasal portion does not apply an uncomfortable level of force on the nose of the user. Such an arrangement advantageously can maintain a satisfactory seal between the user's face and the mask seal. An example of such an arrangement is disclosed in Applicant's PCT application No. PCT/IB2017/056146, the entirety of which is incorporated by reference herein.

FIGS. 1-28 illustrate a mask assembly 2100 and components thereof, both in position on a face of a user and separated from the face of the user. The illustrated mask assembly 2100 comprises a cushion module 2150, which is a combined nasal and oral cushion module, such that the mask assembly 2100 can be referred to herein as a nasal-oral or oro-nasal mask. The illustrated cushion module 2150 is designed to seal under the nose of the user, along a portion of the face extending lateral to the nose, as well as around the mouth of the user. The cushion module 2150 advantageously does not require contact with the bridge of the nose of the user. In the illustrated configuration, the cushion module 2150 does not extend over the bridge of the nose of the user. More particularly, the illustrated cushion module 2150 does not contact the bridge of the nose of the user. Even more particularly, the illustrated cushion module 2150 does not contact a forward-facing portion of the bridge of the nose of the user. In some configurations, the cushion module 2150 does not contact the face in a region vertically higher than a generally horizontal plane extending along the lower edges of the eyes of the user. The cushion module 2150 may or may not extend over the tip of the nose of the user. Thus, in some configurations, the cushion module 2150 covers the tip of the nose. In some configurations, the seal of the cushion module 2150 covers the tip of the nose. In some configurations, the illustrated cushion module 2150 preferably does not enshroud the tip of the nose of the user. In some configurations or with some facial geometries, the tip of the nose of the user extends over the adjoining portion of the cushion module 2150.

As illustrated, the cushion module 2150 preferably is adapted to extend around and seal over the wing or alar of the nose, which flares out to form a rounded eminence around the nostril. The illustrated cushion module 2150 is adapted to seal around the surfaces that define the opening to the nostril, which may include a portion or entirety of the fleshy external end of the nasal septum, sometimes called the columella. In some configurations, the cushion module 2150 is adapted to extend upwardly to seal along at least a portion of the left and right dorsal side walls of the nose of the user. In some configurations, the cushion module 2150 is adapted to extend upwardly along at least a portion of the left and right dorsal side walls without extending upwardly to the region of the bridge of the nose of the user. In some configurations, a first sealing surface of the cushion module 2150 contacts the underside of the nose of the user, possibly along with the upper lip and/or a transition region between the underside of the nose and the upper lip. A second sealing surface of the mask can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries. The cushion module 2150 preferably also seals around at least a portion of the user's mouth. The cushion module 2150 may or may not be adapted to seal between the mouth and nose of the user.

As illustrated, the cushion module 2150 comprises a support structure. In some configurations, the support structure is a mask shell or housing 2102. A mask seal or cushion 2104 can be attached to the housing 2102 such that the housing 2102 provides some amount of support for the mask seal 2104. However, in other configurations, the mask seal 2104 may not include a support and may be adapted for direct assembly to another component of the associated interface assembly. In some configurations, the housing 2102 can be substantially smaller than the illustrated housing 2102. For example, the housing 2102 can define an opening that allows the cushion module 2150 to be attached to another component, such as a frame and/or conduit connector (e.g., elbow) and the housing 2102 can be localized to the opening without providing direct support to other portions of the cushion module 2150.

The housing 2102 can be formed from any suitable material. In some configurations, the housing 2102 is formed from a relatively hard material. In some configurations, the housing 2102 is formed from a hard plastic material, such as a polycarbonate material. In some configurations, the mask assembly 2100 can comprise a mask seal that includes a mask seal clip that is separate from but attachable to a housing. In such a configuration, the mask seal clip would connect the mask seal 2104 to the housing 2102. In such configurations, the mask seal and mask seal clip can be formed separately and secured together or the mask seal and the mask seal clip can be integrated into a single component. In some configurations, the mask seal can be over-moulded onto the mask seal clip and, in some configurations, the mask seal 2104 can be over-moulded directly onto the housing 2102, which can comprise chemical and/or mechanical over-moulding, for example.

In some configurations, the housing 2102 comprises a substantial portion of a forward wall of the cushion module 2150. Such an arrangement provides an advantageous level of support to the mask seal 2104. For example, the housing 2102 comprises a substantial portion of an oral portion of the forward wall of the cushion module 2150 or mask assembly 2100. In some configurations, the housing 2102 is generally limited to the oral portion of the cushion module 2150 or mask assembly 2100 and does not extend into the nasal portion of the cushion module 2150 or mask assembly 2100, at least to any significant extent. Such an arrangement can provide support to the mask seal 2104, while advantageously permitting movement or deformation of the nasal portion of the mask seal 2104. In other arrangements, the housing 2102 can extend into the nasal portion to provide additional support to the nasal portion, if desired.

The mask seal 2104 is designed to seal against the face of the user. The mask seal 2104 preferably is formed of a soft material, such as silicone, for example but without limitation. In some configurations, at least portions of the mask seal 2104 can be textured to improve comfort for the user. For example, in some configurations, at least portions of the mould used to form the illustrated mask seal 2104 can be bead blasted to provide a surface texture in at least the regions of the mask seal 2104 that will contact the skin of the user. Other techniques for texturing one or more surface of the mask seal 2104 can be used. In some configurations, it may be desirable to avoid surface texturing and provide at least the face-contacting surfaces of the mask seal 2104 with a smooth surface texture, which may increase grip of the mask seal 2104 on the user's face and improve sealing characteristics.

The cushion module 2150 can be engaged with or otherwise supported by a headgear connector or frame 2178 that allows for connection to a head strap or headgear 2180 of any suitable arrangement. Thus, the frame 2178 can be considered as a component of the mask assembly 2100. The mask assembly 2100 may also include an inlet tube, such as a gas supply conduit 2520A, connected to the frame 2178, among other possible components. The cushion module 2150 can be keyed to the frame 2178 to permit assembly in only the correct orientation. The headgear assembly 2180 can include straps, such as one or more upper side straps 2804, one or more lower side straps 2802, and/or a crown strap 2808, among other components (see FIGS. 25-27). In some configurations, the head strap or headgear 2180 could be coupled directly to the cushion module 2150 and the frame 2178 can be utilized for other purposes or omitted. In such arrangements, the head strap or headgear 2180 could be coupled to the housing 2102. Together, the frame 2178 and the headgear 2180 can support the cushion module 2150 in place on the user's face. Collectively, the cushion module 2150, the frame 2178, gas supply conduit 2520A and the headgear 2180 can be referred to as an interface assembly. Although the illustrated mask assembly 2100 includes the cushion module 2150 that supports the seal 2104 and the frame 2178 that connects to the headgear 2180, in other configurations a single integrated structure could both support the seal 2104 and connect to the headgear 2180. For example, the housing 2102 of the cushion module 2150 and the frame 2178 could be formed as an integrated structure, which could be simplified relative to the illustrated arrangement. Such a single integrated structure is often referred to as a "frame." Thus, references to the separate cushion module 2150/housing 2102 and frame 2178 in this disclosure could also refer to an integrated structure, unless indicated otherwise.

As shown in the illustrated example and as explained in more detail below, the frame 2178 can include an anti-asphyxia (A-A) valve assembly 2522 (referred to herein as the "A-A valve 2522"). In some configurations, the A-A valve 2522 can be received by the valve recess 2726 of the cushion module 2150, as discussed below. As described in more detail below, the A-A valve 2522 can include a valve housing. The A-A valve 2522 can be integrally formed with the frame 2178. As described below, the A-A valve 2522 can include at least a portion of the frame 2178, a valve element or valve member, such as a valve flap 2524, and/or a tube connector 2711, among other possible components. The A-A valve 2522 can be located within the frame 2178 adjacent the air supply conduit 2520A. In some embodiments, the A-A valve 2522 can include an inlet tube positioned rearward of the front wall of the frame 2178. In some embodiments, the inlet tube can define at least a portion of a gas flow passage. In some configurations, the integration of the A-A valve 2522 with the frame 2178 can allow the air supply conduit 2520A to extend in a generally downward direction from a lower front portion of the frame 2178. Such configurations can reduce the overall bulkiness of the patient interface. For example, in such configurations, the conduit 2520A can be positioned closer to the user in use. The gas flow passage is provided by the gas supply conduit 2520A, the A-A valve 2522 and the cushion connector 2708. The gas flow passage provides a passage through which pressurized gas is delivered to the user's nose and/or mouth via the mask assembly 2100.

FIGS. 2A-2B illustrate an example of the mask assembly 2100. As mentioned above, the cushion module 2150 of the mask assembly 2100 can include the mask seal 2104 and housing 2102, and is assembled to the frame 2178 and/or the air supply conduit 2520A, among other components. The frame 2178 can be generally curved in a lateral and/or a vertical direction.

In some embodiments, the frame 2178 can be provided to a front side of the cushion module 2150. In some embodiments, the frame 2178 can cover a substantial portion of the front side of the cushion module 2150, such as a substantial portion of a housing 2102 of the cushion module 2150. In some embodiments, the frame 2178 is centered in the lateral direction along the front surface of the cushion module 2150. For example, the entire front surface of the frame 2178 can be positioned forward of the cushion module 2150.

FIGS. 3A-11 illustrate an embodiment of the frame 2178. In some embodiments, the frame 2178 can include a cushion connector 2708, an inlet or inlet opening 2706, the valve 2522, at least one upper strap connector 2702, at least one lower strap connector 2704, and/or upwardly extending supports 2179. The upwardly extending supports may be referred to as wings or paddles.

In some embodiments, the cushion connector 2708 can be positioned on a rear side of the frame 2178. In some embodiments, the cushion connector 2708 is unitary with the frame 2178 and extends rearwardly from a rear surface of a front wall 2701 of the frame 2178. The cushion connector 2708 can provide a fluid connection between the inlet 2706 and the cushion module 2150.

In some embodiments, the cushion connector 2708 can be shaped to fit into at least a portion of the cushion module 2150 to connect the frame 2178 to the cushion module 2150. For example, the cushion connector 2708 can fit into at least a receiving portion of the mask housing 2102, such as a frame connector 2730. The cushion connector 2708 can include a somewhat rounded 'D' shape, a rounded trapezoidal shape, circular shape, elliptical shape and/or oval shape, among other possible shapes.

In some embodiments, the cushion connector 2708 is in the form of a protruding wall that forms a cuff or collar. The protruding wall can extend rearwardly and/or upwardly from the rear side of a front wall portion 2701 of the frame 2178. The cushion connector 2708 can be positioned above the A-A valve 2522 along the rear side of the frame 2178. The cushion connector 2708 can be positioned adjacent the A-A valve 2522 along the rear side of the frame 2178. In some configurations, the inlet 2706, the A-A valve 2522 and the cushion connector 2708 cooperate to form a gases flow passage defined by the frame 2178. In the illustrated arrangement, each of the inlet 2706, the A-A valve 2522 and the cushion connector 2708 includes a substantially enclosed space (e.g., with the exception of specific and deliberate openings) that defines a portion of the overall gases flow passage. In some configurations, the front wall portion 2701 of the frame 2178 defines at least a portion of the gases flow passage. In the illustrated arrangement, the front wall portion 2701 of the frame 2178 defines a portion of the gases flow passage in one or both of the A-A valve 2522 and the cushion connector 2708. Such an arrangement allows the frame 2178 to have a reduced depth in comparison to designs in which an entirety of the gases flow passage is defined by dedicated structure.

In some embodiments, the cushion connector 2708 can include an alignment feature, such as an alignment notch 2710. The alignment notch 2710 can be formed in a portion of the cushion connector 2710. For example, the alignment notch 2710 can be formed in an upper wall portion of the cushion connector 2708. The alignment notch 2710 can guide the connection between the frame 2178 and the mask assembly 2100. For example, the alignment notch 2710 can correspond to a feature on the mask assembly 2100 to allow the frame 2178 and the mask assembly 2100 to be connected in a proper orientation. In some embodiments, the alignment notch 2710 has a generally trapezoidal shape, rectangular shape, and/or square shape, among other possible shapes. In some embodiments, the alignment notch 2710 can have a width at a rearward edge of the upper wall of the cushion connector 2708 that is wider than a width of the alignment notch 2710 at a position closer to the rear side of the frame 2178.

In some embodiments, the frame 2178 can carry or otherwise include the inlet 2706. The inlet 2706 can be defined by a tube connector 2711, which can be a separate structure that is coupled to the frame 2178. In some embodiments, the inlet 2706 can provide a fluid flow path or gases flow passage through which pressurized air can be provided to the mask assembly 2100. In some embodiments, the pressurized air can be provided to the mask assembly 2100 through the inlet 2706 via the A-A valve 2522 or past the A-A valve 2522. As explained in more detail below, the A-A valve 2522 can provide access to atmospheric air when there is no pressurized air source or when the pressure within the mask assembly 2100 otherwise drops below atmospheric pressure.

In some embodiments, the frame 2178 can include at least one upper strap connector 2702 and at least one lower strap connector 2704. In the illustrated arrangement, the frame 2178 includes a pair of upper strap connectors 2702 and a pair of lower strap connectors 2704. Each of the pair of the upper and lower strap connectors 2702, 2704 can be positioned on opposite lateral sides of the frame 2178. In some embodiments, the upper strap connectors 2702 can slidably receive the corresponding upper headgear straps 2804 of the headgear 2180 (e.g., see FIG. 1). With reference to FIG. 4, the upper headgear connectors 2702 can include a post 2703A and an aperture 2703B. The post 2703A can be spaced away from a front surface of the frame 2178. The post 2703A can be positioned at approximately a center of the aperture 2703B. In some embodiments, the post 2703A can be positioned offset from the center of the aperture 2703B. In some embodiments, the post 2703A can be offset forward of a front wall of the frame 2178.

Figure 1:
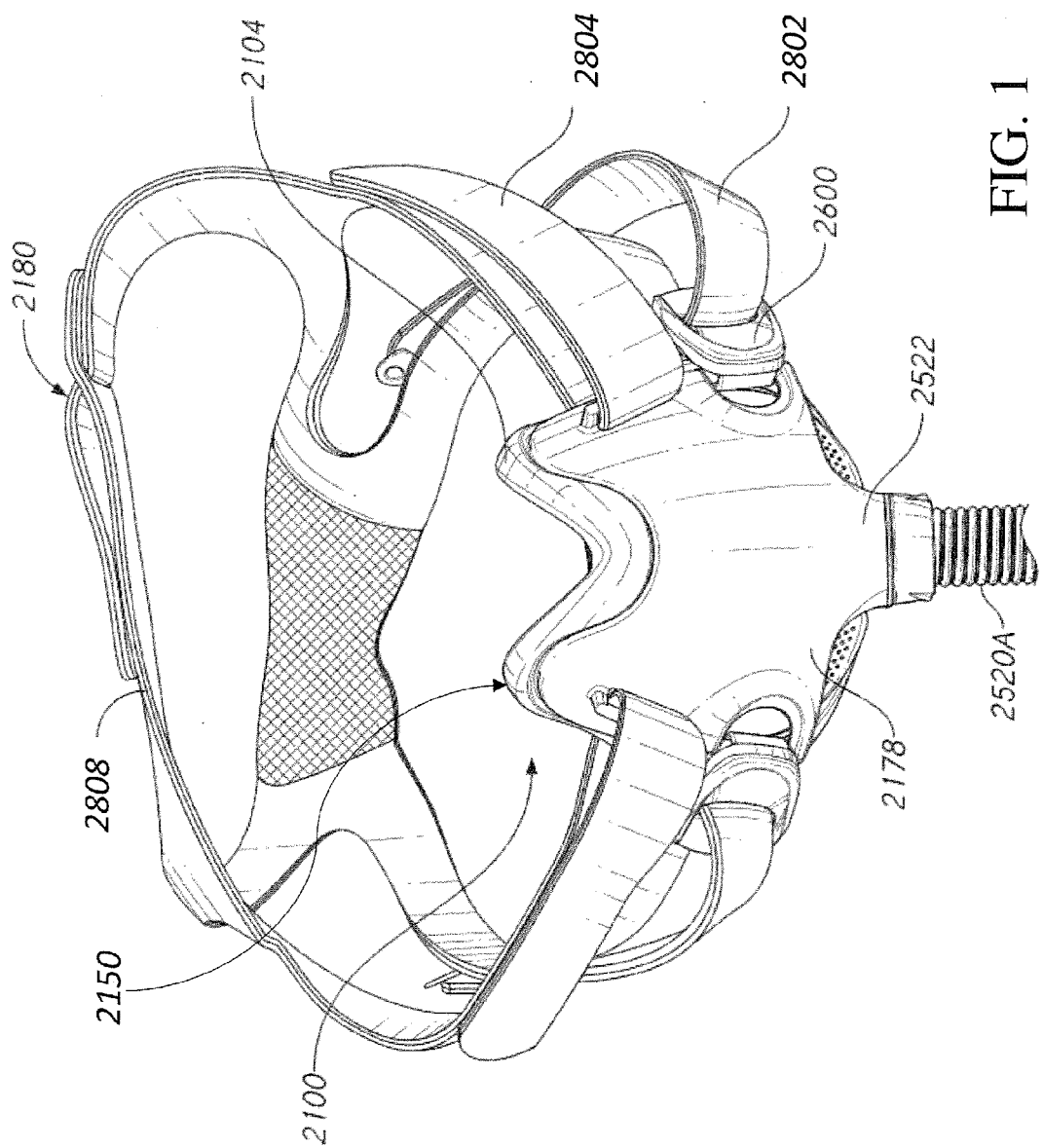
FIG. 1 is a front and top perspective view of a mask assembly.
Figure 28:
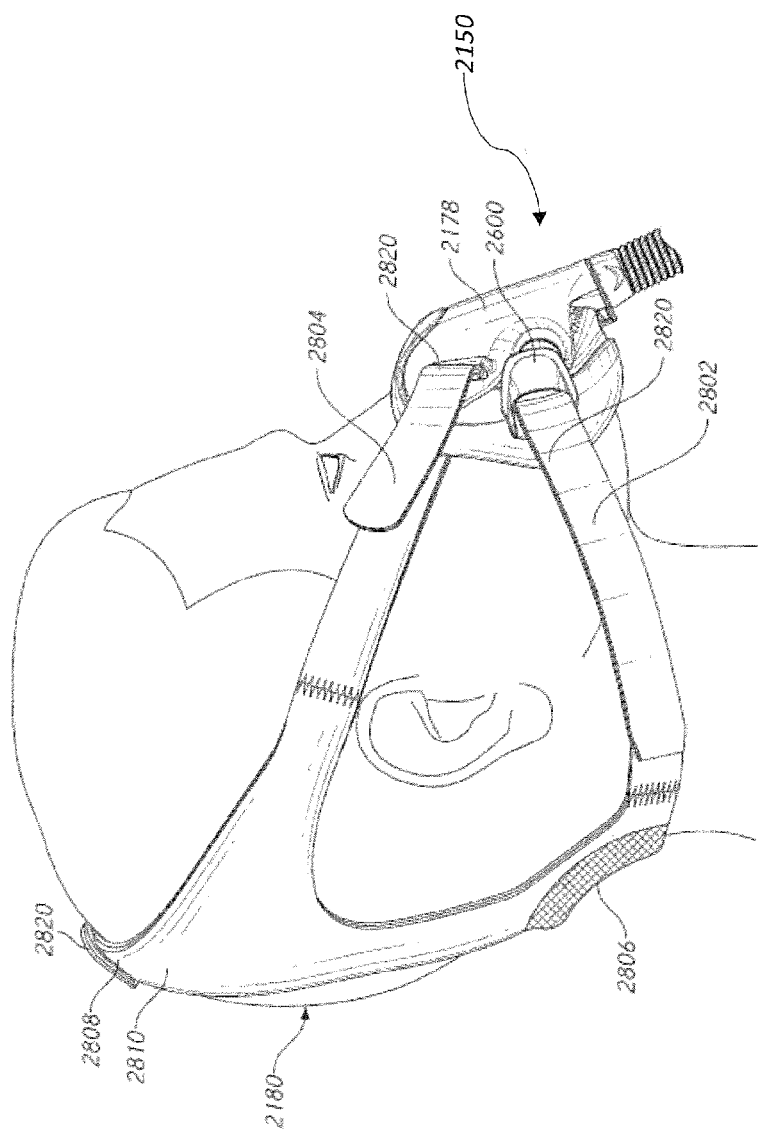
FIG. 28 is a side view of an interface assembly showing a headgear assembly.

As shown in at least FIGS. 1 and 28, the post 2703A can help to secure the upper side strap 2804 to the upper headgear connector 2702. In some embodiments, the post 2703A together with the front surface of the frame 2178 can define a slot through which the corresponding upper side strap 2804 can pass. For example, the upper side strap 2804 can pass through the slot formed between the post 2703A and the aperture 2703B. Once the upper side strap 2804 passes through the slot, the upper side strap 2804 can be wrapped around an outer side of the post 2703A and folded over on itself, for example. In some embodiments, the aperture 2703B can provide additional space to allow the upper side strap 2804 to pass behind the post 2703A. In some configurations, the aperture 2703B can help to decrease a distance between the post 2703A and the front surface of the frame 2178 necessary to accommodate the thickness of the strap 2804. In some embodiments, the upper strap connectors 2702 can secure, such as removably secure, a headgear clip that can be attached to the upper side straps 2804.

In some embodiments, the lower strap connector 2704 can receive and/or secure the lower side strap 2802 and/or a lower headgear clip 2600 (see FIG. 1). As identified in FIG. 4, the lower strap connector 2704 can include a lower post 2705A. The lower post 2705A can be positioned along a side edge of the frame 2178. The lower post 2705A can be spaced away from a portion of the frame 2178 to define an aperture 2705B. In some embodiments, the lower post 2705A forms a lower lateral edge of the frame 2178. In some embodiments, the aperture 2705B can be shaped to receive at least a portion of the lower headgear clip 2600. In some embodiments, the aperture 2705B can be substantially D-shaped, among other possible shapes. In some embodiments, the post 2705A can be received within and/or retain a portion of the corresponding lower headgear clip 2600, such as a hook portion of the clip 2600. The aperture 2705B may be sized and shaped to accommodate the hook portion of the clip 2600. The lower post 2705A can provide a removable connection between the lower side straps 2804 and the frame 2178 and/or the lower headgear clips 2600 and the frame 2178.

In some embodiments, the frame 2178 can include the upwardly extending supports 2179. The upwardly extending supports 2179 extend upwardly from opposite sides of a central portion of the frame 2178. The upwardly extending supports may be referred to as "frame paddles." As described above, the upwardly extending supports 2179 can define upper support members that provide support to forward facing lateral sides (upwardly extending portions 2126 of the seal 2104) of a nasal region 2168 of the mask seal 2104 when assembled. The upwardly extending supports 2179 can help to minimize deflection of the mask seal 2104. In some embodiments, the upwardly extending supports 2179 can help to maintain contact between the nasal region 2168 and the user's nose. For example, the upwardly extending supports 2179 can help to prevent the nasal region 2168 and the upwardly extending portions 2126 of the mask seal 2104 from inflating away from and/or disengaging from the user's nose while allowing an internal wall of the upwardly extending portions 2126 to deflect outwardly. The upwardly extending supports 2179 each have curved upper edges. The upwardly extending supports 2179 each form semi-circular or D-shaped panels. The panels are located below and to either side of the wearer's nose in use. A curved trough is formed in the upper edge of the frame 2178 between the upwardly extending supports 2179.

FIGS. 4-10 illustrate certain portions of the valve 2522 in greater detail. As shown in at least FIGS. 4-6, 9 and 10, the valve 2522 can include a valve element or valve member, such as a valve flap 2524. The valve 2522 can also include a tube connector 2711, among other possible components. In some embodiments, the valve 2522 can include vent paths 2722 and/or outlets 2720. As illustrated, at least a portion or some components of the valve 2522 can be integrally formed with the frame 2178. For example, the body portions that define the gases flow passage(s) of the valve 2522 are integrally formed with the frame 2178. Some configurations can desirably reduce assembly time and/or reduce the number of components necessary to manufacture, clean and/or replace. Some such configurations can desirably reduce the likelihood that pressurized air will leak from the assembly.

Figure 7:
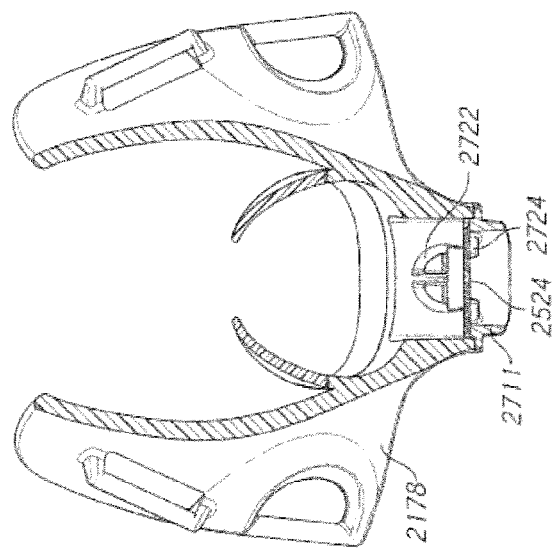
FIG. 7 is a front cross-sectional view of the frame of the mask assembly of FIG. 3A taken along the line 7-7 of FIG. 4.
Figure 8:
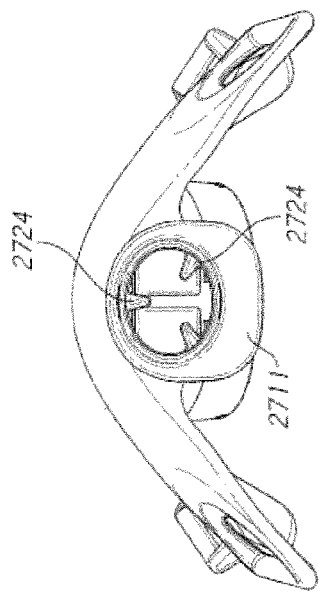
FIG. 8 is a bottom view of the frame of the mask assembly of FIG. 2A.

FIG. 5 and FIG. 6 illustrate side cross-sectional views of the frame 2178 along the lines 5-5 and 6-6 shown in FIG. 3A, respectively. FIG. 7 illustrates a front cross-sectional view of the frame 2178 along the line 7-7 shown in FIG. 4. As illustrated, the frame 2178 can house the valve flap 2524. In some embodiments, the frame 2178 entirely surrounds a perimeter of a movable portion of the valve flap 2524. As such, the movable portion of the valve flap 2524 can be positioned to fit within a gases flow passage of the valve 2522 of the frame 2178.

In some embodiments, the tube connector 2711 can define the inlet opening 2706 that directs pressurized air through the valve 2522 to the user through the mask assembly 2100. In some embodiments, the tube connector 2711 can be elliptical shaped, circular shaped, and/or oval shaped, among other shapes. Preferably, a dimension of the inlet 2706 in a forward-rearward direction is smaller than a dimension of the inlet 2706 in a lateral direction. Accordingly, extra space is provided to accommodate the valve 2522 in a forward-rearward direction in comparison to a design in which the inlet 2706 is circular, without increasing the forward-rearward dimension of the frame 2178 or moving the inlet 2706 further away from the user's face.

The tube connector 2711 can include a male component that is received by a corresponding female connector. The female connector may be attached to the conduit 2520A. In some embodiments, the tube connector 2711 can allow for disconnection of the conduit 2520A by twisting the conduit 2520A relative to the frame 2178 and/or the tube connector 2711. In some embodiments, the conduit 2520A is connected to the tube connector 2711 by a snap-fit configuration, among other possible configurations. For example, the tube connector 2711 can include one or more tube connector notches 2712. The tube connector notches 2712 can engage corresponding features on the conduit 2520A via the snap-fit configuration.

In some embodiments, the valve flap 2524 can be secured within the frame 2178 by the tube connector 2711. In some embodiments, the tube connector 2711 can be permanently connected to a lower end of the frame 2178 that defines the valve 2522 by various configurations, such as welding, adhesive, and/or a snap-fit configuration, among other possible configurations. In some embodiments, the tube connector 2711 can surround and/or secure a tab of the valve flap 2524 between the lower end of the frame 2178 and a flange of the tube connector 2711. In some embodiments, the valve flap 2524 can be positioned adjacent an inner end of the tube connector 2711 within the frame 2178. In some embodiments, the valve flap 2524 can be constructed in whole or in part from a flexible elastomer, such as silicone, among other materials.

The valve flap 2524 can open and close different flow paths within the valve 2522 to allow air to flow through a desired one of the different flow paths of the valve 2522. For example, when a flow generator supplies positive pressure air to the user through the mask assembly 2100, the valve flap 2524 can pivot about a hinge or otherwise move in response to the pressurized air entering the inlet 2706. In this position, the valve flap 2524 is opened relative to the inlet 2706 of the tube connector 2711, and is closed relative to the valve 2522 and/or vent paths 2722 of the valve 2522. Some configurations can help to ensure that all or substantially all of the positive pressure airflow is directed to the user with little to no airflow leaking from the vent paths 2722 of the valve 2522. When a flow generator does not provide airflow to the mask assembly 2100 or the pressure within the mask assembly 2100 otherwise drops below atmospheric pressure, the valve flap 2524 closes relative to the inlet 2706 of the tube connector 2711 and the vent paths 2722 of the A-A valve 2522 are opened to allow the user in inhale ambient air through the valve 2522.

The tube connector 2711 can support the valve flap 2524 in an operable position relative to the valve 2522 portion of the frame 2178. In some configurations, the tube connector 2711 defines a stop that prevents the valve flap 2524 from inverting or extending downwardly out of the inlet 2706 of the frame 2178 (see, e.g. FIG. 5). In some configurations, the tube connector 2711 can include a flap support 2724. In some embodiments, the tube connector 2711 can include at least three flap supports 2724 (see FIG. 8). In some embodiments, the tube connector 2711 can includes at least two, three, four, five, or six or more flap supports 2724. The flap supports 2724 can extend radially inwardly from an inner surface of a perimeter wall of the tube connector 2711 into the inlet 2706 of the tube connector 2711. In some embodiments, the flap supports 2724 can be positioned adjacent an upper edge of the tube connector 2711. In some configurations, the flap supports 2724 can prevent the valve flap 2524 from inverting or extending downwardly into the inlet 2706.

As shown in at least FIG. 7, the valve 2522 (alone, or in combination with the frame 2178) can include various vent paths and valve outlets to allow air to flow in and out of the mask assembly 2100 when the valve flap 2524 is in the closed position. For example, in some embodiments, a flow path is provided through the vent paths 2722 and valve outlets 2720 of the valve assembly 2522. In some embodiments, the valve 2522 can include at least two vent paths 2722 and/or at least two lateral valve outlets 2720.

Figure 11:
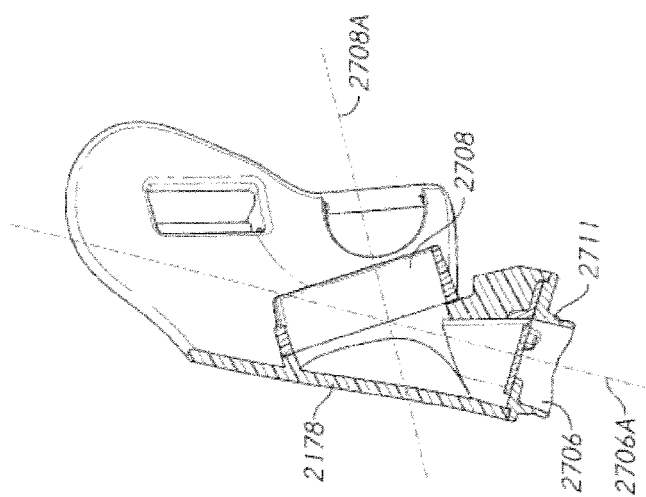
FIG. 11 is a side cross-sectional view of the frame of the mask assembly of FIG. 2A showing an inlet axis and a cushion connector axis.

In some embodiments, the vent paths 2722 can extend rearwardly away from the inlet 2706 towards the outlets 2720. In some embodiments, the vent paths 2722 can extend through an internal wall of the valve 2522 towards the outlets 2720. In some embodiments, the vent paths 2722 can extend through an internal wall of the valve 2522 towards the outlets 2720. In some embodiments, the vent paths 2722 can extend rearwardly and downwardly into the outlets 2720. In some embodiments, a central axis of the vent paths 2722 forms an acute angle with the central axis 2706A (as shown in FIG. 11) of the inlet 2706.

In some embodiments, the outlets 2720 can define an opening to allow exhausted air to pass out of the patient interface or inhaled air to enter the patient interface, via the vent paths 2722 when the valve flap 2524 is in the closed position relative to the inlet 2706. As shown in FIG. 6, the valve 2522 can include a rear wall 2523 that is spaced rearwardly away from an outlet of the vent paths 2722 on the side of the outlets 2720 and defines a rearward extend of the outlets 2720. Such configurations can provide a space to direct the exhausted air in a lateral direction, as indicated by arrows shown in FIG. 3B. The rear wall 2523 of the valve 2522 can allow the exhausted air to be directed away from the user. In some embodiments, exhausting the air in the lateral direction can help to minimize contact between the exhausted air and the user. Some configurations can help to reduce discomfort caused to the patient by the exhausted air. In some embodiments, the outlets 2720 can extend below a lower surface of the housing 2102 of the cushion module 2150 when assembled (see FIGS. 23 and 24). In such configurations, the exhausted air may not be blocked by the housing 2102.

FIGS. 9 and 10 illustrate exploded views of the frame 2178 showing portions of the valve 2522. In some embodiments, the valve flap 2524 can include an outer perimeter 2524A and an interior rib 2524B. The outer perimeter 2524A can include a lip. The lip can define a thickened region that extends along the outer perimeter 2524A. In some embodiments, the rib 2524B can be positioned along a lower side of the valve flap 2524. The rib 2524B can be positioned approximately along a central axis of the valve flap 2524. In some embodiments, the rib 2524B can define a thickened region along the center of the valve flap 2524. In some embodiments, the outer perimeter 2524A and/or the rib 2524B can provide rigidity to the valve flap 2524. The outer perimeter 2524A and/or the rib 2524B can help to inhibit ballooning and/or deformation of the valve flap 2524 caused by the pressurized airflow in use. Some configurations can help to provide an effective seal around the vent paths 2722 when the valve 2522 is in the opened position relative to the inlet 2706.

In some embodiments, the tube connector 2711 can define the inlet 2706 that directs a source of pressurized air through the valve 2522 into the breathing chamber of the cushion module 2150. The inlet 2706 can be angled downwards in use. For example, as shown in FIG. 11, a central axis 2706A of the inlet 2706 can form an angle with a central axis 2708A of the cushion connector 2708. In some embodiments, the angle is approximately 125 degrees. In some embodiments, the angle is greater than or less than 125 degrees. In some embodiments, the angle is approximately 124.4 degrees. In some embodiments, the angle is greater than or less than 124.4 degrees. Some configurations can help to keep the conduit 2520A away from the user. Some configurations can desirably minimize the bulkiness of the patient interface, such as at the front of the mask assembly 2100.

Figure 12:
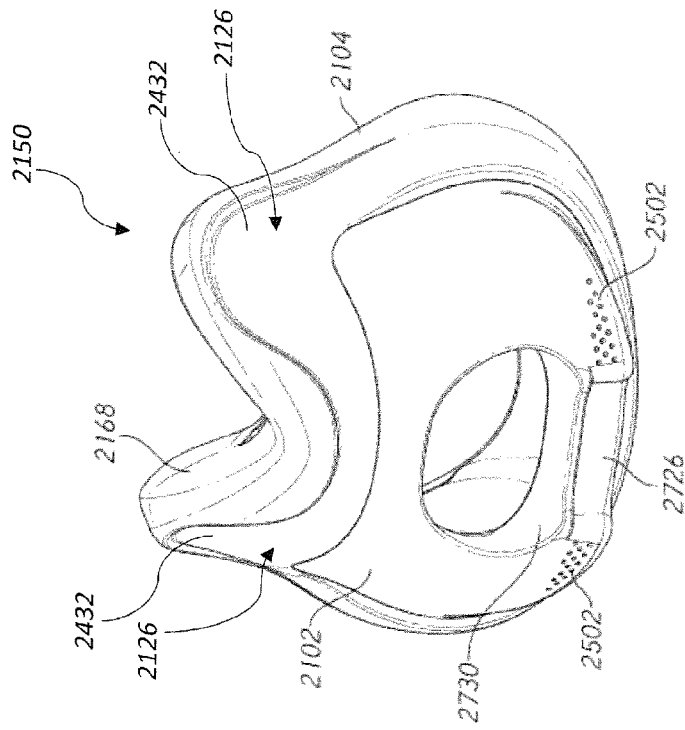
FIG. 12 is a front, top and side perspective view of a cushion module of the mask assembly of FIG. 2A.
Figures 13, 14:
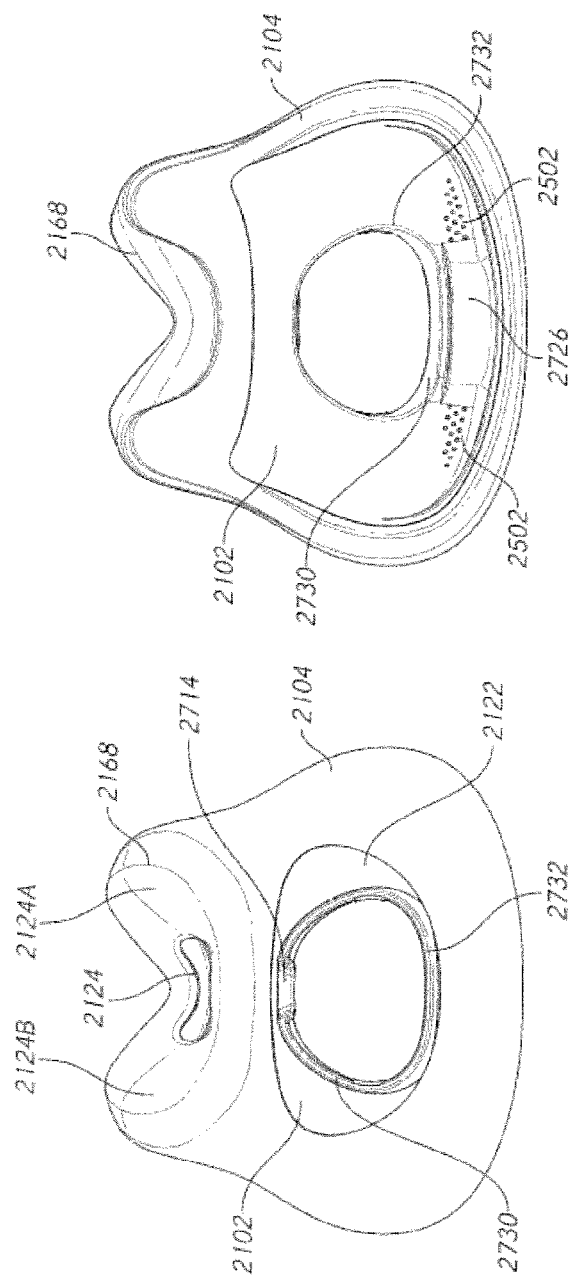
FIG. 13 is a rear view of the cushion module of the mask assembly of FIG. 2A.
FIG. 14 is a front view of the cushion module of the mask assembly of FIG. 2A.

FIGS. 12 and 14 illustrate a front of the cushion module 2150 showing the housing 2102. In some embodiments, the housing 2102 can include one, two, three, four, or five, or more bias vents 2502. The bias vents 2502 can be positioned at a bottom region of the housing 2102. In some embodiments, the bias vents 2502 can be positioned on a generally forward facing surface of the housing 2102. For example, the bias vents 2502 can be positioned adjacent a lower edge of the housing 2102. In some configurations, holes of the bias vents 2502 can be positioned close to and/or adjacent the lower edge of the frame 2178 when assembled. Preferably, the bias vents 2502 are positioned below a lower edge of the frame 2178. Such configurations can minimize contact between vented air and the frame 2178. Such configurations can help to reduce noise and/or undesirable drafts or air leaks.

FIG. 14 shows an example of the housing 2102 including two bias vents 2502. The bias vents 2502 can include a plurality of holes. The plurality of holes can be arranged in a generally triangular pattern, among other possible patterns. The bias vents 2502 can be positioned on opposing lateral sides of an inlet 2732 and/or valve recess 2726 of the cushion module 2150. In some embodiments, at least a portion of the bias vents 2502 is positioned below at least a portion of the inlet 2732 and at least a portion of the bias vents 2502 is positioned beyond a side of the inlet 2732. In such configurations, only a portion of the bias vents 2502 is positioned laterally beyond the inlet 2732. In some embodiments, the bias vents 2502 are positioned entirely beyond a side of the inlet 2732. The bias vents 2502 can be configured to help disperse the exhausted air. Such configurations can reduce disturbance, such as draft and/or noise, caused by the exhausted air to the user and/or the user's bed partner.

Figure 23:
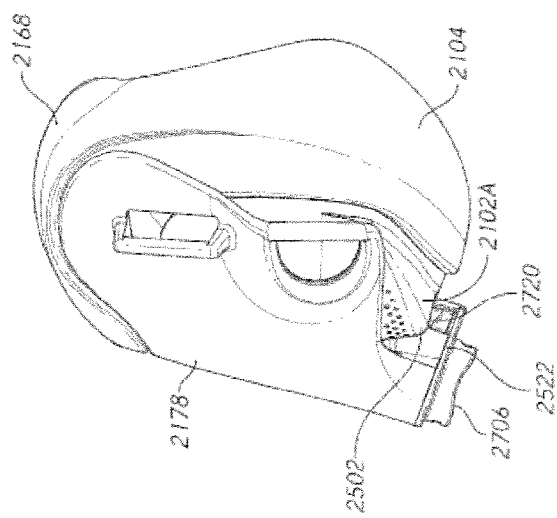
FIG. 23 is a side view of the mask assembly of FIG. 2A.
Figure 26:
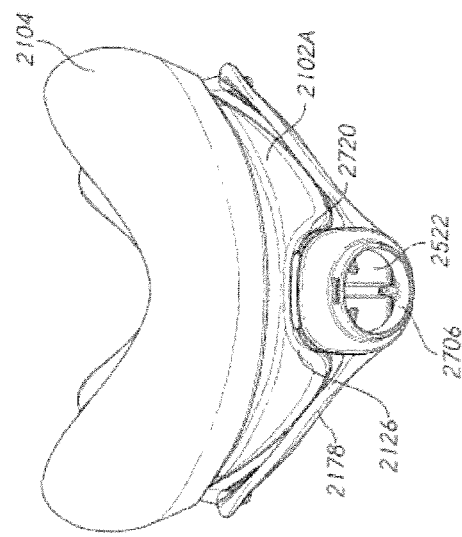
FIG. 26 is a bottom view of the mask assembly of FIG. 2A.

In some embodiments, the bias vents 2502 are positioned such that air is exhausted below the frame 2178 (see FIGS. 23-25). For example, the bias vents 2502 are positioned immediately below and/or adjacent a lower edge of the frame 2178. Such configurations can allow vented air to pass the frame 2178 with little or minimal disturbance to airflow. As discussed above, such configurations can help to disperse the exhausted air, reduce noise, and/or reduce disturbance caused by the exhausted air.

In some embodiments, the housing 2102 includes the valve recess 2726. The valve recess 2726 can define a concave region. The concave region can be positioned below and/or adjacent the inlet 2732. In some embodiments, the valve recess 2726 can have a width that is less than a maximum width of the inlet 2732.

As described above, the valve recess 2726 can receive at least a portion of the A-A valve 2522, such as a rear portion of the A-A valve 2522 and/or the valve outlets 2720. In some embodiments, the valve recess 2726 has a curved surface that includes a curvature accommodating or matching a curvature of a rear surface/wall 2523 of the A-A valve 2522.

In at least some embodiments, the valve recess 2726 allows the A-A valve 2522 to be positioned recessed into the cushion module 2150 and/or below at least a portion of the mask seal 2104, such as a forward upper portion and/or the nasal region 2168 of the mask seal 2104. In at least some embodiments, the valve recess 2726 and/or the A-A valve 2522 can desirably reduce an overall depth of the patient interface. This can help to reduce the obtrusiveness of the patient interface to the user and reduce hose pull. In at least some embodiments, the valve recess 2726 and/or the A-A valve 2522 can allow the A-A valve 2522 to be positioned higher relative to the bottom of the mask seal 2104 and/or the inlet 2732 to be shorter. This can help to reduce the overall size of the mask assembly 2100.

As mentioned above, the housing 2102 can include the frame connector 2730. As shown in FIG. 12, the frame connector 2730 can form a collar. The collar can protrude inwardly from a front surface of the housing 2102 toward or into an interior of the cushion module 2150. The frame connector 2730 can extend around an entirety or a portion of a perimeter of the inlet 2730. In some embodiments, the frame connector 2730 can receive and/or retain the cushion connector 2708 of the frame 2178.

In some embodiments, the frame connector 2730 can include a securement feature to engage the cushion connector 2708 of the frame 2178. For example, the frame connector 2730 can include at least one connector bump 2734 (e.g., a pair of connector bumps 2734) or other retention or alignment features. The connector bump 2734 can be positioned along a portion of an interior surface of the frame connector 2730. The connector bump 2734 can engage with a corresponding engagement feature 2715 of the cushion connector 2708. The engagement feature 2715 can include a notch, recess, or other engagement feature. The engagement feature 2715 can be positioned on an outer surface of the cushion connector 2708. In some embodiments, the connector bump 2734 can engage with the engagement feature 2715 of the cushion connector 2708 by a snap-fit arrangement, among other engagement arrangements. In some embodiments, the cushion connector 2708 includes a pair of laterally opposed recesses 2715 that are configured to receive and/or retain a corresponding pair of connector bumps 2734 on the frame connector 2730. Such configurations can secure the frame 2178 to the cushion module 2150.

Figure 16:
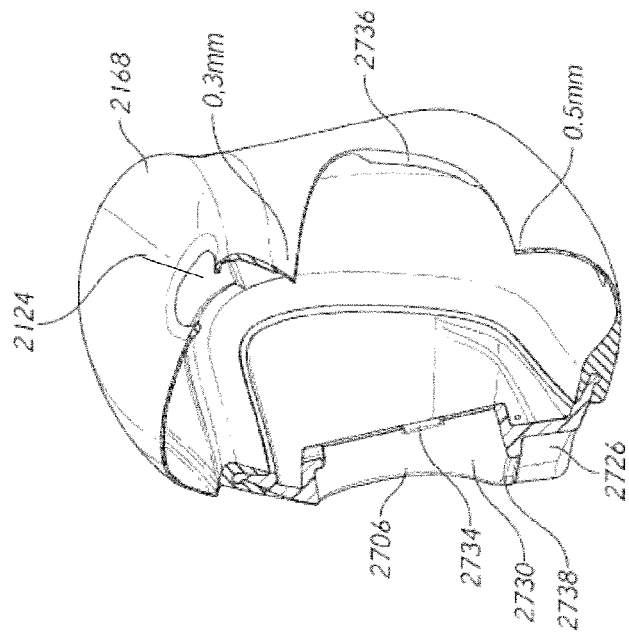
FIG. 16 is a side cross-sectional view of the cushion module of the mask assembly of FIG. 2A.
Figure 15:
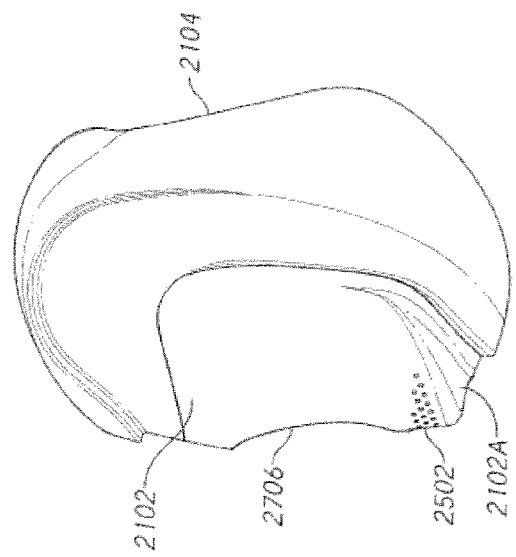
FIG. 15 is a side view of the cushion module of the mask assembly of FIG. 2A.
Figure 24:
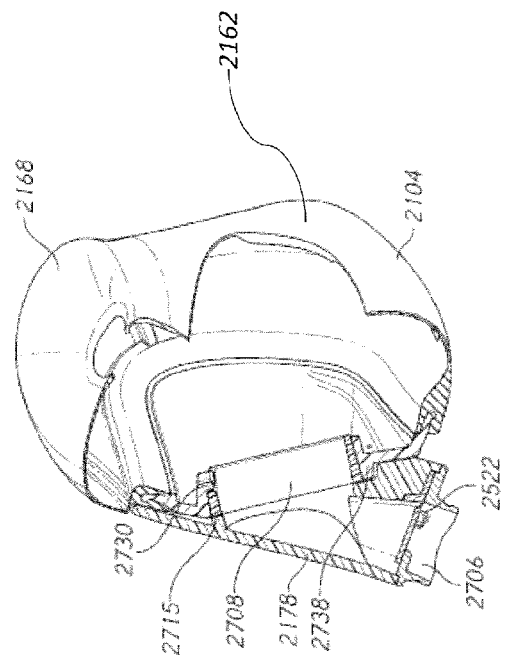
FIG. 24 is a side cross-sectional view of the mask assembly of FIG. 2A.
Figure 25:
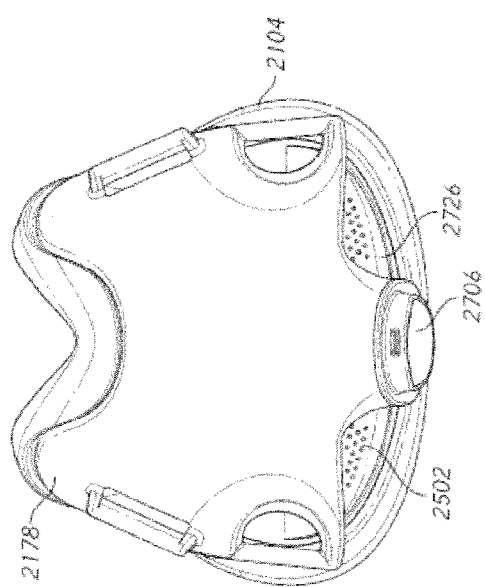
FIG. 25 is a front view of the mask assembly of FIG. 2A.

As shown in at least FIGS. 16 and 24, in some embodiments, the frame connector 2730 can include a lip 2738. The lip 2738 can define an upper wall of the valve recess 2726. In some configurations, the lip 2738 can be recessed relative to a front side of the housing 2102. In some embodiments, the lip 2738 can form at least a portion of the frame connector 2730 and/or the inlet 2732. When assembled, the lip 2738 can be positioned above the valve outlet 2720.

As described above, the frame connector 2730 can include an alignment feature 2714. The alignment feature 2714 can protrude radially into the inlet and/or forward of a rear edge of the frame connector 2730. The alignment feature 2714 can engage with the alignment notch 2710 of the cushion connector 2708 of the frame 2178. Such configurations can help to align and/or secure the frame 2178 to the mask seal 2104.

In some embodiments, the mask seal 2104 is substantially resilient. In some embodiments, the mask seal 2104 can include a nasal region 2168 and an oral seal portion. The nasal region 2168 can include a nasal opening 2124 and right and left nasal sealing surfaces 2124A, 2124B. The right and left nasal sealing surfaces 2124A, 2124B can extend outwardly from the nasal opening 2124. In some embodiments, the oral seal portion can include an oral opening 2122 (see FIG. 13).

As shown in at least FIGS. 13-14, the cushion module 2150 can include the inlet 2732. The inlet 2732 can form an opening in the cushion module 2150 to allow air to flow into the breathing chamber. In some embodiments, the inlet 2732 can include a noncircular perimeter. In some embodiments, the perimeter of the inlet 2732 is generally oval-shaped, elliptical-shaped, square-shaped, and/or rectangular-shaped, among other shapes. In some embodiments, the inlet 2732 includes a generally rounded 'D' shape and/or a rounded trapezoidal shape, among other shapes. The inlet 2732 having a non-circular perimeter can desirably help to more easily assemble and/or align the frame 2178 and the cushion module 2150. Such configurations can help to prevent incorrect assembly of the seal 2104 to the frame 2178. Such configurations can help to inhibit or limit rotation of the frame 2178 relative to the cushion module 2150 when assembled. In some embodiments, the noncircular perimeter of the inlet 2732 can allow at least a portion of the valve 2522 to be positioned closer to a center of the inlet 2732 than a design having a circular inlet 2732, since such non-circular configuration of the inlet 2732 will have smaller height than the circular inlet 2732. Such non-circular configurations can desirably create additional space for the valve 2522, thereby reducing the overall size (e.g., height) of the mask assembly 2100 when assembled in comparison to a mask having a circular inlet.

As discussed above, the mask seal 2104 can include the nasal region 2168. The nasal region 2168 can include left and right sealing surfaces 2124B, 2124A. In some embodiments, each of the left and right sealing surfaces 2124B, 2124A can define a convex region. As described previously herein, the left and right sealing surfaces 2124B, 2124A cooperate to define a concave region, which is configured to receive the user's nose. The convex region of the left and right sealing surfaces 2124B, 2124A can be generally flattened. For example, the flattened convex region can extend from a top of the left and right sealing surfaces 2124B, 2124A towards the nasal opening 2124. The flattened convex region can have a generally linear profile as the left and right sealing surfaces 2124B, 2124A extends from the uppermost point towards the nasal opening 2124. The flattened sealing surfaces 2124B, 2124A can help to prevent or limit creases forming in the sealing surfaces 2124B, 2124A when the nasal region 2168 engages the user's nose in use, for example. Some configurations can help to minimize leaks around the user's nose in use.

Figure 17:
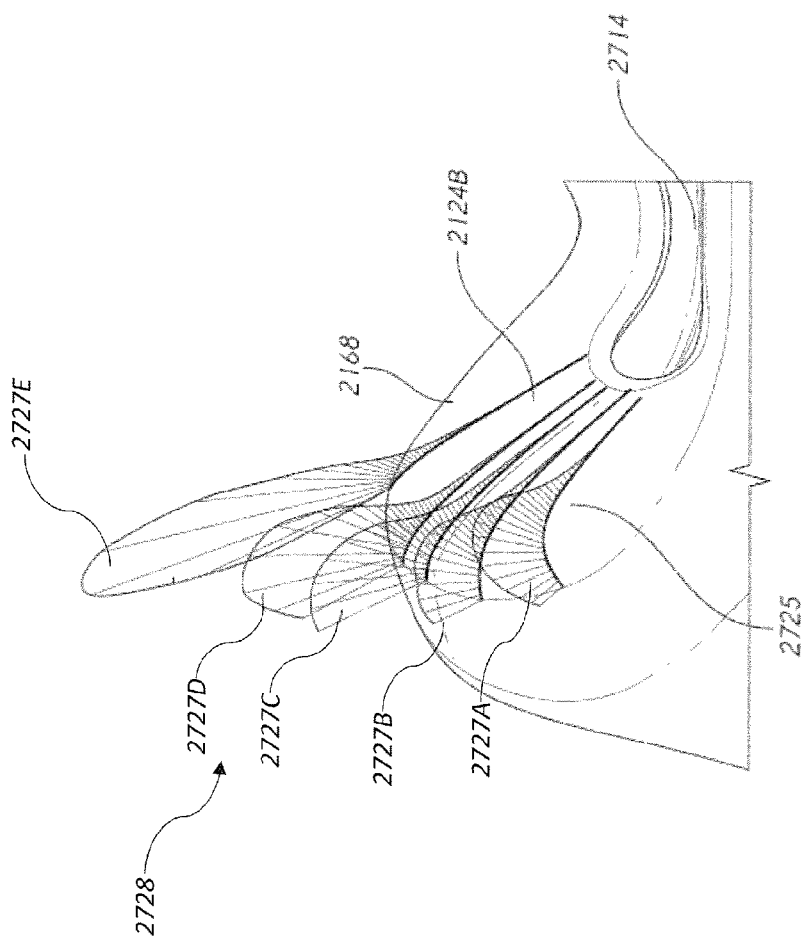
FIG. 17 is a close-up rear view of a mask seal portion of the cushion module of the mask assembly of FIG. 2A.

FIG. 17 illustrates a close-up rear view of a portion of the nasal region 2168. Though the left nasal sealing surface 2124B is shown and described, the right nasal sealing surface 2124A can include similar features and, preferably, is a mirror-image of the left nasal sealing surface 2124B. As shown, the nasal sealing surface 2124B can be relatively flat laterally adjacent to the nasal opening 2124. In some embodiments, the curvature of the nasal sealing surface 2124B can be relatively low (e.g., approximately linear) as the nasal sealing surface 2124B extends radially outward from the nasal opening 2124 towards the uppermost point of the nasal sealing surface 2124B. In some embodiments, the curvature of the nasal sealing surface 2124B can be relatively low as the nasal sealing surface 2124B extends radially outward from the nasal opening 2124 to approximately a midpoint 2725 of the nasal sealing surface 2124B, as illustrated by the lines of curvature 2727A, 2727B, 2727C, 2727D, 2727E. In some embodiments, the curvature of the nasal sealing surface 2124B increases as the nasal sealing surface 2124B extends radially outward beyond the midpoint 2725 (e.g., at an outer nasal sealing surface region).

As indicated by a curve plot 2728 and as described in more detail below, the radius of curvature of the outer nasal sealing surface region decreases in a rearward to forward direction along the surface of the outer nasal sealing surface region. For example, in some embodiments, the radius of curvature of the outer nasal sealing surface region at the rearward portion of the nasal sealing surface 2124B is larger than the radius of curvature of the outer nasal sealing surface region at the forward portion of the nasal sealing surface 2124B. That is, the nasal sealing surface 2124B can go from less curved to more curved moving in a rearward to forward direction.

Figure 18:
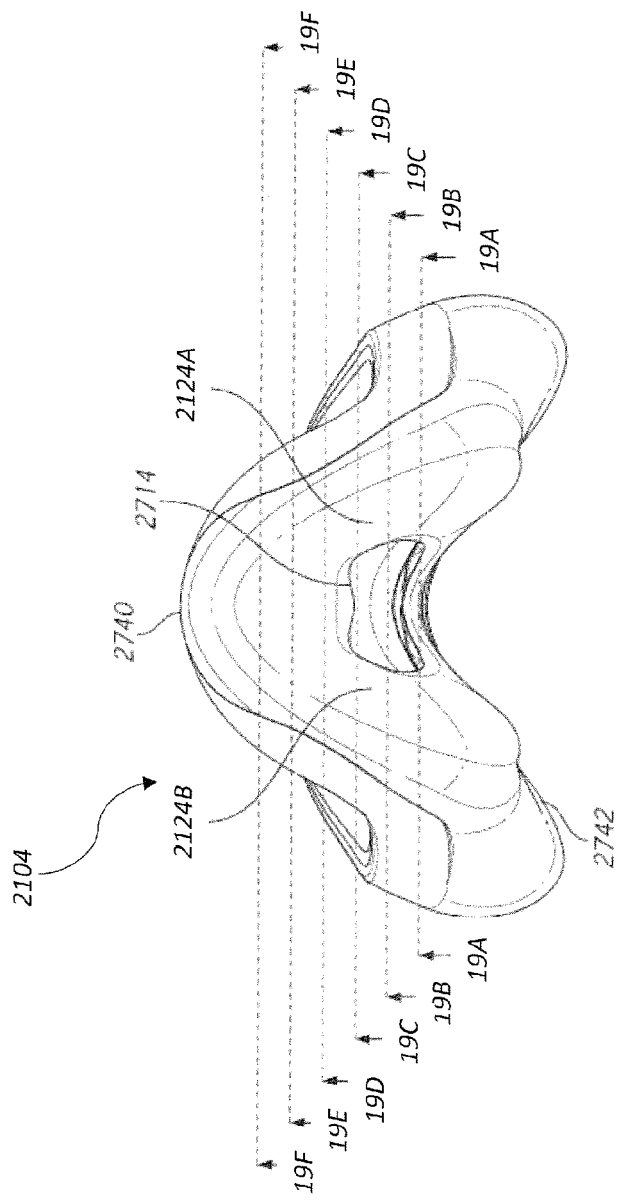
FIG. 18 is a top view of the mask seal of the cushion module of the mask assembly of FIG. 2A.

FIG. 18 shows a top view of the mask seal 2104. FIGS. 19A-19F are sectioned views as viewed from the rear of the mask seal 2104. As shown, in some embodiments, the left and right nasal sealing surfaces 2124B, 2124A can be angled away from each other in at least two dimensions. For example, when viewed from the front or rear, the left and right nasal sealing surfaces 2124B, 2124A can extend upwardly away from the nasal region 2168 at an angle to form a generally V-shape. In some embodiments, when viewed from the top, the left and right nasal sealing surfaces 2124B, 2124A can be angled away from each other in a direction from a front 2740 to a rear 2742 of the mask seal 2104 or seal assembly 2100. In such configurations, the nasal region 2168, including the left and right nasal sealing surfaces 2124B, 2124A can form a generally triangular shape. Such configurations can desirably accommodate or generally match the geometry of a user's nose. This can provide more stability and/or comfort to the user. Such configurations can help to reduce leakages of air from the mask seal 2104.

Figures 19D, 19E, 19F:
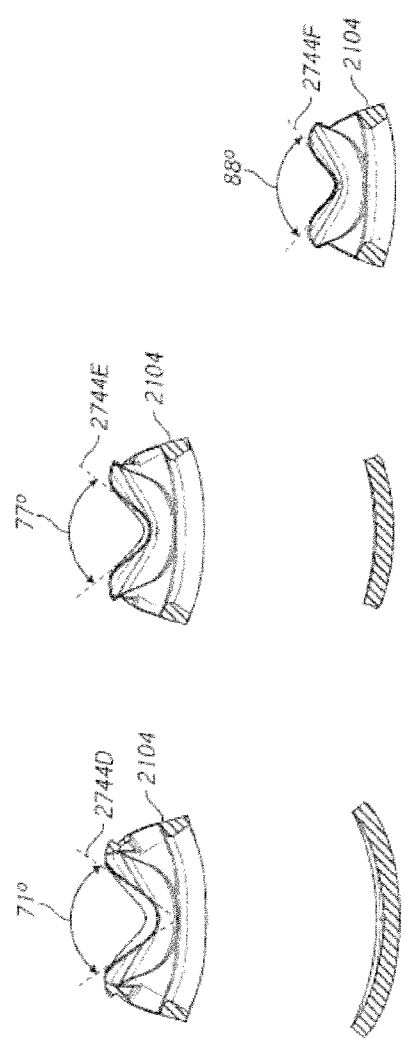
FIG. 19D is a rear cross-sectional view of the mask seal of the mask assembly of FIG. 2A taken along the line 19D-19D of FIG. 18.
FIG. 19E is a rear cross-sectional view of the mask seal of the mask assembly of FIG. 2A taken along the line 19E-19E of FIG. 18.
FIG. 19F is a rear cross-sectional view of the mask seal of the mask assembly of FIG. 2A taken along the line 19F-19F of FIG. 18.

FIG. 19A illustrates a rear cross-sectional view taken along line 19A-19A of FIG. 18. FIG. 19B illustrates a rear cross-sectional view taken along line 19B-19B of FIG. 18. FIG. 19C illustrates a rear cross-sectional view taken along line 19C-19C of FIG. 18. FIG. 19D illustrates a rear cross-sectional view taken along line 19D-19D of FIG. 18. FIG. 19E illustrates a rear cross-sectional view taken along line 19E-19E of FIG. 18. FIG. 19F illustrates a rear cross-sectional view taken along line 19F-19F of FIG. 18. As shown in FIGS. 19A-19F, the left and right nasal sealing surfaces 2124B, 2124A of the nasal region 2168 can be angled outwardly and upwardly away from each other, and from the central vertical plane, in a bottom to top direction. In some embodiments, an angle between the left and right nasal sealing surfaces 2124B, 2124A increases in a rear to front direction. In some embodiments, a depth of the nasal region 2168 decreases in a rear to front direction. For example, the angle 2744A can be approximately 57 degrees, the angle 2744B can be approximately 60 degrees, the angle 2744C can be approximately 64 degrees, the angle 2744D can be approximately 71 degrees, the angle 2744E can be approximately 77 degrees, the angle 2744F can be approximately 88 degrees, and angles therebetween such ranges. Such configurations can allow the nasal region 2168 to engage with the user's nose in use without extending over the tip of the user's nose. Such configurations can desirably better match the geometry of a user's nose. This can provide more stability and/or comfort to the user. Such configurations can help to reduce leakages of air from the mask seal 2104.

FIGS. 20A-22C illustrates various views of the cushion module 2150 including the mask seal 2104 and the housing 2102 according to one embodiment. The mask seal 2104 preferably comprises a pair of upwardly extending portions or upward extensions 2126 (see, for example, FIG. 21A). The upwardly extending portions 2126 extend upwardly from opposite sides of a central sealing surface of the seal. The central sealing surface is provided in a central portion of the mask seal 2104. The upwardly extending portions may be referred to as "seal paddles." The upper surface 2130 can define a line that lies along the central surface of the nasal region 2168 of the mask seal 2104 in a fore-aft direction. Such a line extends generally along the nasal septum in a direction away from the user's face. The upwardly extending portions 2126 are configured to extend upward alongside, and in some configurations above, the nares. The upwardly extending portions 2126 can contact the edges of the nares and/or sides of the nose. The upwardly extending portions 2126 or portions of the mask seal 2104 between the upwardly extending portions 2126 may or may not cover the tip of the user's nose. As described herein, preferably the mask seal 2104 does not contact the bridge of the user's nose.

In some configurations, the upwardly extending portions 2126 each comprise an air pocket that is formed by an internal wall (including nasal sealing surface 2124A,B) and an external wall of the upwardly extending portions 2126. Such air pocket may be in direct fluid communication with the air path through the mask assembly 2100, such that the upwardly extending portions 2126 can be configured to expand in volume in response to elevated pressure within the mask seal 2104 and/or flex inwardly to accommodate various facial and nasal geometries and assist in creating a sealed contact with the user's face. Expansion of the upwardly extending portions 2126 can assist in sealing against the face of the user, especially along the varying contours on and around the user's nose. Inward flexing of the upwardly extending portions 2126 allows the central portion (e.g., upper surface 2130) to move downward with less restriction or less stretching of the material of the mask seal 2104 so that the mask seal 2104 can better conform to various nasal geometries.

The height of the upwardly extending portions 2126 above the upper surface 2130 can be selected to provide a desired balance between stability of the mask seal 2104 on the user's face (e.g., vertical stability) and being able to accommodate a range of nasal geometries or reducing visual disruption by the upwardly extending portions 2126. In general, taller upwardly extending portions 2126 tend to provide additional vertical stability of the mask assembly 2100, while shorter upwardly extending portions 2126 tend to provide a better fit of a wider range of users and result in less visual disruption. In some configurations, the height of the upwardly extending portion 2126 is between about 10 mm and about 30 mm or between about 15 mm and about 25 mm. In some configurations, the height of the upwardly extending portion 2126 is between about 15 mm and about 22 mm or between about 18 mm and about 20 mm, including any value or sub-range within the above described ranges. In some configurations, the height of the upwardly extending portion height is about 18.5 mm.

The mask seal 2104 can also comprise support structures or supports 2163 for the upwardly extending portions 2126, which can be in the form of suspension members or springs that provide mechanical rigidity and structure to hold the shape of the upwardly extending portions 2126 when the mask seal 2104 is worn by a user. The supports 2163 can comprise thickened regions of the seal material. The supports 2163 preferably are sized, shaped and/or otherwise configured to transfer force from a rearward or user-contacting surface of the upwardly extending portions 2126 toward or to a forward surface of the upwardly extending portions 2126. In some configurations, the interface assembly can include a support portion or cover for the upwardly extending portions 2126, for example the upwardly extending supports 2179, and the supports 2163 can transfer force from the rearward surface of the upwardly extending portions 2126 to the forward surface or other portion of the upwardly extending portions 2126 or mask seal 2104 that contacts or faces the upwardly extending supports 2179 or another portion of the frame 2178. In some configurations, the supports 2163 can transfer force from the rearward surface of the upwardly extending portions 2126 toward or to another support portion of the mask seal 2104, the housing 2102, or any other components of the interface assembly. The supports 2163 can resist or prevent collapse of the upwardly extending portions 2126 or other related or adjacent portions of the mask seal 2104 to facilitate fitment and provide feedback to the user, such as in response to applied forces (e.g., headgear forces). In some configurations, the supports 2163 can resist or prevent collapse of the upwardly extending portions 2126 or other related or adjacent portions of the mask seal 2104 in the absence of significant internal gas pressure.

The supports 2163 can help maintain the shape of the upwardly extending portions 2126 of the mask seal 2104 and/or help maintain a separation between a rear wall of the mask seal 2104 (defining a face contacting surface) and a front wall of the mask seal 2104 at least in response to forces experience during normal use. In addition, the supports 2163 can provide support to the nasal region 2168. In particular, the supports 2163 can provide structure to and inhibit or prevent creasing, wrinkling or collapsing of the nasal region 2168. As described above, the nasal region 2168 preferably is relatively thin to permit this portion of the mask seal 2104 to conform to the user's nose. The relatively thin nasal region 2168 can expand and seal around the user's nose. The supports 2163 provide relatively rigid portions or elements of the seal 2104 adjacent or near the relatively thin nasal region 2168 to inhibit or prevent collapse when a user engages his or her nose into the mask assembly 2100.

In some configurations, the supports 2163 help to reduce the likelihood of wrinkling or creasing of the nasal sealing surfaces 2124A, 2124B of the upwardly extending portions 2126 during use while allowing the laterally inner portions to be as thin as desired within practical limitations. The supports 2163 can assist in inhibiting or preventing collapse of the upwardly extending portions 2126 or maintaining a desired shape of the upwardly extending portions 2126. For example, the supports 2163 can assist in maintaining a desired fore-aft shape of the upwardly extending portions 2126 and/or a lateral or side-to-side shape of the upwardly extending portions 2126. The level of support provided can vary in different directions. In some configurations, the supports 2163 could be formed as separate portions or separate components from the seal material and could be the same or a different material. Such separate supports 2163 could be coupled to the upwardly extending portions 2126 or other portion of the mask seal 2104 if desired. The supports 2163 disclosed herein can be particularly useful in undernose type mask assemblies, including both nasal masks and combined nasal-oral masks. However, the supports 2163 can also be utilized in other types of mask assemblies or interfaces, including those that cover, contact or seal against the bridge of the user's nose and/or include a T-piece or other type of forehead support, for example and without limitation. The supports 2163 can be utilized, or modified for use, in any locations of an interface in which support against collapsing and/or support against overexpansion may be desirable. Such locations can be at or near the portion of the seal that contacts or extends alongside the user's nose or can be at other locations.

In the illustrated arrangement, at least a portion of the supports 2163 extend generally in a fore-aft direction along the upwardly extending portions 2126. In particular, the supports 2163 can extend along the upper edge 2169 of the upwardly extending portions 2126 or the region or ridge that joins the nasal sealing surfaces 2124A and 2124B along the upper edges 2169 of the upwardly extending portions 2126. The supports 2163 can extend along a portion of the sides of the nasal region 2168. The supports 2163 can comprise a generally narrow, elongate shape. Viewed from above, the supports 2163 can comprise a generally triangular shape with a base of the triangle positioned rearwardly of the top or point of the triangle. Viewed from side, the supports 2163 can comprise a generally sickle or crescent shape. Other shapes are possible to achieve a desired level of support or for other design considerations, such as the desired shape(s) of adjacent or nearby structures. The supports 2163 can have additional portions to provide other levels of support or to provide support in other directions. For example, the supports 2163 could connect to one another, such as along one or both of the forward or rearward sides of the nasal opening 2124. In some configurations, the supports 2163 could extend completely through the upwardly extending portions 2126, such as to the housing 2102, for example.

The illustrated mask seal 2104 of the cushion module 2150 comprises a range and configuration of thicknesses. The thicknesses are varied to take advantage of or provide different characteristics in different regions of the illustrated mask seal 2104. For example, the thicknesses in the various regions can be selected to address a desired characteristic for that region and/or the mask seal 2104 as a whole. Such characteristics can include, for example, allowing the mask seal 2104 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

As described above, the mask seal 2104 can include various regions of different thickness. Examples of such arrangements are disclosed in Applicant's publication no. WO 2015/193821A1, the entirety of which is incorporated by reference herein. In general, the outer surface of the mask seal 2104 defines a relatively smoothly shaped or curved surface without abrupt changes in direction. The different thicknesses are created by changes in wall thickness that are apparent on or created by changes in shape of an interior surface of the mask seal 2104.

The supports 2163 can have a different thickness than other portions of the upwardly extending portions 2126 and can have a greater thickness than other portions of the upwardly extending portions 2126. In some configurations, the supports 2163 can have the largest thickness or among the largest thicknesses of the mask seal 2104. In some configurations, a portion or an entirety of the supports 2163 can have a thickness of between about 1.5 mm and about 3.5 mm. In some configurations, the supports 2163 may have a thickness of between about 4 mm and about 5 mm. In some configurations, a portion or an entirety of the supports 2163 can have a thickness of about 2.5 mm. The thickness of the supports 2163 can be constant or variable. In some configurations, support structures 2163 for the upwardly extending portions 2126 are thicker than the nasal region 2168.

Figure 21A:
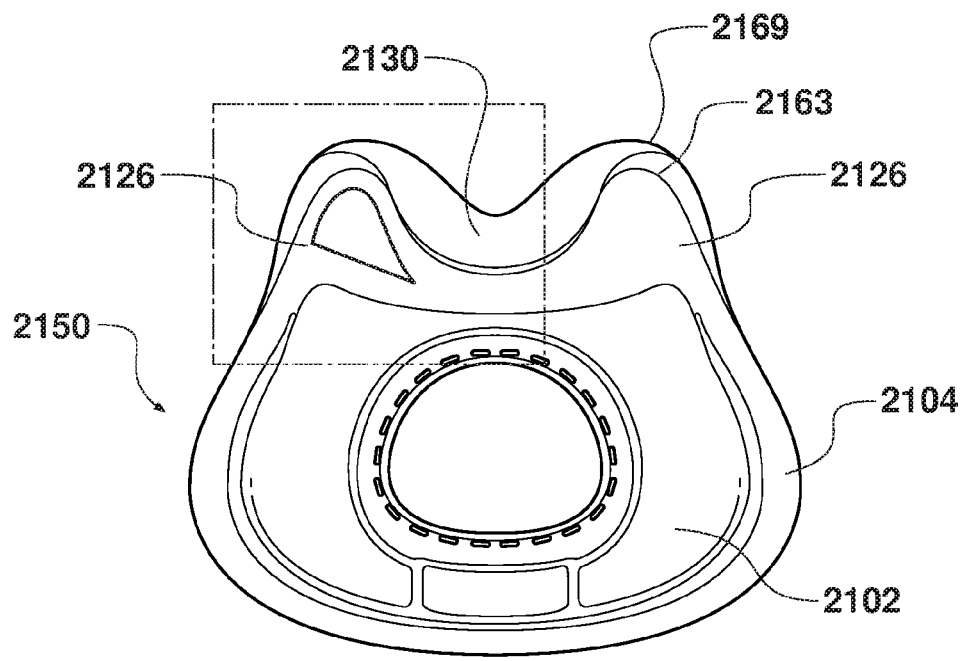
FIG. 21A is a front view of the cushion module of the mask assembly of FIG. 20A.
Figure 21B:
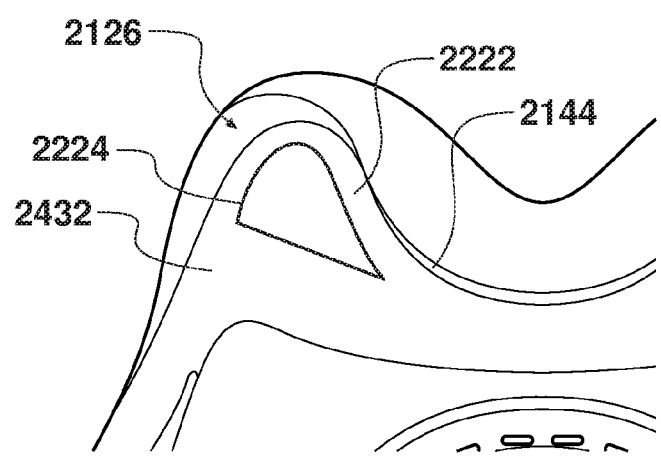
FIG. 21B is an enlarged view of an upper portion of the cushion module of the mask assembly of FIG. 20A.
Figure 21C:
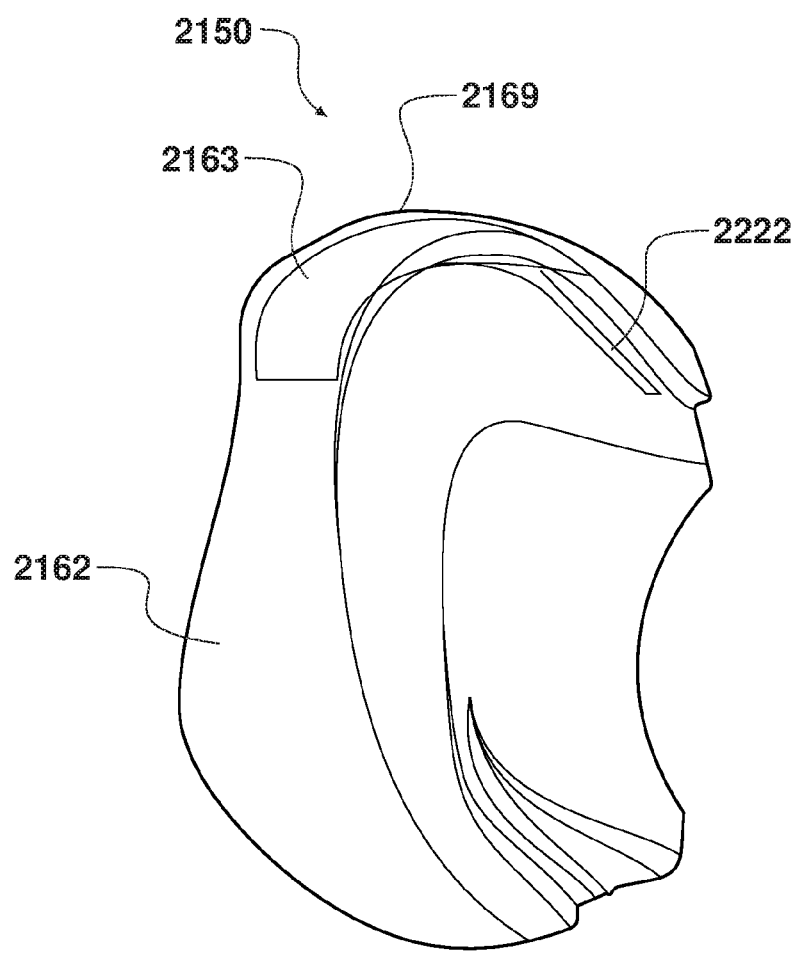
FIG. 21C is a side view of the cushion module of the mask assembly of FIG. 20A.
Figure 21D:
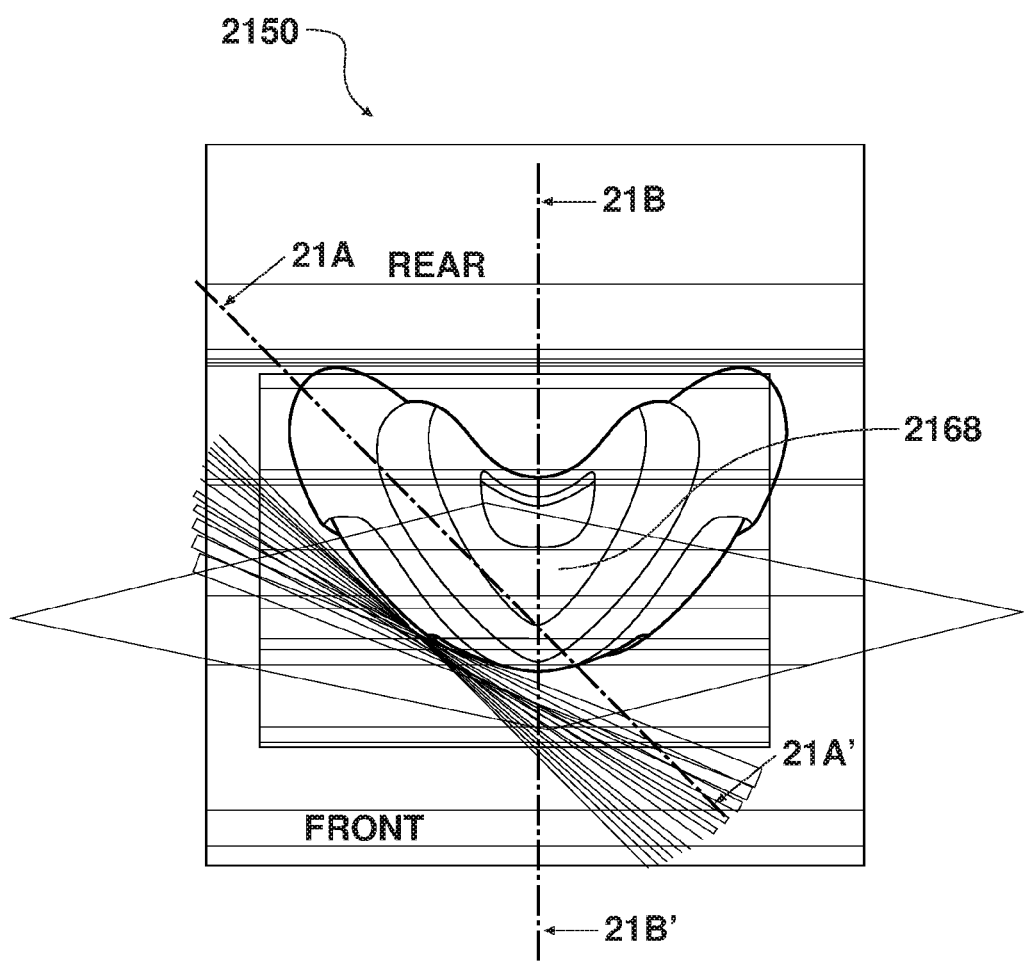
FIG. 21D is a top view of the cushion module of the mask assembly of FIG. 20A.

To reduce the incidence of wrinkling of at least some of the face contacting regions of the mask seal 2104 during use, it has been found that outer peripheral portions 2162 of the mask seal 2104, shown in FIG. 21C, which are generally adjacent to some or all of the face contacting portions of the mask seal 2104, provide desirable performance when the outer peripheral portions 2162 are fairly rigid or relatively rigid compared to adjacent portions or other portions of the mask seal 2104. In the illustrated arrangement, the outer peripheral portions 2162 extend along the generally vertically extending portions on the rear of the mask seal 2104 and wrap slightly inward at a bottom of the rear of the mask seal 2104. In addition, the outer peripheral portions 2162 wrap from a rear facing side of the mask seal 2104 around to at least a portion of a laterally facing side of the mask seal 2104. In some configurations, the outer peripheral portions 2162 extend along the cheeks of the user. The outer peripheral portions 2162 can extend inward toward or to the chin or the region below the user's lower lip for a full-face mask or the region above the user's upper lip for a nasal mask.

In the illustrated arrangements, the outer peripheral portions 2162 are located on each lateral side of the oral opening 2122. In some configurations, the outer peripheral portions 2162 extend along an entire height of the oral opening 2122. Upper ends of the outer peripheral portions 2162 can extend at least to about an upper end of the oral opening 2122. Lower ends of the outer peripheral portions 2162 can extend below a lower end of the oral opening 2122. As described above, in some configurations the outer peripheral portions 2162 wrap inwardly below the oral opening 2122 such that portions of the outer peripheral portions 2162 are positioned vertically below portions of the oral opening 2122.

The relatively increased thickness of the outer peripheral portions 2162 can assist in resisting or preventing collapse of the mask seal 2104 in the absence of significant internal gas pressure to facilitate fitment and provide feedback to the user, such as in response to applied forces (e.g., headgear forces). The outer peripheral portions 2162 can help maintain the curved shape of the lateral sides of the mask seal 2104 and/or help maintain a separation between a rear wall of the mask seal 2104 (defining a face contacting surface) and a front wall of the mask seal 2104 at least in response to forces experience during normal use. In some configurations, the thickness of a portion or an entirety of the outer peripheral portions 2162 can be between about 1.0 mm and about 2.0 mm. In the illustrated configuration, a portion or an entirety of the outer peripheral portions 2162 preferably have a thickness of about 1.5 mm. The thicknesses of the outer peripheral portions 2162 can be constant or varied within a boundary of the outer peripheral portion 2162.

In some configurations, the upper portion of the front surface of the seal 2104 adjacent the external wall or front surface of the upwardly extending portions 2126, includes an upper recessed surface 2432 (see, for example, FIGS. 12 and 21B) formed within the seal 2104. In the illustrated configuration the upper recessed surface 2432 is positioned along the front side of the upwardly extending portions 2126. The upper recessed surface 2432 can extend along the outer peripheral portions 2162 of the front side of the mask seal 2104. The upper recessed surface 2432 can extend rearwardly around the sides of the mask seal 2104. In some configurations, the upper recessed surface 2432 can extend downwardly approximately half a height of the front side on each side of the seal 2104. In some configurations, the upper recessed surface 2432 extends downwardly less than half of the front side and in some instances about ⅓ of the front side of the seal 2104. An upper edge portion of the seal 2104 projects forwardly from the seal 2104 and, in particular, forwardly from the upper recessed surfaces 2432. This projection together with each upper recessed surface 2432 may form recesses to either side of the seal. The upwardly extending supports 2179 are received in respective recesses when the frame 2178 is assembled to the cushion module 2150. The upwardly extending supports 2179 provide support to respective upper recessed surfaces 2432. The upwardly extending supports 2179 engage the upper recessed surfaces 2432 when the seal 2104 is inflated in use and/or when the seal 2104 is not in use (and not inflated). The forward projection of the upper edge of the seal 2104 forms an overhang that extends over the upper edge of the frame 2178 when the frame 2178 is assembled to the cushion module 2150.

In some configurations, the upper recessed surface 2432 forms a stepped transition between an upper periphery of the upper front portion that extends along the curvature of a periphery or an upper edge of the upwardly extending portions 2126. In some embodiments, the support 2163 may form at least part of the stepped transition. In some configurations, the stepped transition extends at a constant depth or a varying depth. For example, the depth of the stepped transition can be constant throughout the entire stepped transition. However, in some configurations, the stepped transition varies. For example, the stepped transition can be tapered. In this arrangement, the depth may be smallest at or relatively near a lower or lateral extreme of the stepped transition. In some embodiments, however, the depth is smallest at or relatively near an upper extreme of the stepped transition.

The seal 2104 may include additional features configured to reduce the likelihood of wrinkling or creasing of the face contacting portions of the upwardly extending portions 2126 during use while allowing the laterally inner portions to have an advantageously small wall thickness. For example, in some embodiments, the front or external wall of each of the upwardly extending portions 2126 of the seal 2104 may include a thin region or thin pocket 2224, as illustrated in FIGS. 20A, 20B, 21B and 21E for example. The front wall at the thin pocket 2224 may have a reduced thickness in comparison to the surrounding wall portion. For example, the front wall at the thin pocket 2224 may have thickness of 0.2 mm to 0.4 mm, preferably approximately 0.3 mm, while the surrounding wall may have thickness of 0.4 mm to 2.6 mm. In some embodiments, the wall thickness of the thin pocket 2224 may vary along the region of the thin pocket 2224. In some embodiments, the change of wall thickness of the thin pocket 2224 may be located on an internal surface 2142 of the front wall of the upwardly extending portions 2126, such that the thin pocket 2224 forms a step on the internal surface 2142 as illustrated in FIG. 21E, while an outer surface of the front wall at the region of the thin pocket 2224 is smooth and continuous. Thus, in the illustrated configuration, the thin pocket 2224 may not be visible from the outside of the seal 2104. (FIGS. 20B and 21B include an outline of the thin pocket 2224 to illustrate its location in the inner surface). In other embodiments, the thin pocket 2224 may include a recessed outer surface and/or a recessed inner surface of the front wall of the upwardly extending portions 2126.

In some embodiments, the thin pocket 2224 may be substantially tear drop shape, with the narrower ends or points of the tear drop shape near a center front of the seal 2104. The thin pockets 2224 may taper in height towards the front of the seal, substantially following the contour of the upper edge of the upwardly extending portions 2126. In some embodiments, the thin pockets 2224 may have any suitable shapes, such as an oval shape. In some embodiments, at least a portion of the lower edge of the thin pocket 2224 is bounded by an upper portion of the over-moulded region 2106 of the seal 2104. The reduced wall thickness of the thin pockets 2104 may be limited to the upwardly extending portions 2126 or the upper front portion of the seal 2104 and not extend across the front wall of the seal 2104, which may reduce or limit creasing of the nasal sealing surfaces 2124A, 2124B. The upper edge of the thin pocket 2224 may be at least partially defined by a thickened rib 2222.

Figure 20A:
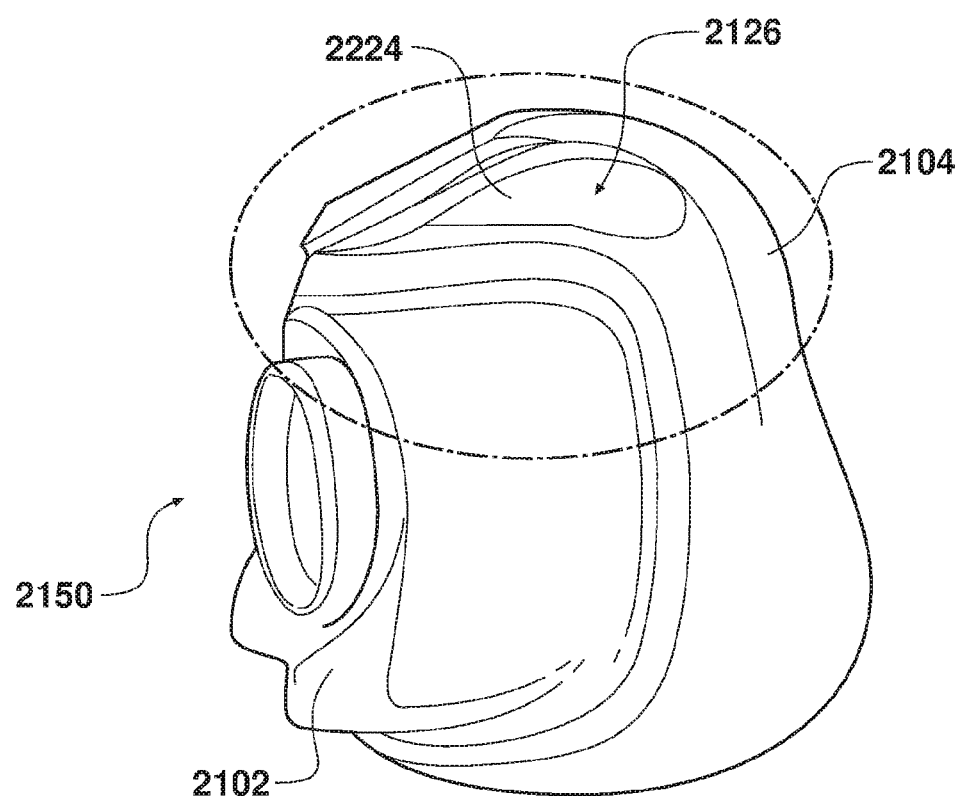
FIG. 20A is a front and side perspective view of a cushion module similar to the cushion module of the mask assembly of FIG. 2A.
Figure 20B:
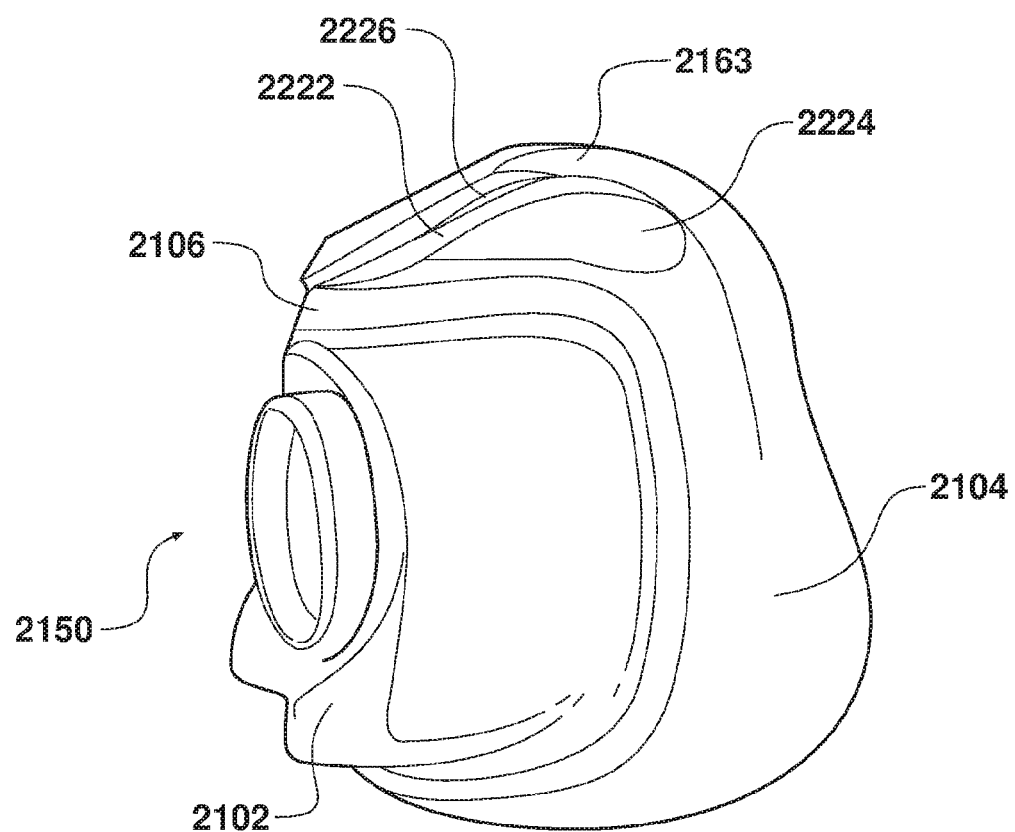
FIG. 20B is another version of a front and side perspective view of the cushion module of the mask assembly of FIG. 20A with transitions or boundaries between portions of different thicknesses outlined.
Figure 21E:
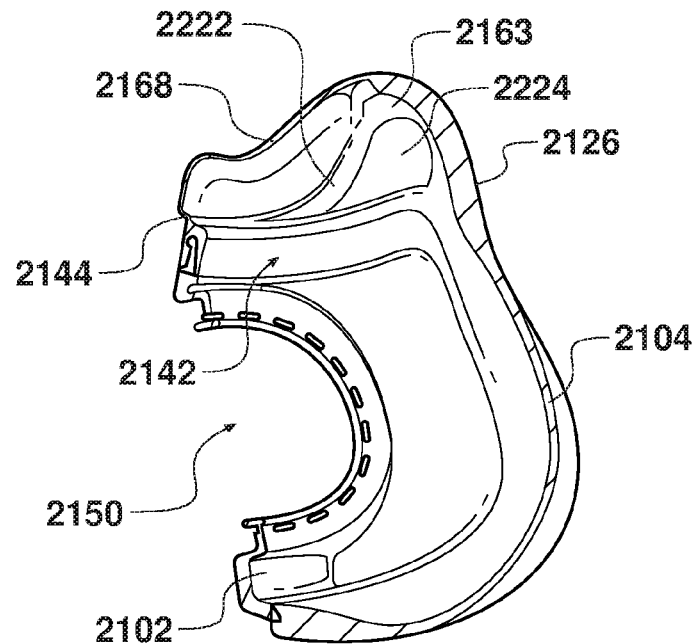
FIG. 21E is a rear cross-sectional view of the cushion module of the mask assembly of FIG. 20A taken along the line of 21A-21A of FIG. 21D.
Figure 21F:
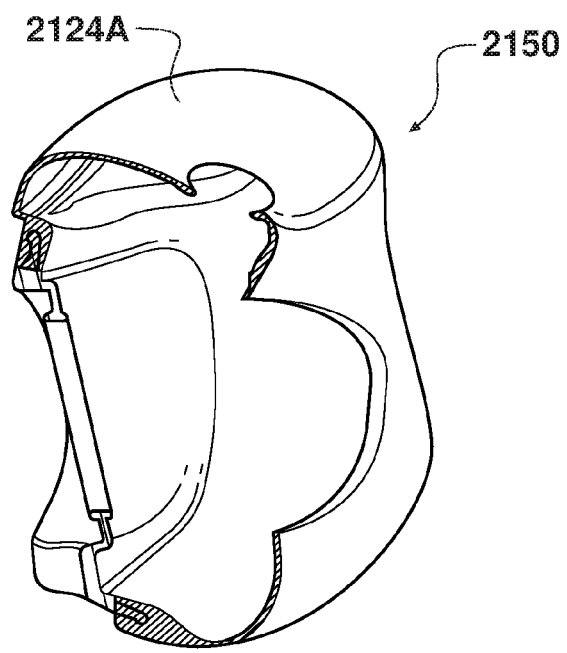
FIG. 21F is a side cross-sectional view of the cushion module of the mask assembly of FIG. 20A taken along the line of 21B-21B of FIG. 21D.

In some embodiments, the front wall of the each of the upwardly extending supports 2126 of the seal 2104 may include the thickened rib 2222, such as shown in FIGS. 20B, 21C and 21E. The thickened rib 2222 may extend along an upper portion of the external wall of the upwardly extending portion 2126 from a lower edge of the support structure 2163 toward the center of the seal 2104, providing additional support to the seal 2104. The thickened rib may be proximate to the upper edge 2169 of the seal 2104, but at the same time, it may be spaced from the upper edge 2169. Viewed from front, the thickened rib may be curved diagonally downward. The rib 2222 may generally follow the curvature of the upper edge of the upwardly extending portions 2126. In some embodiments, such as illustrated in FIG. 21E, the thickened rib 2222 may be located on the internal surface 2142 of the front wall of the upwardly extending portions 2126, such that the thickened rib 2222 forms a rearwardly-protruding structure between the thin pocket 2224 and the nasal sealing surface 2168.

As described above, the thickened rib 2222 may define at least a part of the upper edge of the thin pocket 2224. As illustrated, for example, in FIGS. 20B and 21B, the rib 2222 may at least partially extend along the corner/step 2144 of the upper recessed surface 2432. In some embodiments, the rib 2222 may mostly extend along the corner/step 2144 of the upper recessed surface 2432. In some embodiments, there may be a gap 2226 between the thickened rib 2222 and the step 2144 of the upper recessed surface 2432 adjacent where the rib 2222 merges with the support structure 2613, as shown in FIG. 20B. The gap 2226 may have a reduced thickness relative to the surrounding wall of the seal 2104. In some embodiment, the gap 2226 may have similar thickness to the thin pocket 2224. The gap 2226 may have thickness of 0.2 mm to 0.4 mm, preferably approximately 0.3 mm. In other embodiments, the thickened rib 2222 may extend along the step without the gap 2226.

The thickened ribs 2222 may have sufficient thickness to withstand vertical force to the upwardly extending portions 2126, such that the likelihood of wrinkling or creasing of the face contacting portions of the upwardly extending portions 2126 is reduced or limited. For example, the rib 2222 may have a thickness of between 1.0 mm and 2.0 mm, preferably between 1.1 mm and 1.4 mm. The thickened rib 2222 may have varying thickness along its length. For example, in some embodiments, the thickened rib 2222 may have a thickness that is greatest near the horizontal center of the seal 2104, such that the thickened rib 2222 provides relatively greater support at the central region of the seal 2104. In some embodiments, the thickened rib 2222 may have relatively constant thickness, height and/or width along its length. The thickened rib 2222 may evenly offset from the step 2144.

Figure 22A:
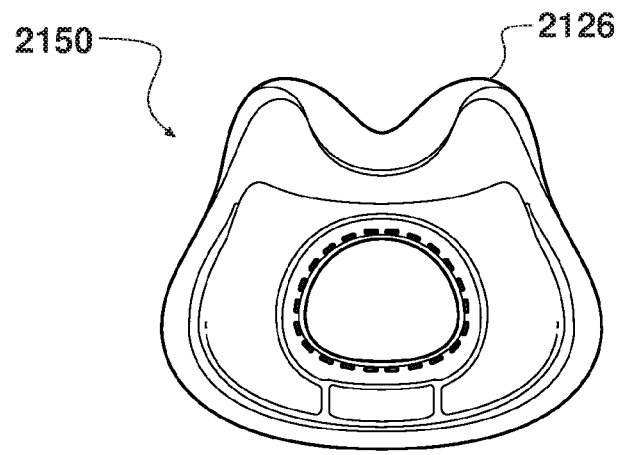
FIG. 22A is a front view of the cushion module of the mask assembly of FIG. 20A in neutral position.
Figure 22B:
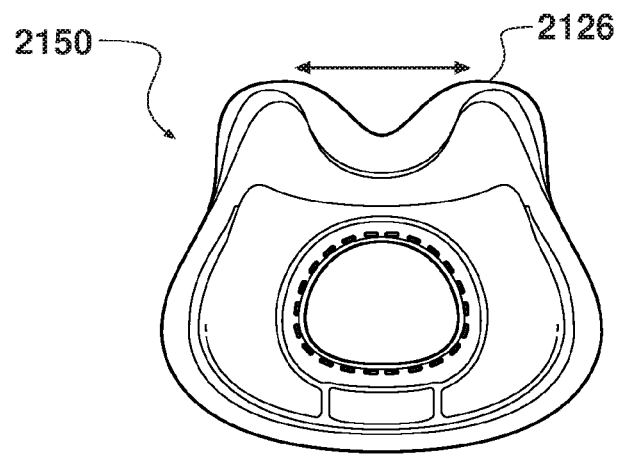
FIG. 22B is a front view of the cushion module of the mask assembly of FIG. 20A when a laterally outward force is applied to each side of a nasal sealing surface.
Figure 22C:
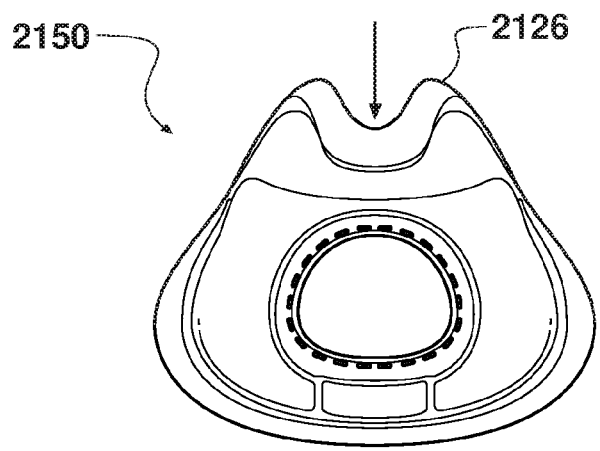
FIG. 22C is a front view of the cushion module of the mask assembly of FIG. 20A when a downward force is applied to the nasal sealing surface.

FIGS. 22A-22C illustrate several positions of the seal 2104, which may be facilitated or enhanced by the presence of one or both of the thin pocket 2224 and the thickened rib 2222. FIG. 22A illustrates the seal 2104 in its natural or relaxed position. The thin pocket 2224 provides flexibility in the outer walls of the upwardly extending portions 2126, such that the upwardly extending portions 2126 can flex outwardly, as shown in FIG. 22B, when a laterally outward force is applied to each side of the nasal region 2168 and/or the internal walls of the upwardly extending portions 2126. Such a lateral force may be applied to the nasal region 2168 when the width of a user's nose is such that the nose sealing surface is deformed or deflected laterally outwards. This may happen, for example, when a user has a nose width that is on the large side for the particular seal size. In some embodiments, the thin pocket 2224 may also enable the upwardly extending portions to inflate under positive pressure. This may increase engagement between the nasal region 2168 and the user's nose and therefore improve the seal. On the other hand, the thickened rib 2222 is configured to provide support to reduce or limit creasing in the nasal region 2168 when a downwards force is applied to the upper surface 2130 of the nasal region 2168 resulting in some deformation of the seal 2104, as shown in FIG. 22C. The downward force may cause the upwardly extending portions 2126 to be drawn inward towards the user's nose in use. If excessive downward force is applied, the nasal region 2168 can collapse inwardly, and sometimes at least partially towards the front of the seal. The thickened ribs 2222 may support the nasal sealing surfaces 2124A and 2124B, such that the ribs 2222 help the upwardly extending portions 2126 to roll inward, providing resistance to creasing, whilst still allowing the seal 2104 to adapt to different facial geometries.

Figure 29:
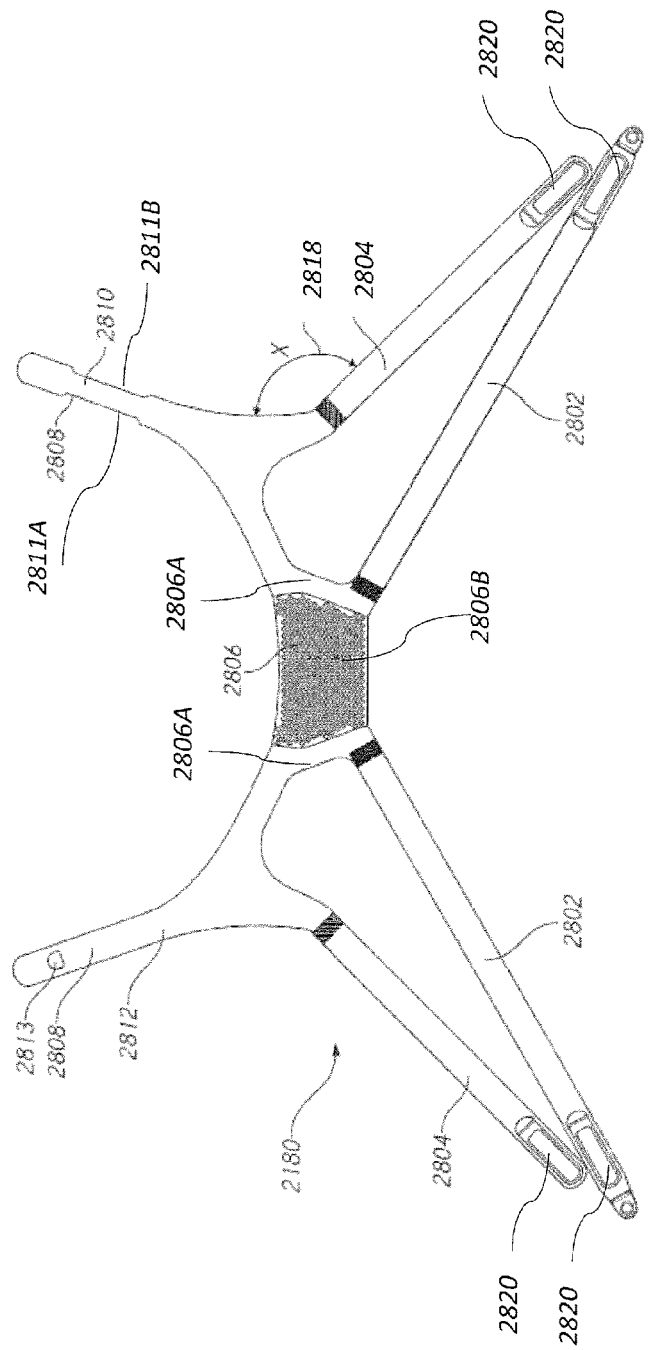
FIG. 29 is an exterior surface view of the headgear assembly of FIG. 28 in a laid flat orientation.
Figure 30:
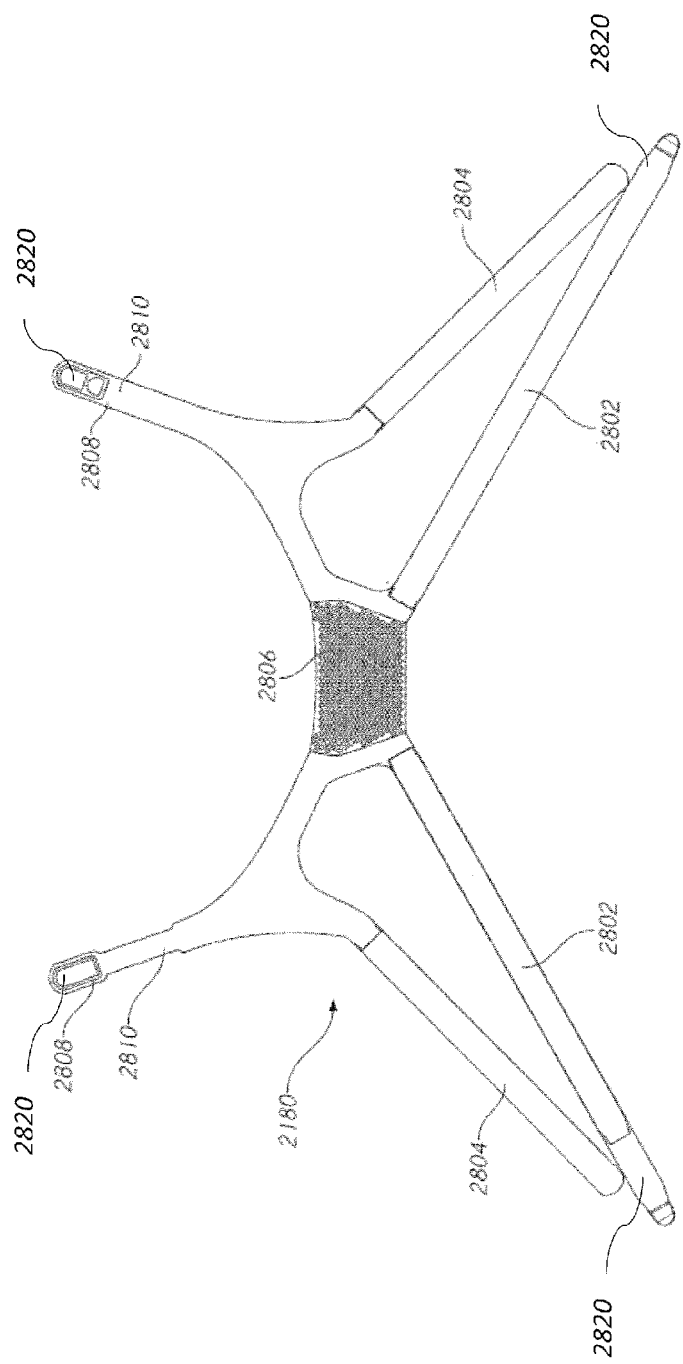
FIG. 30 is an interior surface view of the headgear assembly of FIG. 28 in a laid flat orientation.

FIG. 28 illustrates a side view of the patient interface showing an embodiment of the headgear 2180. FIG. 29 illustrates an exterior plan view of an external surface of the headgear 2180 and FIG. 30 illustrates an interior plan view of an interior surface of the headgear 2180, with the headgear 2180 laid flat in both FIGS. 29 and 30. As mentioned above, the headgear 2180 can include a strap assembly including at least two upper side straps 2804, at least two lower side straps 2802, a rear panel 2806, and/or a crown strap 2808, among other components or portions. As shown in at least FIGS. 29 and 30, the upper side straps 2804 can be connected to the crown strap 2808 at an angle 2818. For example, the angle 2818 between the upper side straps 2804 and the crown strap 2804 can be approximately 144 degrees. In some embodiments, the angle 2818 is 130 degrees, 135 degrees, 140 degrees, 145 degrees, or 150 degrees or more. The angle 2818 allows the upper side straps 2804 to extend downwardly above the user's ears to the frame 2178 in use.

In use, the upper sides straps 2804 can be positioned on opposite sides of the headgear 2180 and can extend downwardly from the crown strap 2808 towards the mask assembly 2100. In some embodiments, the upper side straps 2804 can be configured to extend across the user's cheeks when worn. In some embodiments, the upper side straps 2804 can be adjustably and/or directly connected to the frame 2178, such as at the upper strap connectors 2702 of the frame 2178.

In some embodiments, the lower side straps 2802 can be positioned on opposite sides of the headgear 2180. In use, the lower side straps 2802 can extend substantially horizontally below the ears of the user. The lower side straps 2802 can extend from the rear panel 2806 to or towards the mask assembly 2100. In some embodiments, the lower side straps 2802 can be configured to extend across the user's face when worn such as generally along the jaw of the user. In some embodiments, the lower side straps 2804 can be adjustably connected to the frame 2178. The connection between the frame 2178 and the lower side straps 2802 can include a direct and/or an indirect connection. For example, the lower side straps 2802 can be indirectly connected to the frame 2178 via the headgear clips 2600.

As shown in FIGS. 28-30, the upper and lower side straps 2804, 2802 can be connected by the rear panel 2806. The connection between the upper and lower side straps 2804, 2802 at the rear panel 2806 can be positioned rearward of the user's ear in use. Such configurations can provide stability and support to the headgear 2180. Such configurations can be more comfortable to the user when worn and/or provide a more aesthetically pleasing appearance.

In some embodiments, the rear panel 2806 can be positioned at approximately the center of the headgear 2180. The rear panel 2806 can be configured to contact a rear portion of the user's head when worn. In some embodiments, the rear panel 2806 can include at least two or more portions. The rear panel 2806 can include a first portion 2806A and a second portion 2806B. The first portion 2806A can be integrally formed with one or both of the upper and lower side straps 2804, 2802. In the illustrated arrangement, the first portion 2806A is made up of two separate sections, which may be spaced-apart by the second portion 2806B. In some embodiments, the second portion 2806B can be positioned at approximately the center of the rear panel 2806. The second portion 2806B can be made at least in part by spacer fabric. An example of such a spacer fabric is disclosed in Applicant's publication no. WO 2017/021836, the entirety of which is incorporated by reference herein. The spacer fabric can provide additional comfort to the user. For example, the spacer fabric can be desirably light weight, breathable and/or form a cushioned region at the rear of the user's head. In some embodiments, the spacer fabric of the second portion can extend inwardly from the first portion 2806A of the rear panel 2806. In some embodiments, the spacer fabric can include two spacer fabric layers. For example, each of the layers can be layered on top of the other.

As described above, in some embodiments the headgear 2180 includes the crown strap 2808. The crown strap 2808 can include a right portion 2810 and a left portion 2812. In some embodiments, the left and right portions 2812, 2810 can form a strap that extends across an upper region of the user's head, such as the crown of the user's head.

In some embodiments, the left and right portions 2812, 2810 can be adjustably coupled. In some embodiments, the left and right portions 2812, 2810 are adjustably coupled by a buckle. In some embodiments, the left portion 2812 includes an aperture 2813. The aperture 2813 can be positioned near an end of the left portion 2812 of the crown strap 2808. In some embodiments, the aperture 2813 can receive at least a portion of the right portion 2810 of the crown strap 2808. In some embodiments, the aperture 2813 allows the left portion 2812 and the right portion 2810 to be adjustably coupled. For example, the left and right portions 2812, 2810 can be slidably adjusted relative to one another.

In some embodiments, the right portion 2810 includes a first recessed region 2811A and a second recessed region 2811A. The first and second recessed regions 2811A, 2811B can be formed along opposite sides of the right portion 2810. The first and second recessed regions 2811A, 2811B can be aligned with one another and positioned offset from an end of the right portion 2810. In some embodiments, the first and second recessed regions 2811A, 2811B define a region of reduced width. The region of reduced width can slide through the aperture 2813. In some embodiments, the region of reduced width can slide through the aperture 2813 with no deformation or little deformation of the left and/or right portions 2812, 2810.

Although the left portion 2812 is illustrated as having the aperture 2813 and the right portion 2810 as having the first and second recessed regions 2811A, 2811B, other configurations are contemplated. For example, the right portion 2810 can include the aperture 2813 and the left portion 2812 can include the first and second recessed regions 2811A, 2811B.

In some embodiments, the upper side straps 2804, the lower side straps 2802, and/or the crown strap 2808 can include fastening features 2820. The fastening features 2820 can include one or more of a hook and a loop fastener, among other features. The fastening features 2820 can allow the headgear to be adjusted at various lengths, such as user-defined lengths. In some embodiments, the fastening features 2820 of the lower side straps 2802 and/or the upper side straps 2804 can allow the straps 2802, 2804 to be easily adjusted and/or removed from the mask assembly 2100.

Figure 31A:
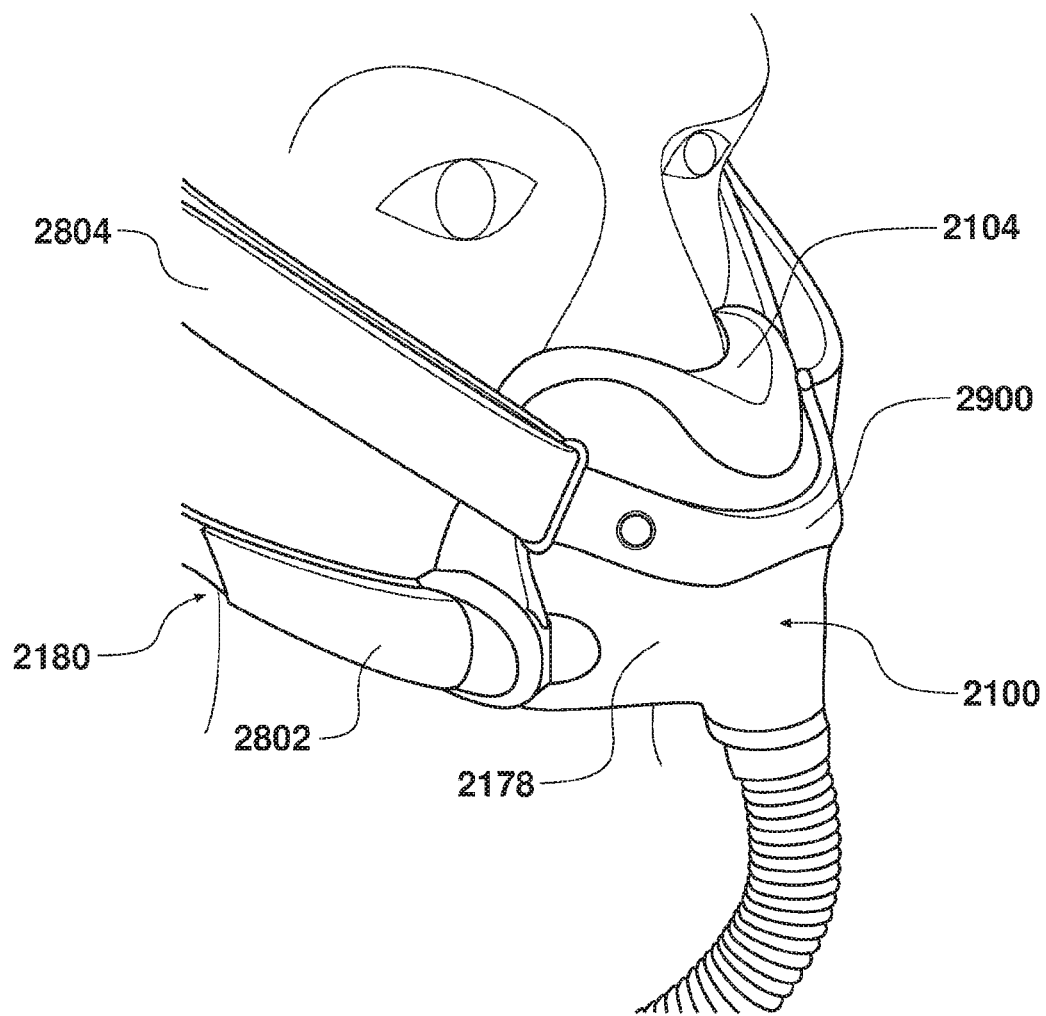
FIG. 31A is a front, top, and side perspective view of an interface assembly including a mask assembly and a headgear assembly with a yoke.
Figure 31B:
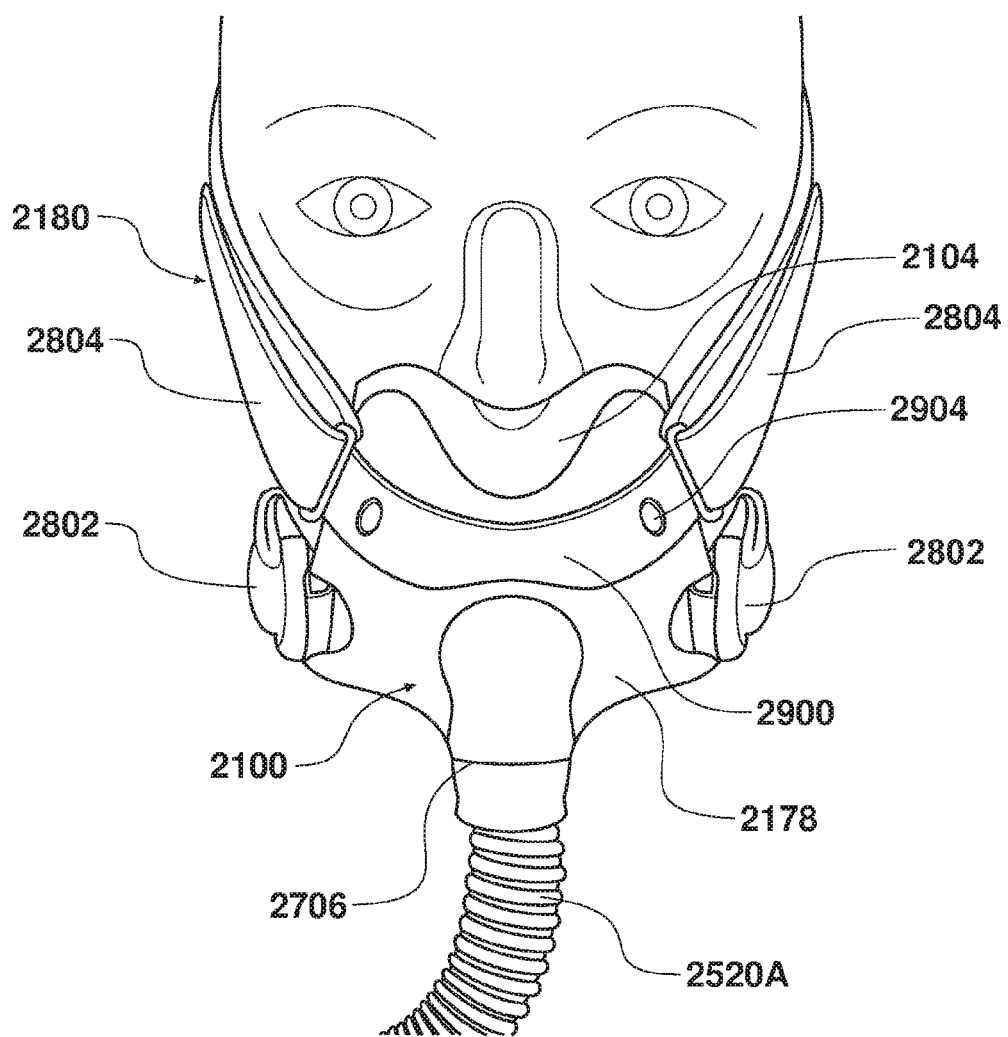
FIG. 31B is a front and top perspective view of the interface assembly of FIG. 31A.

FIGS. 31A-B illustrates an embodiment of an interface assembly including the headgear assembly 2180 similar to the headgear assemblies described elsewhere herein. FIG. 31A is a front, top, and side perspective view of the interface assembly and FIG. 31B is a front and top perspective view of the interface assembly. Among other components, the headgear assembly 2180 can include at least two upper side straps 2804, at least two lower side straps 2802, which may be similar with corresponding components of the headgear assemblies described elsewhere in the specification and the headgear assembly 2180 can be attached to a frame 2178 and a mask assembly 2100 including a seal 2104. As described in relation to FIGS. 3A-11, the frame 2178 may include an air inlet or conduit connector portion 2706, connected to an air supply conduit 2520A.

Additionally, the headgear assembly 2180 may also include headgear connector element 2900. The headgear connector element may be in the form of a tether or yoke. As illustrated in FIGS. 31A-B, the headgear connector element 2900 may be an elongate flexible member that couples the upper side straps 2804 to the frame 2178. The headgear connector element 2900 may extend laterally across the frame 2178 below a tip of a user's nose when coupled to the frame 2178, such that interference between the headgear straps 2800 and the upwardly extending portions 2126 is prevented. The headgear connector element 2900 may further provide the correct force vectors to the seal 2104 on the underside of the user's nose. The headgear connector element 2900 may be placed between the upper side straps 2804 and connect two upper side straps 2804. The headgear connector element 2900 may be removably attached to the frame 2178, thereby also removably attaching the upper side straps 2804 connected to the headgear connector element 2900 to the frame 2178.

In some embodiments, the headgear connector element 2900 may be constructed of a flexible material, such that the headgear connector element 2900 can bend and comply with the curvature of the frame 2178 when the headgear connector element 2900 is attached to the mask assembly 2100. In some embodiments, the headgear connector element 2900 may be constructed of an elastomeric material, such as a silicone or thermoplastic elastomer (TPE), such as a material sold under the Pebax® 2533 name. The frame 2178 may include fasteners 2904 which are configured to retain the headgear connector element 2900 when the headgear connector element 2900 is removably attached to the frame 2189. The fasteners 2904 and the headgear connector element 2900 may include any suitable mechanical connection, for example, a male/female or button/hole interlocking arrangement.

Figure 32:
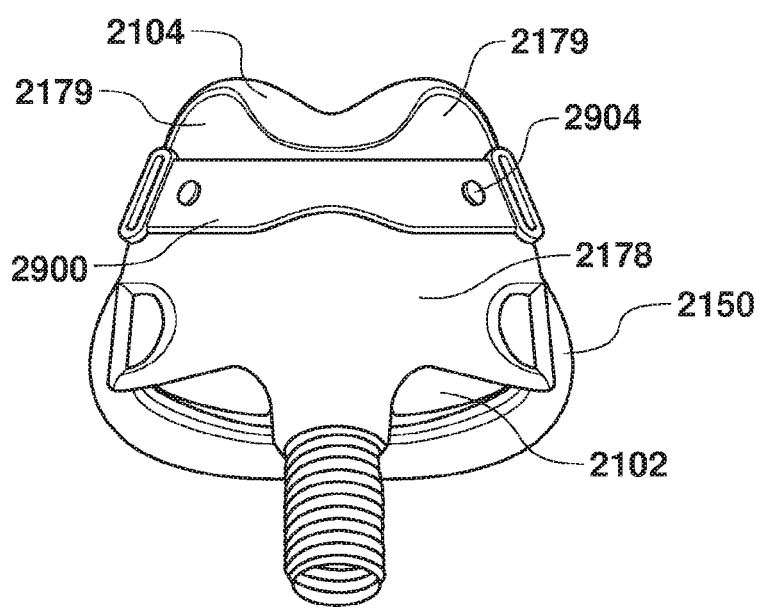
FIG. 32 is a front view of the mask assembly of the interface assembly of FIG. 31A with the yoke.

FIG. 32 illustrates a front view of the headgear connector element 2900, without the upper side straps 2804 shown, attached to the frame 2178 which is assembled to the mask assembly 2100, which can have a cushion module 2150 comprising the housing 2102 and the mask seal 2104. As illustrated in FIG. 32, the headgear connector element 2900 may be positioned below an upper edge of the frame 2178, such that at least part of the upwardly extending supports 2179 of the frame 2178 extend above the headgear connector element 2900. In some embodiments, the upwardly extending supports 2179 may work as a backing structure for the headgear connector element 2900, such that the headgear connector element 2900 is spaced from the seal 2104. In some embodiments, the headgear connector element 2900 may curve upwardly toward the upwardly extending supports 2179. The headgear connector element 2900 may have a length that is less than a width of the frame 2178, such that the headgear connector element 2900 is positioned laterally within the lateral edges of the frame 2178, thereby inhibiting or preventing the headgear connector element 2900 or its rigid components such as strap loops 2940 (described in detail below) from contacting the seal 2104 or the user's face.

Figure 33A:
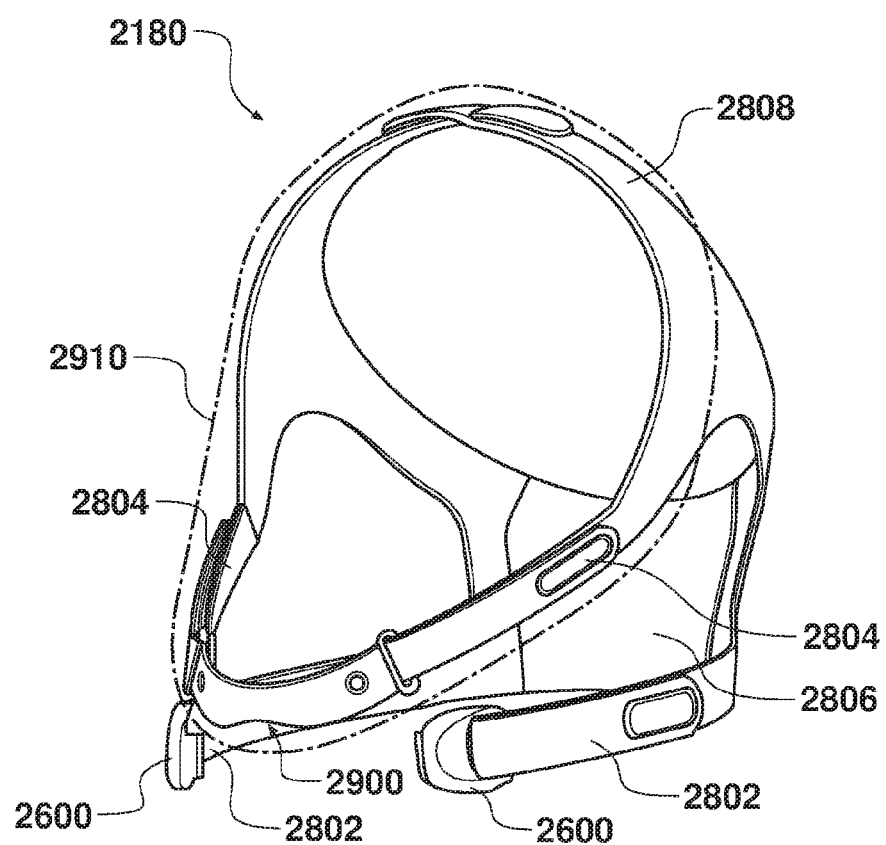
FIG. 33A is a front and side perspective view of the headgear assembly of the interface assembly of FIG. 31A with the yoke.
Figure 33B:
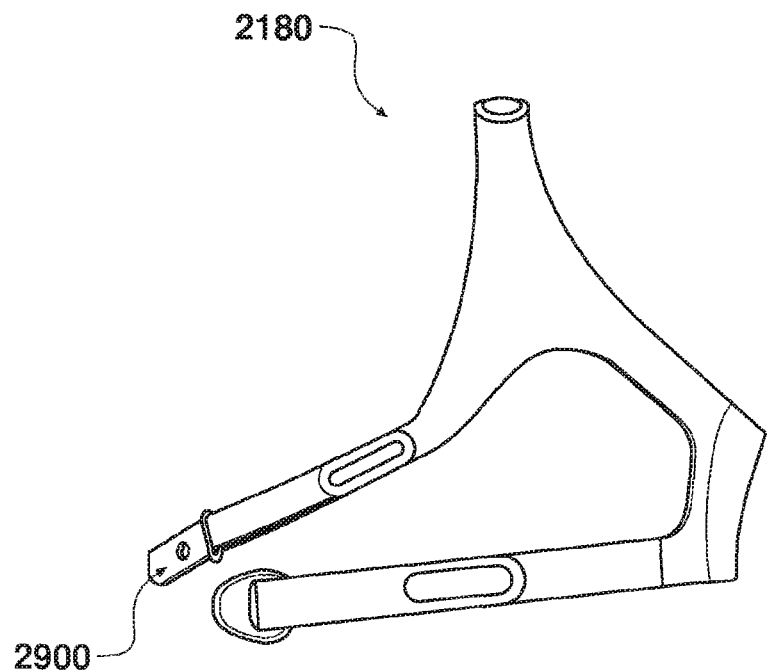
FIG. 33B is a side view of the headgear assembly of FIG. 33A.
Figure 33C:
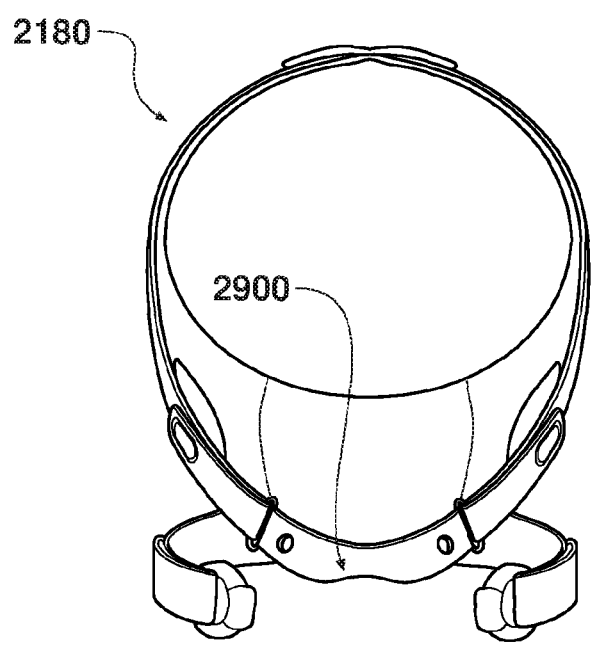
FIG. 33C is a front view of the headgear assembly of FIG. 33A.

FIGS. 33A-C illustrate a front and side perspective view, a side view and a front view of the headgear 2180 including the headgear connector element 2900, respectively. The headgear assembly 2180 can include a strap assembly including at least two upper side straps 2804, at least two lower side straps 2802, a rear panel 2806, and/or a crown strap 2808, among other portions or components. The components of the headgear 2180 may be similar with the components of the headgear described in relation to FIGS. 28-30. For example, the upper side straps 2804 can be connected to the crown strap 2808, and the lower side straps 2802 include headgear clips 2600 at their free ends to be coupled to the frame 2178. Also as described above, the upper side straps 2804 may be also connected to the headgear connector element 2900, such that such that the upper side straps 2804, the headgear connector element 2900 and the crown strap 2808 form a closed loop 2910. In some embodiments, as shown in FIG. 33A, the upper side straps 2804 may be connected to the headgear connector element 2900 even when the yoke is detached from the frame 2178, such that the closed loop 2910 formed by the upper side straps 2804, the headgear connector element 2900 and the crown strap 2808 is maintained when the headgear 2180 is detached from the frame 2178. This allows the user's fitment/sizing settings to be retained when the headgear assembly 2180 and the headgear connector element 2900 is disconnected from the frame 2708, for example, for cleaning. Accordingly, it would be quicker and easier for the user to fit the interface as the straps do not need to be re-adjusted. Further, the headgear connector element 2900 may hold apart free ends of the upper side straps 2804 and prevent them from hanging loose and swinging freely when the headgear assembly 2180 is decoupled from the frame 2178. Such an arrangement makes it easier to couple the headgear assembly 2180 to the frame 2178.

Figure 34C:
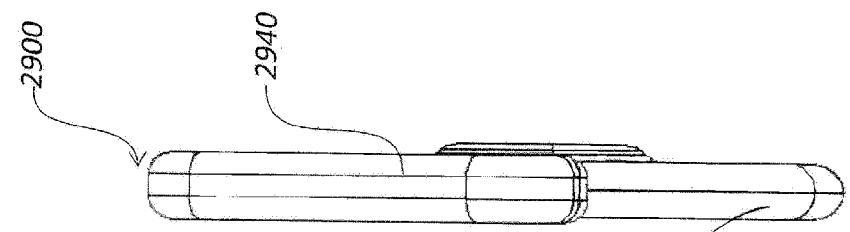
FIG. 34C is a side view of the yoke of the interface assembly of FIG. 31A.
Figure 34A:
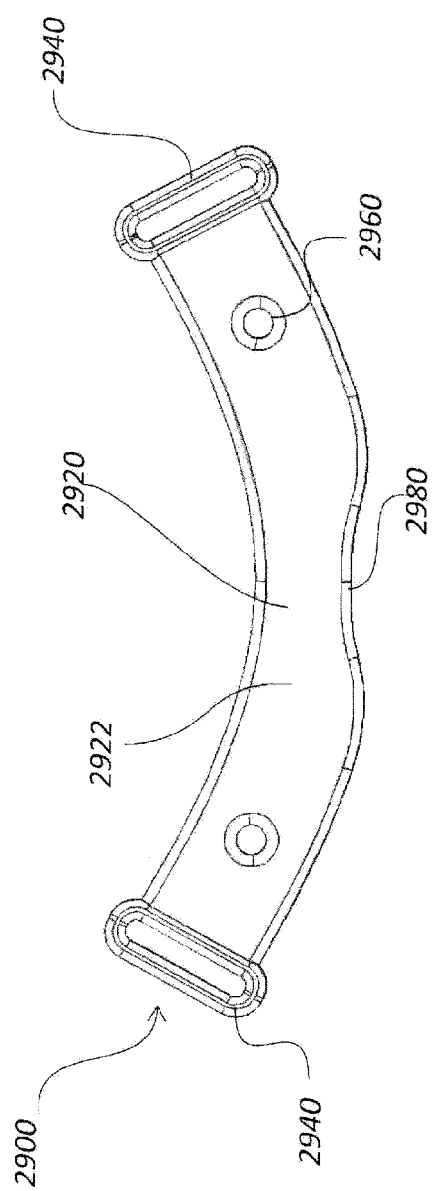
FIG. 34A is a front view of the yoke of the interface assembly of FIG. 31A.
Figure 34B:
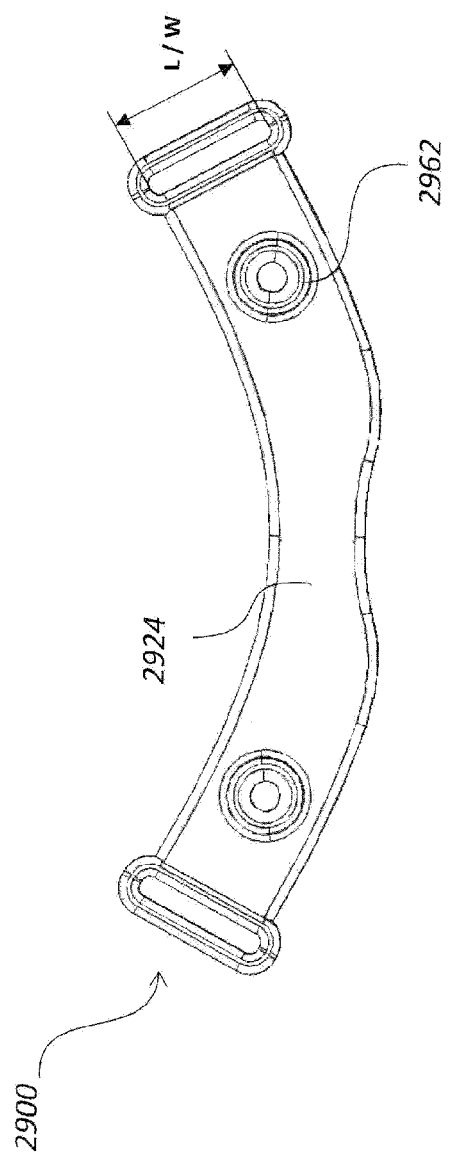
FIG. 34B is a rear view of the yoke of the interface assembly of FIG. 31A.

FIGS. 34A-G illustrates an embodiment of the headgear connector element 2900. FIGS. 34A-C illustrate the front view, the rear view, and the side view of the headgear connector element 2900, respectively. The headgear connector element 2900 may include a main body portion ("main body") 2920, and strap loops 2940 at each of the ends of the main body 2920. The main body 2920 may be substantially flat and/or planar, and may have a rearward-facing surface 2924 configured to face the frame 2178 when the headgear connector element 2900 is attached to the frame 2178, and a forward-facing surface 2922 opposite the rearward-facing surface 2924. Even though the headgear connector element 2900 may be relatively flat or planar in its natural configuration, its flexibility may enable it to be bent to conform to the curvature of the frame 2178. Being formed as a flat component provides the headgear connector element 2900 with a resilience which biases it towards its flat natural configuration. This resilience may help the headgear assembly 2180 to maintain an open configuration when it is not attached to the mask, as illustrated in FIGS. 33A-C. Further, the main body 2920 may have sufficient level of stiffness to allow it to be securely snapped onto and retained by the fasteners 2904.

In the illustrated embodiment, the main body 2920 includes a recess or concave portion 2980 in the center of the lower edge. The concave portion 2980 may improve aesthetic appeal by passing above a boss of the air inlet 2706, rather than overlapping with it. Further, the concave portion 2980 reduces a width of a central portion of the body 2920 and therefore minimizes bulk at the front of the interface assembly, providing a less obtrusive appearance. The reduced width of the central portion of the body 2920 may also help the headgear connector element 2900 bend to conform to the surface contour of the frame 2178. In some embodiments, the body 2920 may not include the concave portion and the upper edge and the lower edge of the body 2920 may extend at least substantially parallel to each other.

The strap loops 2940 may have any suitable shapes/dimensions to receive and retain the upper side straps 2804. For example, in some embodiments, a free end of each of the upper side straps 2804 may be threaded through one of the strap loops 2940, folded back on itself and secured to itself at a user defined location to set the size of the headgear 2180. The upper side straps 2804 may be secured about the loops 2940 using any suitable fasteners known in the art, for example, a hook and loop fastener or Velcro®. The strap loops 2940 may have an internal slot with a length L, which can be substantially the same as or larger than a width of the upper side straps 2804, such that the upper side straps 2804 are not kinked when coupled to the loops 2940. Further, the main body 2920 may have a width W that is substantially similar to or is the same as a width of the upper side straps 2804, such that the headgear connector element 2900 and the upper side straps 2804 have an appearance similar to a single strap that extends all the way around the user's head and the mask assembly 2100. In the illustrated embodiment, the headgear connector element 2900 is upwardly concave-shaped such that the strap loops 2940 are angled upwards, thus when the upper side straps 2804 are coupled to the strap loops 2940, straps 2804 are directed upwards to pass between the user's ears and eyes. However, the headgear connector element 2900 and the body 2920 may have any suitable shape to conform to the frame 2178, and to direct the upper side straps 2804 in desirable directions.

The strap loops 2940 may be formed of a more rigid material than the main body 2920, such that the strap loops 2940 maintain their shape when coupled to the straps 2804.

Further, the strap loops 2940 may have a low friction surface finish which enables the upper side straps 2804 to slide smoothly through the loops 2940. In some embodiments, the strap loops 2940 may include a higher frictions surface, or the strap loops 2940 are shaped and/or sized to provide some interference with the straps, such that the straps 2804 do not fall freely through the strap loops 2940. Such interference between the strap loops 2940 and the straps 2804 may enable the straps to remain assembled to the headgear connector element 2900 even when the straps are not folded back and fixed to themselves, therefore improving the ease with which the straps 2804 are fitted and adjusted.

Figure 34D:
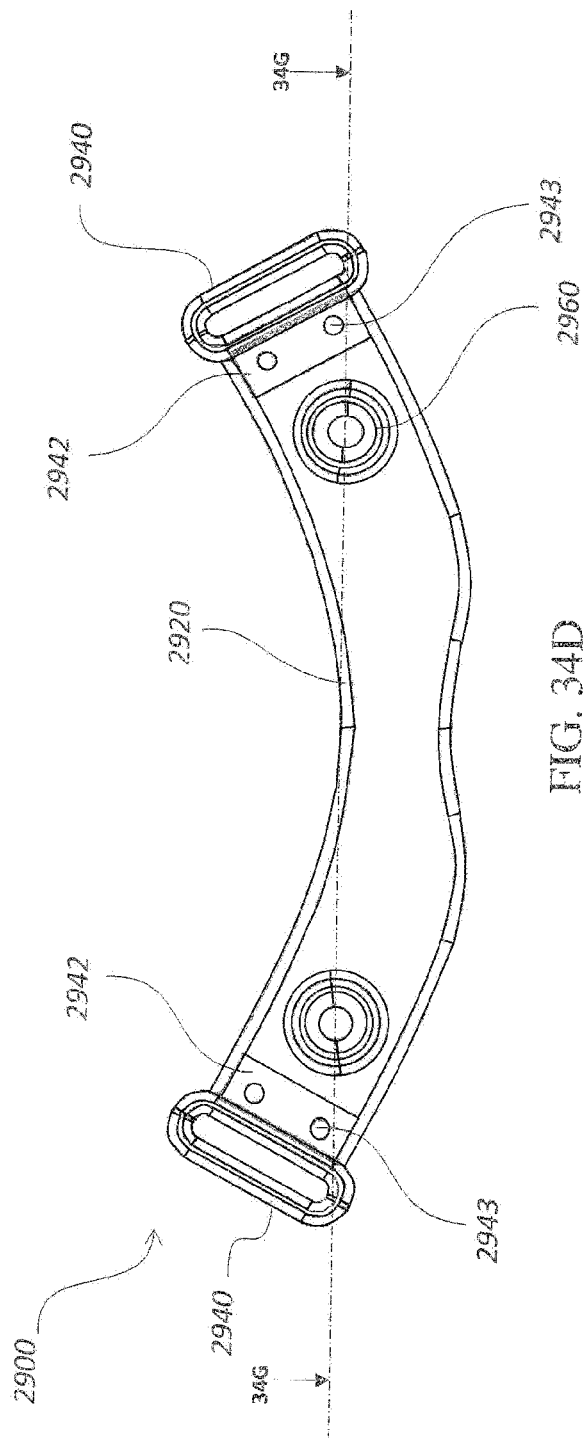
FIG. 34D is a view of the yoke of the interface assembly of FIG. 31A with a portion of the yoke shown in outline form to illustrate underlying structure.

In some embodiments, the strap loops 2940 may be formed of a material different than a silicone or a thermoplastic elastomer (TPE), such as nylon. In some embodiments, the strap loops 2904 may be constructed, for example by moulding, as separate component from the body 2920 and later coupled with the body 2920 to form the headgear connector element 2900. FIG. 34D illustrates a view of the headgear connector element 2900 in which the main body 2920 is shown in outline to illustrate an example of an arrangement for coupling the strap loops 2940 and the main body 2920. In the illustrated embodiment, the main body 2920 may be over-moulded onto the strap loops 2940 at overmoulding tabs 2942 extending from one side of each of the strap loops 2940. In some embodiments, the over-moulding tabs 2942 may have one or more holes 2943 through them to form a mechanical interlock with the over-moulded material of the main body 2920. Since the strap loops 2940 and the over-moulding tabs 2942 may serve as over-moulding substrates, they may be made of a highly stiff material, thereby inhibiting or preventing the over-moulding tabs 2942 from flexing or otherwise distorting and, as a possible result, bursting through the overmoulded region during the over-moulding process. In some embodiments, the over-moulding tabs 2942 may include additional support to prevent the tabs 2942 from flexing and bursting through the over-moulded region. Additionally or alternatively to the over-moulding, in some embodiments, the strap loops 2940 and the main body 2920 may be coupled by adhesives and/or heat-welded, for example.

In some embodiments, the main body 2920 may further include one or more fastener apertures 2960 in the form of eyelets to receive the fasteners 2904 of the frame 2178. In the illustrated embodiment, the main body 2920 has two apertures 2960 to receive two fasteners 2904. In some embodiments, the headgear connector element 2900 and the frame 2178 may have three or more apertures 2960 and fasteners 2904, such that there are more points of attachment for additional coupling or more secure coupling of the headgear connector element 2900 to the frame 2178. The apertures 2960 may have any appropriate shapes which can receive and retain the fastener 2904. For example, as in the illustrated embodiment, the apertures 2960 and the fasteners 2904 may have a circular shape. As shown in FIG. 34B, the headgear connector element 2900 may also include one or more rims 2962 which are located around and surround each of the apertures 2960. The rims 2962 may be constructed of stiffer or more resilient material, such that the rims 2962 can help the apertures 2960 withstand a large number of attachment/removal cycles of the headgear connector element 2900. In some embodiments, the rims 2962 may be formed of a material same as the body 2920. In some embodiments, the rims 2962 may be constructed of thermoplastic elastomer (TPE). In some embodiments, the rims 2962 may have a greater thickness than the main body 2920. Since the rims 2962 may be thicker than the main body 2920, it may protrude out of the main body 2920. In the illustrated embodiment, the thickened rims 2962 are provided only on the rear surface 2924 of the headgear connector element 2900, such that they are not visible once the headgear connector element 2900 is coupled to the frame 2178. In some embodiments, the rims 2962 may be formed on the front side surface 2922, or on both the front and the rear surfaces 2922, 2924.

Figure 35A:
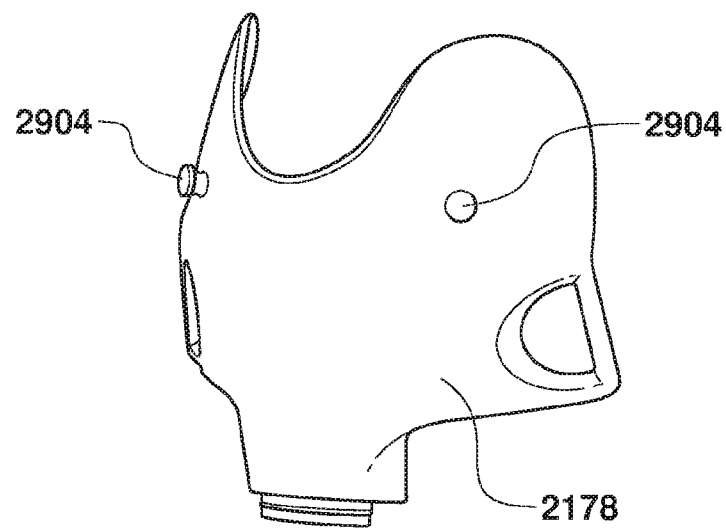
FIG. 35A is a front and side perspective view of the frame of the interface assembly of FIG. 31A.

FIG. 35A illustrates an embodiment of the frame 2178 having the fasteners 2904. In the illustrated embodiment, the frame 2178 includes two male fasteners 2904 that protrude from a front surface of the frame 2178. Each male fastener 2904 is configured to pass through one of the apertures 2960 in the headgear connector element 2900 to fasten the headgear connector element 2900 to the frame 2178. However, the fasteners 2904 and the apertures 2960 may be replaced with any removable attachment mechanisms known in the art. For example, in some embodiments, the frame 2178 may have female components while the headgear connector element 2900 may have male components. The frame 2178 and the headgear connector element 2900 may have other mechanical connection mechanisms. For example, the headgear connector element 2900 may be configured to be push fit into a slot on the frame 2178, the headgear connector element 2900 may be configured to stretch fit across the frame 2178, or the headgear connector element 2900 and the frame 2178 may have sliding glider type arrangement. In one such sliding glider type arrangement, one or more attachment members (e.g., filaments or strips) of the headgear connector element 2900 are received by one or more suitable receptacle structures (e.g., cavities) of the frame 2178 such that some amount of relative sliding movement between the headgear connector element 2900 and the frame 2178 is permitted. In some embodiments, the headgear connector element 2900 and the frame 2178 may be coupled by one or more hook and loop fasteners.

Figure 35B:
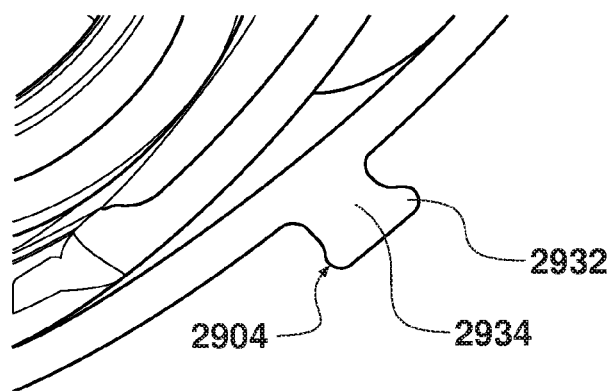
FIG. 35B is an enlarged cross-sectional view of a portion of the frame of FIG. 35A.

As shown in FIG. 35B, which illustrates an enlarged cross-sectional view of the frame 2178, each of the male fastener components 2904 includes a post 2934 with an enlarged head 2932 at the top end of the post 2934. The enlarged head 2932 may have greater cross-sectional diameter/area than the aperture 2960 of the headgear connector element 2900. The enlarged head 2932 may be in the form of a flange extending from the perimeter of the post. The enlarged head 2392 may form a substantially planar surface facing outward away from the frame. In some embodiments, the enlarged head 2932 may be laterally offset or asymmetric relative to the post 2934. The enlarged heads 2932 of respective posts may be asymmetric in opposed directions. The asymmetry of the enlarged head 2932 may help the headgear connector element 2900 be fastened to the frame 2178 and prevent the ends of the headgear connector element 2900 from popping off the frame. Further, this design may improve manufacturability of frame 2178 by simplifying the draw planes of the mould tool. The height of the fastener component 2904 (i.e. distance that it protrudes from the front surface of the frame 2178) may be determined by the draw planes of the mould tool. In the illustrated embodiment, the fastener 2904 has a height of 3.5 mm. In some embodiments, the fastener 2904 may have a height greater or less than 3.5 mm, for example, 2-10 mm, 3-7 mm, or 3-4 mm.

Figure 34E:
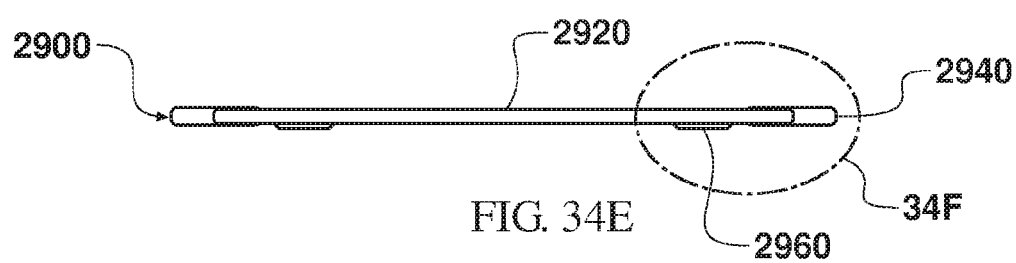
FIG. 34E is a bottom view of the yoke of the interface assembly of FIG. 31A.
Figure 34F:
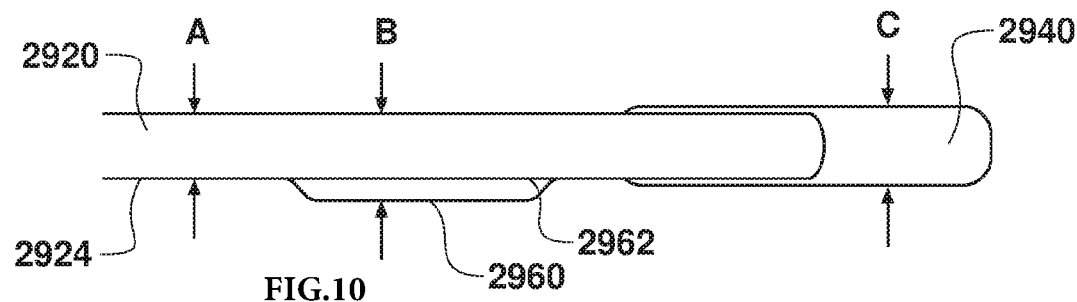
FIG. 34F is an enlarged view of a portion of the bottom of the yoke of the interface assembly of FIG. 31A as identified in FIG. 34E.

With reference to FIG. 34E, which is a bottom view of the headgear connector element 2900, the headgear connector element 2900 may have a varying thickness along its length. In some embodiments, such as shown in FIG. 34F, the main body 2920 may be the thinnest region with a thickness A of, for example, 2.5 mm. In some embodiments, the main body 2920 may have thickness of 1-5 mm, 1.5-4 mm, or 2-3 mm. The thickness of the main body 2920 may be selected to provide the desired degree of flexibility, in combination with the properties of the elastomeric material forming the main body 2920. In some embodiments, the main body 2920 may have at least substantially constant thickness along its length. In some embodiments, a portion of the main body 2920, for example a central portion of the main body 2920, may have less thickness, so that such portion would be more flexible to help the bending of the headgear connector element 2900.

As shown in FIG. 34F, which is an enlarged view of the headgear connector element 2900 shown in FIG. 34E, and as described elsewhere in the specification, the thickness may be increased around the perimeter of the fastener aperture 2960 to form the thickened aperture rim 2962. In the illustrated embodiment, the rim 2962 may have a thickness B of 3.25 mm. In some embodiments, the rim 2962 may have a thickness of 1-7 mm, 2-5 mm, or 3-4 mm.

Figure 34G:
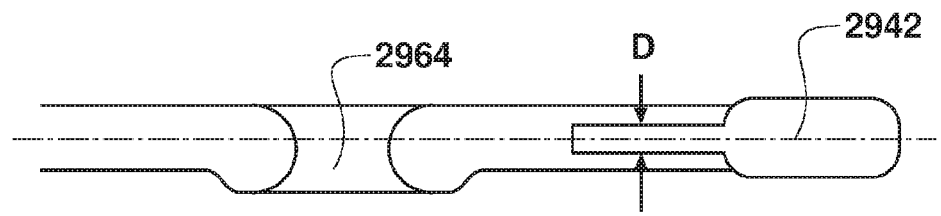
FIG. 34G is an enlarged view of a portion of a bottom cross-sectional view of the yoke of the interface assembly of FIG. 32A taken along the line 34G-34G of FIG. 34D.
Figure 36:
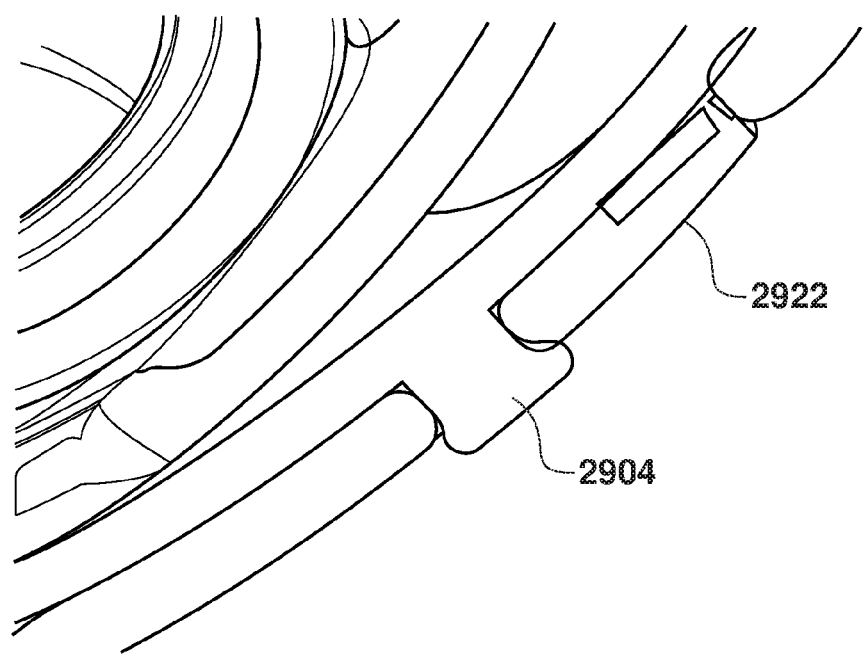
FIG. 36 is a close up of a cross-sectional view of a portion of the yoke and the mask assembly of the interface assembly of FIG. 31A.

The thickness of the rim 2962 may be determined based on the height of the male fastener posts 2934 to which they attach. In some embodiments, a top of the enlarged head 2932 may be flush with or relatively flush with the forward facing surface 2922 of the headgear connector element 2900 when the fasteners 2904 are coupled to the apertures 2960. This may provide a smoother look, and may also prevent the post 2934 from digging into a user's thumb or finger, and causing discomfort, when fastening the headgear connector element 2900 to the frame 2178. In some embodiments, the thickness B of the rim 2962 may be slightly less than the height of the fastener 2904, such that the apertures 2960 can fully pass over and be retained by the fastener 2904. Even though the thickness of the rim 2962 may be determined based on the height of the fastener posts 2934, it may be undesirable for the entire headgear connector element 2900 to have a thickness that matches the thickness of the rim 2962 or the height of the fastener 2904, as it may limit the flexibility of the headgear connector element 2900 and make the headgear connector element 2900 and the interface heavier and more expensive due to the increased material usage. Therefore, in some configurations, only the rim 2962 may be thickened. In some embodiments, an internal surface 2964 of the aperture 2960 may be at least partially toroidal shaped, as shown in FIG. 34G, which illustrates a cross-sectional view of the headgear connector element 2900 along the line 34G-34G of FIG. 34D. The internal surface 2964 can have a minimum diameter that substantially matches the outer diameter of the post 2934 of the male fastener 2904. As a result, temporary deformation of one or both of the post 2934 and the portion of the headgear connector element 2900 defining the aperture 2960 occurs when the headgear connector element 2900 is connected to the frame 2178 such that a snap-fit or interlocking connection is created. The diameter of the internal surface 2964 of the aperture 2960 may be larger at both the forward facing surface 2922 and rearward facing surface 2924 of the headgear connector element 2900. This provides a lead-in for the post 2934 and/or allows at least a portion of the head 2932 to be recessed into the headgear connector element 2900 upon complete assembly, such that the head 2932 does not protrude too far from the front surface 2922 of the headgear connector element 2900 and catch on objects, such as clothes. In some embodiments, the head 2932 may protrude beyond the forward facing surface 2922 of the headgear connector element 2900, as shown in FIG. 36.

The strap loops 2940 may have a thickness C which is greater than the main body 2920. In some embodiments, the thickness C may be less than the thickness B of the aperture rim 2962. In other embodiments, the thickness C may be the same as or greater than the thickness B. In the illustrated embodiment, the thickness C of the strap loops 2940 may be 3 mm. In some embodiments, the strap loops 2940 may have a thickness of 1-5 mm, 2-4 mm, or 2.5-3.5 mm. As shown in FIG. 34G, the over-moulding tab 2942 may have a reduced thickness D that is less than the thickness A of the main body 2920, such that the tab 2942 is fully encapsulated by the material of the main body 2920. In some embodiments, the over-moulding tab 2942 may have a thickness D of 1 mm. In some embodiments, the over-moulding tab 2942 may have a thickness D of 0.5-1.5 mm or any other suitable thickness.

Figure 37A:
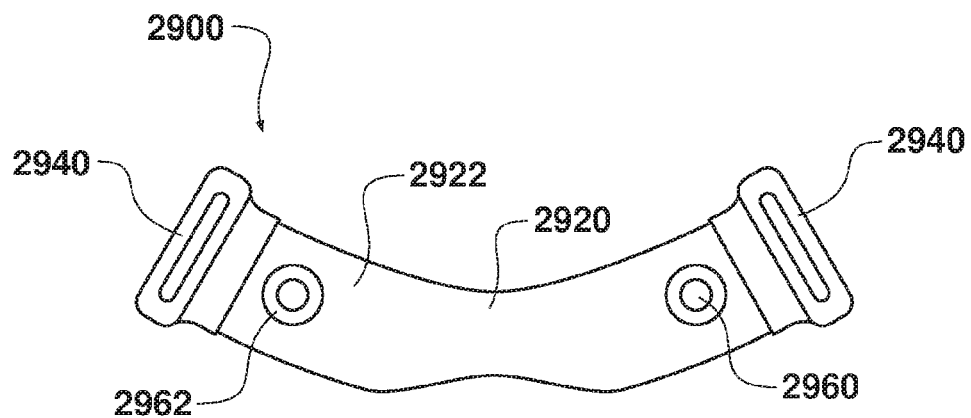
FIG. 37A is a front view of a yoke similar to the yoke of the interface assembly of FIG. 31A.
Figure 37B:
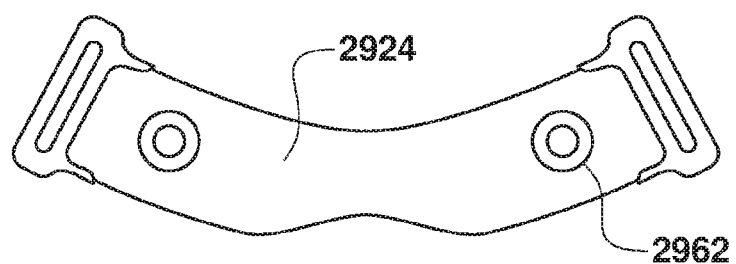
FIG. 37B is a rear view of the yoke of FIG. 37A.
Figure 38:
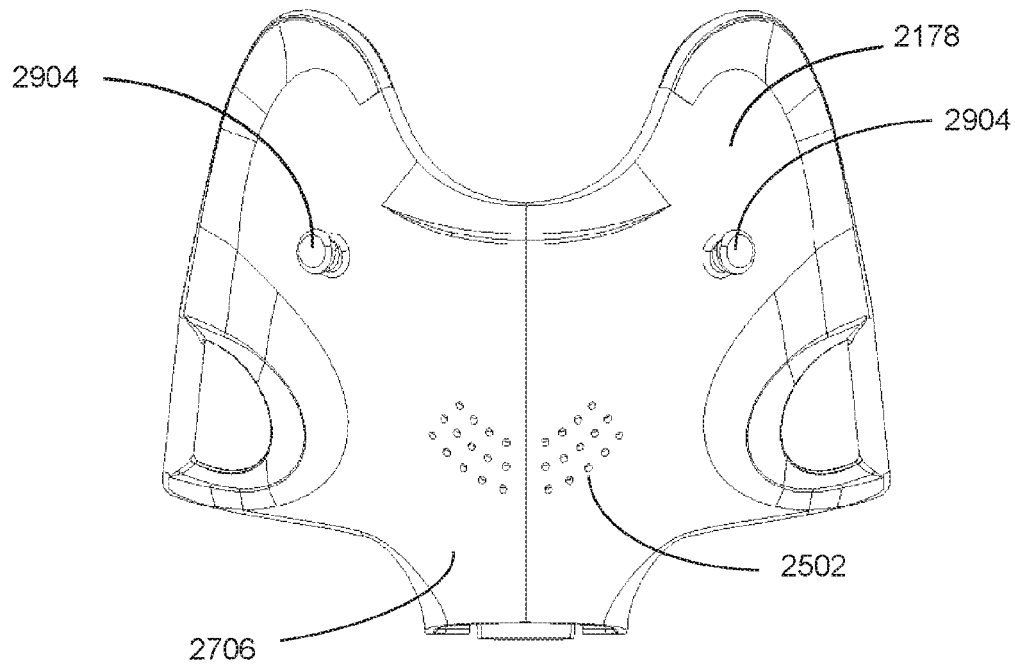
FIG. 38 is front view of a mask frame of an interface assembly in accordance with aspects of this disclosure.
Figure 39:
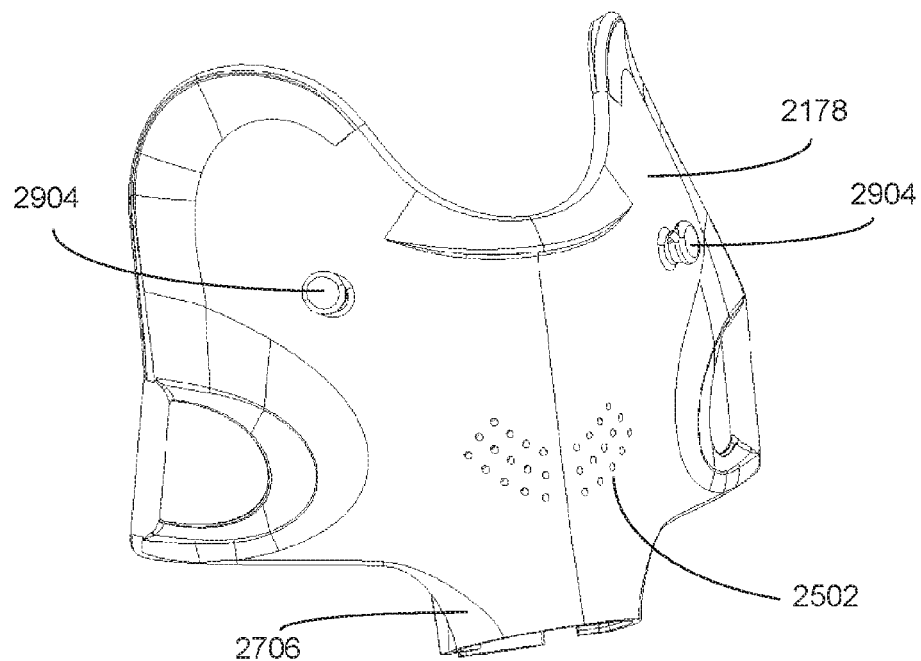
FIG. 39 is a perspective view of the mask frame of FIG. 38.
Figure 40:
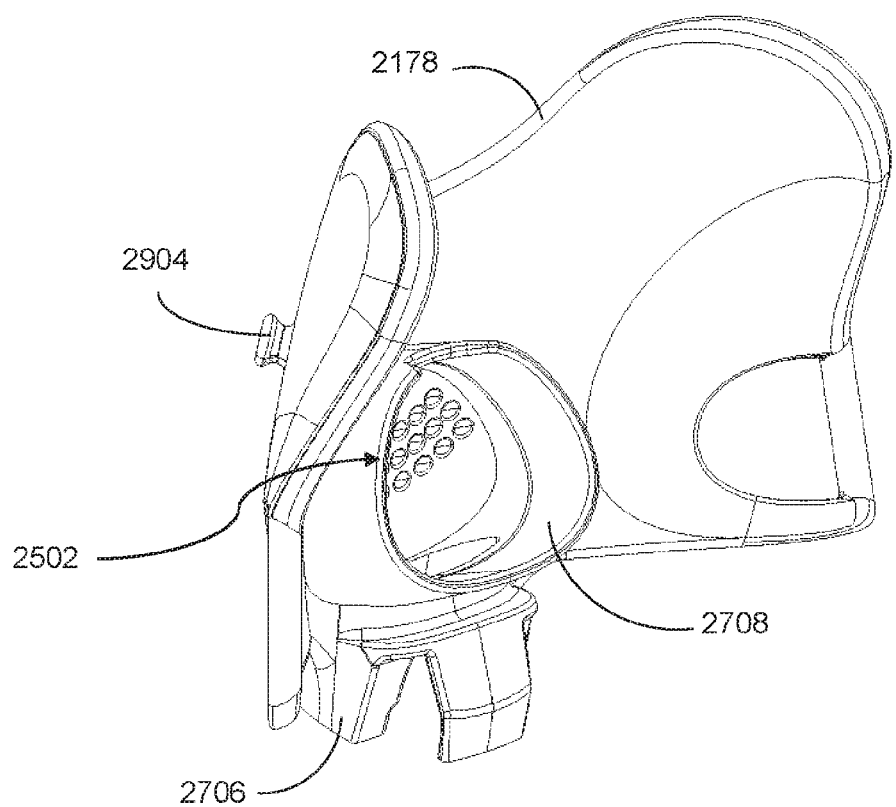
FIG. 40 is a side view of the mask frame of FIGS. 39 and 39.

FIGS. 37A-37B illustrates another embodiment of the headgear connector element 2900. Similar to the headgear connector element 2900 described in relation to FIGS. 31A-36, the headgear connector element 2900 may include the main body 2920, strap loops 2940 attached to each end of the main body 2920, and the apertures 2960. The body 2920 includes a front surface 2922 and a rear surface 2924. In the illustrated embodiment, the main body 2920 may be constructed of a foam and/or textile laminate, such as Breath-o-Prene®, and thus the main body 2920 may be more flexible than the main body 2920 constructed from TPE described above. In some embodiments, the forward-facing surface 2922 may be constructed of a textile material, while the rearward facing surface 2924 may be constructed of a foam material, such that the textile front surface 2922 of the main body 2920 provides continuity with the appearance and texture of the upper side straps 2804. In some embodiments, both of the forward-facing surface 2922 and the rearward facing surface 2924 may be constructed from one or more textile materials. The strap loops 2940 may be constructed of material stiffer than the main body 2920. In the illustrated embodiment, the main body 2920 may be welded onto the strap loops 2940. In some embodiments, the main body 2920 may be adhered to the strap loops 2940 by adhesives, or stitching.

As described elsewhere in the specification, the main body 2920 at the region of aperture 2960 may have certain level of stiffness to securely snap on the enlarged head 2932 of fastener 2904 and retain the fastener 2904. However, the main body 2920 constructed from textile laminate and/or foam may not have such level of stiffness. Therefore, the headgear connector element 2900 may have aperture rims 2962 made of stiffer materials. In some embodiments, the rims 2962 may be made of TPE, and may be formed as over-moulded grommets that extend through the apertures 2960 and protrude beyond both the forward and rearward facing surfaces 2922, 2924 of the main body 2920, such that the grommet 2962 provides reinforcement to the aperture 2960.

Referring now to FIGS. 38 to 87, various embodiments of mask assembly 2100 are shown comprising different configurations of bias vents 2502 and an associated diffuser. Some of these examples use a bias vent arrangement similar to the FIG. 14 example in which housing 2102 including two bias vents 2502 at a bottom margin of the housing 2012. Some of these examples use a different bias vent arrangement.

Further, in the embodiment of FIG. 31 a headgear connector element 2900 is provided in the form of a tether or yoke. As illustrated in FIGS. 31A-B, the headgear connector element 2900 may be an elongate flexible member that couples the upper side straps 2804 of the headgear to the frame 2178. As noted above, the headgear connector element 2900 may extend laterally across the frame 2178 below a tip of a user's nose when coupled to the frame 2178.

With reference to FIGS. 38 to 44, this embodiment may be modified such that the bias vents 2502 are provided on the mask frame 2178, and a diffuser 3000 is provided on the headgear connector element 2900. In this example the diffuser 3000 comprises a portion of diffuser material which is either mounted on the headgear connector element 2900, or is held in place between the mask frame 2178 and the headgear connector element 2900.

As described above, the headgear connector element 2900 is held in place on the mask frame 2178 by way of fasteners 2904 that engage corresponding apertures in the headgear connector element 2900.

The headgear connector element 2900 in this example is a planar piece of semi-rigid material such as plastic or silicone, which is flexed around the curved exterior front surface of the mask frame 2178. The headgear connector element 2900 includes a central main body 2920 shaped to provide a pair of opposed laterally extending arms 2920A extending from the central body 2090, and strap loops 2940 at each of the ends of the laterally extending arms 2920A of the main body 2920.

The headgear connector element 2900 therefore extends laterally across the mask frame 2178, has a centrally located window or aperture in main body 2920, and a pair of opposing lateral strap loops 2940. The headgear connector element 2900, curves downwardly from strap loops 2940 towards a central region to form a 'U' shape. The lower and central region of the headgear connector element 2900 is located in front of the vent holes of the bias vent 2502, when mounted on the mask frame 2178.

Figure 41:
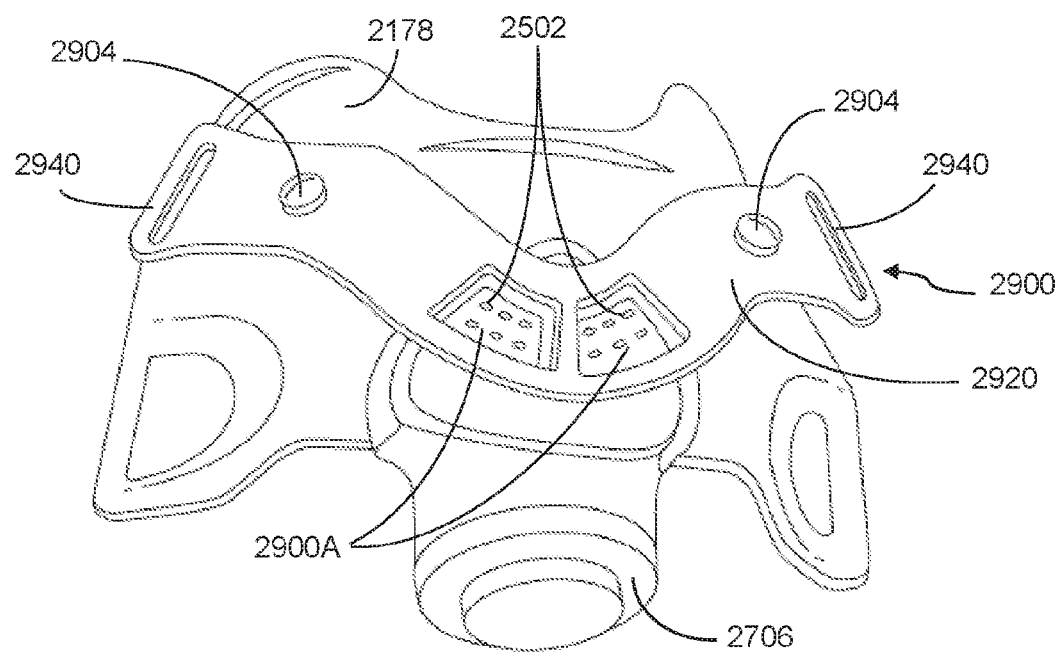
FIG. 41 is a front perspective view of the mask frame of FIGS. 38 to 40 and a yoke, with diffuser material omitted.

In this example, the headgear connector element 2900 is provided with one or more diffuser apertures 2900A, and in this case with a pair of such apertures 2900A, one on each side of the vertical centreline of the mask assembly 2100, as can best be seen in FIG. 41 (noting that in FIG. 41 the holes of the bias vent 2502 are not shown).

The diffuser apertures 2900A are arranged on headgear connector element 2900 to be aligned with the bias vents 2502 on the mask frame 2178. The bias vents 2502 therefore comprise two arrays of bias vent holes, the arrays being equispaced about the vertical centreline of the mask assembly 2100. The arrays are arranged to form a U or V shape on the mask frame 2178. The vent holes are located on the front surface of the mask frame 2178, above the inlet 2706 and below the fasteners 2904. The vent holes are oriented to direct exhaled air away from and reduce draft on the user's face and are positioned within the protruding boss that forms the cushion connector 2708 on the rear of the frame 2178. Any number of vent holes can be used, preferably of diameter between 0.5-3 mm configured to provide sufficient flushing of CO.

The air flow through the vent holes may have a high velocity (relative to the air that is inhaled by the user) that may lead to noise. This is at least partially addressed by the use of a diffuser 3000, which includes a portion of diffuser material that diffuses air, decreasing its velocity. Diffusion of air occurs as the composition of the diffuser material produces a tortuous path for the air. The diffuser material may be a single piece, or multiple pieces of appropriate material such as needle punched non-woven fabrics (e.g. felt). In one example, the diffuser material is formed as a diffuser mat made from a needle punched thermally bonded polyester (100% PET). Any other textile material or combination of materials could alternatively be used. The fibres comprising this material are entangled or mechanically interlocked, forming a tortuous path for the air passing through it. This disperses the air flow, reducing its velocity and therefore noise.

The diffuser apertures 2900A are covered by diffuser material (not shown) which may be in, on top of, or underneath, the apertures 2900A. The diffuser material diffuses bias flow through the bias vents 2502 and therefore may reduce noise, and may reduce or prevent any jetting or bias flow onto the user's face.

The diffuser material may be permanently mounted on the headgear connector element 2900, for example by overmoulding, adhesive, or a mechanical clip, or may be removably mounted, for example by way of, frictional engagement, clips or snap fit connectors or the like.

The diffuser 3000 is located on the exterior front surface of the headgear connector element 2900 to produce an offset distance between the diffuser material and vent holes. This offset ensures that the diffuser material, which holds some moisture due to the moist exhaled air, does not come into direct contact with the vent holes. When moist exhaled air hits/travels through the diffuser it can condense, causing moisture to be retained in the diffuser. Such moisture retention is undesirable. The offset between the diffuser material and vent holes prevents this moisture from coming into contact with the vent holes, or at least minimises or reduces such contact. This therefore minimises moisture from the diffuser material from moving to the vent holes and clogging or blocking them. The diffuser 3000 may alternatively be attached to the interior or rear surface of the headgear connector element 2900 with additional features on the headgear connector element 2900 to create the offset between the vent holes and diffuser material, such as a protrusion or recess for example as shown in FIG. 49, or a headgear connector element 2900 with a rear surface with a curvature that is steeper than that of the front surface of the mask frame 2178 so that the headgear connector element 2900 sits away from the front surface of the mask frame 2178.

The diffuser 3000 covers the aperture 2900A in the headgear connector element 2900—this may be a single aperture with a shape corresponding to the area the vent hole arrangement is located. As can best be seen in FIG. 41, this aperture may be divided by dividing structures 2900B to produce several separate apertures or windows 2900A. These dividing structures 2900B increase the stiffness of the headgear connector element 2900 and reduce the amount of bending or flexing that the headgear connector element 2900 may experience. This in effect ensures a more secure attachment of the headgear connector element 2900 to the mask frame, hence the placement of the diffuser 3000 against the vent holes.

Figure 42:
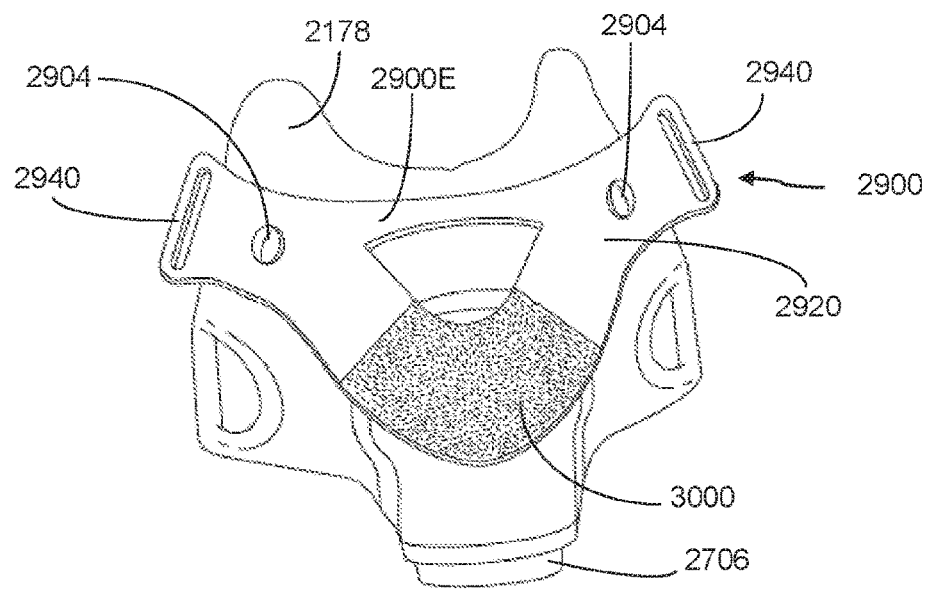
FIG. 42 is a front perspective view of the mask frame of FIGS. 38 to 40 and a further yoke, with diffuser material shown.
Figure 43:
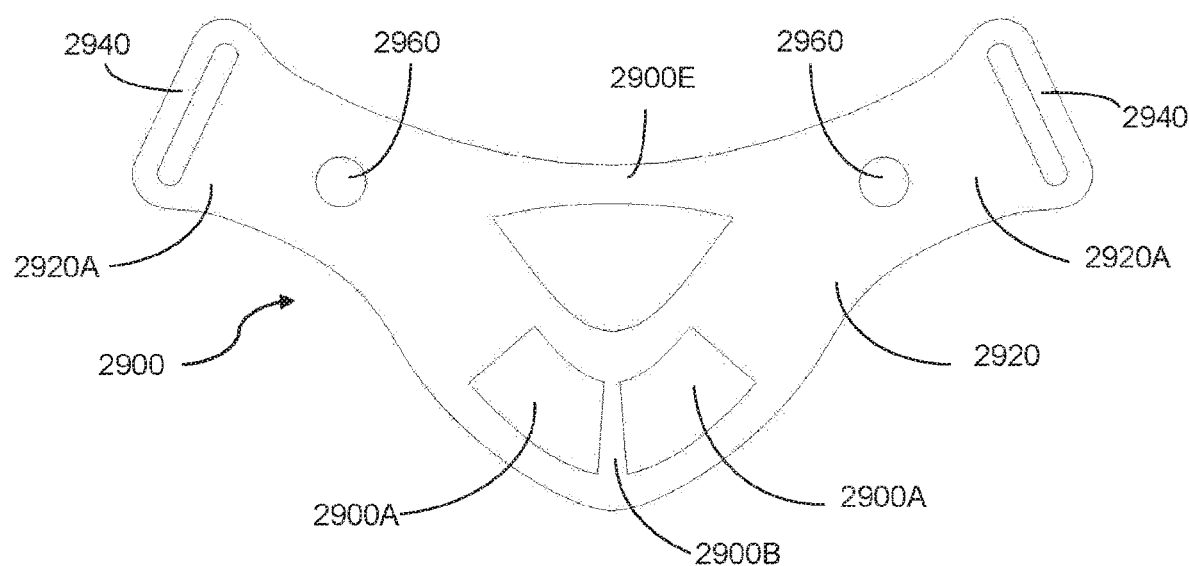
FIG. 43 is a front view of the yoke of FIG. 42.
Figure 44:
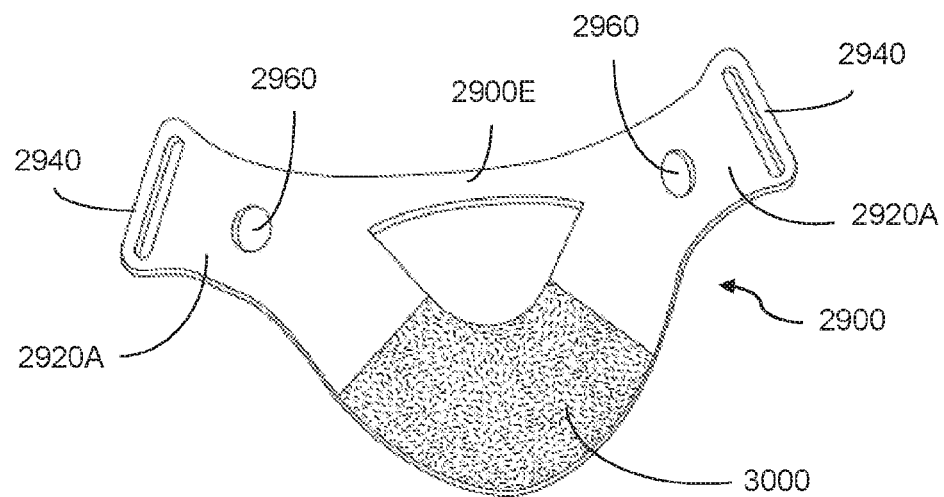
FIG. 44 is a front view of the yoke of FIG. 42 with diffuser material shown.

With reference to FIGS. 42 and 43, an alternative embodiment comprises a headgear connector element 2900 comprising a linkage structure 2900E to provide additional stability and stiffness for the headgear connector element 2900. Linkage structure 2900E comprises a linkage or connection element that connects or extends between left and right lateral strap loops 2940 of the headgear connector element 2900. This structure 2900E maintains a constant distance between the two lateral strap loops 2940 of the headgear connector element 2900, reducing the torsion that the centre of the headgear connector element 2900 experiences that may deform it and push it forward, away from the front surface of the mask frame 2178. This minimises the distance that the headgear connector element 2900 may be pushed away from the vent holes when the headgear connector element 2900 is attached to the mask frame 2178. This reduces the increase in distance between the two structures when the centre of the headgear connector element 2900 is subject to torsion.

The bending of the headgear connector element 2900 occurs when the lateral ends of the headgear connector element 2900 are moved and/or twisted downwards or upwards relative to the mask frame 2178, as per arrows A in FIG. 42. This leads to the upper edge of the headgear connector element 2900 being bent upwards or downwards, respective to the movement of the lateral ends of the headgear connector element 2900. A locating feature 2178A may be provided on the mask frame 2178 or on the headgear connector element 2900 to engage the other of the mask frame 2178 or the headgear connector element 2900, to resist such movement. In this example, with reference to FIG. 42, locating feature 2178A comprises an elevated section or protrusion on the exterior surface of the mask frame 2178, which limits this movement. Locating feature 2178A is complementary to the upper edge of the linkage structure 2900E and limits the upwards movement of the headgear connector element 2900, therefore limiting the excessive bending or flexing of the headgear connector element 2900.

Referring now to FIGS. 45 to 49 a diffuser 3000 is provided on the mask frame 2178, aligned with one or more arrays of bias vent holes 2502 also on the mask frame 2178.

In this example the bias vent 2502 comprises a single array of vent holes extending across the vertical centre line of the mask frame 2178, above the inlet 2706 of the mask frame 2178. The bias vent array extends symmetrically about the vertical centre line in this example.

Diffuser 3000 comprises a diffuser frame 3002 attached to, or forming an integral part of, the mask frame 2178, and positioned to extend around the bias vent array 2502. The diffuser frame 3002 is configured to retain a portion of diffuser material 3004 (not shown in FIGS. 4 and 46). When so retained the diffuser material 3004 covers the holes of the bias vent 2502 to diffuse bias flow through the bias vent 2502.

This embodiment, similar to the embodiment of FIGS. 28 to 44, features vent holes laser drilled or moulded into the centre of the mask frame 2178. The vent hole configuration may be substantially U or V shaped, or arranged in any other suitable shape such as a circle or horizontal, vertical or inclined straight line. The holes are oriented to direct exhaled air away from and reduce draft on the user's face and are positioned within the protruding boss that forms the cushion connector 2708 on the rear of the frame 2178.

This embodiment also features a headgear connector element 2900 to which upper headgear straps are connected. In this example however, the a headgear connector element 2900 does not hold or support the diffuser and does not cover the bias vent 2502.

The diffuser 3000 is instead held by the diffuser frame 3002 which corresponds to the shape of the vent hole array. The walls of the diffuser frame 3002 surround the edges of the diffuser material 3004 and either the rear or front side of the diffuser frame 3002 may feature a lip or rim 3006 which extends inwards, away from the walls, see FIG. 50 in particular. Lip 3006 may act as a support structure for the diffuser 3000 and provide a space between the bias vent 2502 and diffuser material 3004 to prevent condensation from the moist air blocking the vent holes. The diffuser 3000 can be attached to the diffuser frame 3002 by gluing, welding, overmoulding, or any other suitable method and this attachment may be permanent or non-permanent. The former requires the replacement of the diffuser frame 3002 and diffuser material 3004 when the diffuser material 3004 requires replacement, while the latter allows the diffuser material 3004 alone to be easily replaced.

The diffuser frame 3002 itself is secured to the front wall of the mask frame 2718 via clips 3008 on the mask frame 2178. In this example, a pair of laterally opposed clips 3008 are provided, adjacent to the vent hole array of bias vent 2502. Each clip 3008 is located adjacent a respective left and right side margin of the vent hole array, and are laterally spaced from the centre line of the mask frame 2178. The clips 3008 protrude forward from the exterior surface of the front wall of the mask frame 2178. The clips 3008 are configured to engage and mechanically couple with corresponding structures on the left and right walls of the diffuser frame 3002, as can best be seen in FIG. 46. Mechanical coupling between the diffuser frame 3002 and the clips 3008 may be achieved through a simple retention mechanisms such as a snap-fit mechanism whereby the clips 3008 may be barbed and deflect as the diffuser frame 3002 is pressed onto the mask frame 2718, the clips 3008 snapping into engagement with the diffuser frame 3002 when the diffuser frame 3002 is fully pressed onto the mask frame 2718. Alternative embodiments could use a friction fit engagement between the diffuser frame 3002 and clips 3008.

In a variant of this embodiment, the diffuser frame 3002 may be integral with the mask frame 2718 so that these two components comprise a single unit, eliminating the need for clips 3008. In this example, the diffuser material 3004 is removably mounted in the diffuser frame 3002 and may be replaced when required.

With additional reference to FIG. 49, the diffuser frame 3002 may feature gaps or spaces 3002A on the top, bottom or side walls to provide a passage between the mask frame 2178 and the wall of the diffuser frame 3002. These gaps 3002A provide alternative flow paths for exhaled air to flow through. This ensures that air is able to escape the mask with lower resistance than through the diffuser 3000 alone. In this example, the diffuser frame 3002 spaces 3012 the diffuser material 3004 from the surface of the front wall of the mask frame 2178. This allows more CO2 gas (in the exhaled air) to be expelled from the mask during exhalation, or faster washing out of CO2 gas.

Referring now to FIGS. 51 to 60 a mask assembly 2100 is provided comprising a bias vent on the cushion connector structure 2708. As described above, and as can be seen from FIG. 11 for example, the frame 2178 can include a cushion connector 2708 positioned on a rear side of the frame 2178. In some embodiments, the cushion connector 2708 is unitary with the frame 2178 and extends rearwardly from a rear surface 2178A of a front wall 2701 of the frame 2178. The cushion connector 2708 can provide a fluid connection between the inlet 2706 and the cushion module 2150. The cushion connector 2708 can be shaped to fit into at least a portion of the cushion module 2150 to connect the frame 2178 to the cushion module 2150. For example, the cushion connector 2708 can fit into at least a receiving portion of the mask housing 2102, such as a frame connector 2730. In this example the vent holes of bias vent 2502 are not present on the front surface of the mask frame 2178 as with the previous embodiments, but on the cushion connector 2708 that provides a gas flow passage between the inlet structure 2706 of the mask frame 2178 and the cushion module 2150.

As can best be seen in FIG. 51, the cushion connector 2708 comprises a tubular gas flow duct which projects rearwardly from the rear (internal) surface of the mask frame 2178. The gas flow duct, when viewed along its longitudinal axis, can be any shape in transverse cross section, but in this example is trapezoidal but with a continuously curved profile. The gas flow duct comprises an outer surface the side and upper portions of which are provided with vent holes. In this example the vent holes are arranged concentrically around the side and upper portions so that the vent hole array fans out from the centre of the gas flow duct of the cushion connector 2708, away from the central axis 2708A of the cushion connector 2708, illustrated in FIG. 53. The portions provided with vent holes may be equal to about half of the height of the cushion connector structure 2708. The number of vent holes may be around twenty in this example and may be spaced evenly along a single line when the cushion connector 2708 is viewed from the side, as can best be seen in FIG. 52. The vent holes may alternative be arranged in any other shape and/or position of vent array around the cushion connector 2708, but are preferably not located on the lower region of the cushion connector 2708, as the vent holes may be subject to occlusion in this location, leading to noise.

In this example, the vent holes are arranged in a single line around part of the perimeter of the gas flow duct of the cushion connector, at a distance along the length of the cushion connector (i.e. along its central axis 2708A) that is in the space between the rear surface 2178A of the mask frame 2178 and the front surface 2150A of the cushion module 2150 when assembled. This positioning ensures that the vent holes are aligned to lead airflow into the space between the two surfaces 2178A, 2150A. This airflow path, indicated by arrow A in FIG. 50, does not lead to air draft flowing directly onto the user's face due to the contours of the rear surface 2178A of the mask frame 2178 leading the air generally laterally, or at least with a significant lateral component, rather than wholly upwards towards the user's eyes.

The vent holes may be arranged in different arrangements around the a perimeter the cushion connector 2708—such arrangements may include one where vent holes are provided around the entire perimeter of the cushion connector 2708, and one where vent holes are present only on side portions of the cushion connector 2708, that is, there are no vent holes at the top or bottom portions of the cushion connector 2708. Additionally or alternatively, vent holes may be arranged in multiple rows or lines or arrays along all or part of the length of the cushion connector duct.

A annulus or arcuate portion of diffuser material (not shown) may be fitted around the cushion connector 2708 on the exterior perimeter of the cushion connector 2708 to surround and cover all vent holes to diffuse air and reduce noise. The diffuser material may simply be slotted or pushed onto the cushion connector. The diffuser material is sandwiched between the rear surface 2178A of the mask frame 2178 and the front surface 2150A of the cushion module 2150, securing the diffuser material in place when the mask assembly 2100 is assembled.

Referring now to FIGS. 61 to 73, in this example the bias vent 2502 is located on the mask shell housing 2102, generally below the inlet structure 2706. In this example the bias vent 2502 comprises a pair of arrays of vent holes, each array being located below, and to one side of, the inlet aperture 2102A in the mask shell housing 2012 and the valve recess 2726, as described above with reference to FIGS. 25 and 26 for example.

Referring particularly to FIGS. 66 to 70, a diffuser 3000 is provided, for mounting on the mask shell housing 2102, so that diffuser material 3004 of the diffuser 3000 covers the arrays of vent holes to diffuse the gas flow and reduce noise. In this example the diffuser 3000 comprises a diffuser frame 3002 comprising a mounting portion in the form of an upper ring shaped mount 3002A and a pair of lower tabs or wings in the form of laterally positioned diffuser subframes 3002B that are laterally spaced apart so as to each be below and to one side of the ring mount 3002A.

The ring mount 3002A is dimensioned, shaped and configured to be removably mounted on the mask shell housing 2102, with the ring mount 3002A being received in a corresponding ring shaped recess 2102B surrounding the inlet aperture 2102A in the mask shell housing 2102 so that the ring mount 3002A is sandwiched in use between the mask shell housing 2102 and the mask frame 2178, and held in place by the connection between the mask shell housing 2102 and the mask frame 2178.

The diffuser frame 3002 is therefore omega shaped in this embodiment with the size, shape and layout of the ring mount 3002A, and subframes 3002B matching the size, shape and layout of the inlet and vent arrays of the mask shell housing 2102. Thus, when the ring mount 3002A is mounted as described above, the diffuser subframes 3002B are aligned with, and cover the vent arrays. As described above, each diffuser subframe 3002B is provided with a portion of diffuser material 3004 which may be removably or permanently mounted in the subframes 3002B.

The contours of the rear surfaces of the diffuser 3000, and particularly the contours of the diffuser subframes 3002B, are shaped to match the shape and contours of the front surface of the mask shell housing 2102 and in this example are concavely curved so as to match the convex curvature of the front surface of the mask shell housing 2102. The diffuser 3000 and the mask shell housing 2102 thus mate, when the diffuser 3000 is mounted on the mask shell housing 2102.

The ring mount 3002A may be secured in the recess 2012B through frictional fit between the ring mount 3002A and the surrounding surfaces (i.e. inner and outer walls) of the recess 2012B. It may alternatively be held in place between the mask shell housing 2102 and mask frame 2178 when assembled, that is when the cushion connector 2708 of the mask frame 2178 is inserted into the cushion connector structure, and the ring mount 3002A of the diffuser frame 3002 is sandwiched between the mask frame 2178 and mask shell housing 2102. Alternative methods of attachment include snap fit type connection, and other methods of attachment.

The wing like diffuser subframes 3002B are configured to be aligned with, and spaced above, the vent holes when the support component is retained by the housing. The shape and size of the perimeter walls of the subframes 3002B follow that of the vent hole arrays but are slightly larger than this area to avoid blockage of the vent holes. The left and right subframes 3002B are connected by laterally extending linking members 3014 which extend across the diffuser 3000 to form a brace to provide stiffness and stability of the subframes 3002B. The linking members 3014 are located in front of the valve recess 2726 of the mask shell housing 2102 and when the mask frame 2178 and mask shell housing 2012 are assembled, the linking members 3014 are sandwiched between the valve recess 2726 and the inlet 2706 of the mask frame 2178.

The vent arrays each have a generally triangular shape, therefore each subframe 3002B has a corresponding generally triangular shape.

In this example there are two linking members 3014, the first comprising the lower region of the ring mount 3002A and the second being located below the ring section. The second linking member is in-line with (follows the curvature of) and extends between the bottom margin of the subframes 3002B framing the vent holes on each opposing lateral sides of the mask shell housing 2102.

The diffuser 3000 is shaped to avoid occlusion of air flow paths or the inlet 2706 of the mask frame 2178. To achieve this, the linking members 3014 have a concave shape (towards the rear direction), following contours of the exterior surface of the valve recess 2726 of the mask shell housing 2102. This allows the complementary positioning of the mask frame inlet 2706 with reference to the linking members 3014, and therefore also of the mask frame 2178 in relation to the mask shell housing 2102. Complementary positioning refers to the alignment of the rear surface of the mask frame inlet 2706 to the exterior/front surface of the linking member 3014 which in turn follows the contours of the valve recess 2726. This concave section may comprise a solid wall or be formed by multiple linking members as per the illustrated examples.

The bottom region of the subframes 3002B may be in the form of a solid wall. This increases the stiffness of the diffuser 3000, at least partially accounting for the relatively low stiffness of thin or narrow structures such as the linking members 3014 and diffuser frame 3002A and diffuser subframes 3002B.

The linking members 3014 and/or the diffuser frame 3002A and/or the diffuser subframes 3002B may have retention features, such as a snap fit bump and depression combinations, to allow easier assembly and disassembly between the diffuser 3000 and the mask shell housing 2102. The bottom wall of the diffuser 3000 is located beneath the bottom region of the mask shell housing 2102 to "cup" the region below the vent holes, as shown in FIG. 62 and FIG. 74.

The diffuser frame 3002 is constructed of rigid or semi-rigid material as a single-piece construction. It may also be comprised of softer materials such as silicone to enhance the frictional fit attachment of the ring mount 3002A in the recess 2102B of the mask shell housing 2102.

A portion of diffuser material 3004 is attached to each diffuser subframe 3002B. This may be on the front or exterior surface of the subframe 3002B (i.e. on top, as illustrated in FIG. 75). The linking members 3014 and subframes 3002B provide a fixed offset distance between the vent holes and diffuser material 3004. The method of attachment of the diffuser material to the diffuser subframes 3002B may involve any combination of adhesion, slotting into the space defined between the subframe 3002 walls, frictional engagement, overmoulding, clips, for example. The shape of the portions of diffuser material 3004 corresponds to that of the subframes 3002B. The subframes 3002B may also comprise gaps on the top or bottom sides of the subframes 3002B to provide an alternative air passage, maintaining a clear flow path for exhaled air (CO2 washout).

Referring now to FIGS. 74 to 82, in this embodiment, the holes of bias vent 2502 are provided in the recess 2102B that surrounds the mounting aperture 2102A of mask shell housing 2102 of cushion module 2150. As described above aperture 2102A functions as part of the connection between the mask shell housing 2012 and mask frame 2178, and receives cushion connector 2708. A diffuser 3000 in this example comprises a ring of diffuser material 3004 shaped and dimensioned to be received and retained in the recess 2102B.

The diffuser material 3004 has a ring shape that is the same as that of the recess 2102B and is therefore concentric to the aperture 2102A of the mask shell housing 2102. Diffuser 3000 is in this example constructed of a single layer of diffuser material through laser cutting or die cutting.

Vent holes are spaced apart in the recess 2102B concentrically to the aperture 2102A. The diffuser 3000 and vent hole array have the same shape and are concentric with each other. The diffuser 3000 covers all vent holes to diffuse the air flowing out of them. The diffused air then flows through the space between the rear surface 2178A of the mask frame 2178 and the front surface 2102C of the mask shell housing 2102. The vent holes may be evenly spaced around the entire perimeter of the aperture 2102A or have a variable spacing or extend along only a portion of the recess 2102B. The vent flow path can most clearly be seen by arrow A in FIG. 82, and also in FIG. 78.

An example number and spacing of vent holes can be seen in FIG. 75. Any other number and spacing of vent holes is possible.

In FIGS. 74 to 82 the vent holes may be arranged concentrically around the central axis of the aperture 2102A, so that the axis of each vent hole extends generally in the same direction as the axis of aperture 2102A, albeit each vent axis may be inclined to some degree.

Alternatively, the vent holes may be arranged concentrically around and fanning away from the central axis of the aperture 2102A, so that the axis of each vent hole extends generally perpendicularly to the axis of aperture 2102A. In this alternative embodiment, the cushion connector structure 2708 of the mask frame 2178 which is inserted into the aperture 2102A of the mask shell housing 2102 for assembly, also has vent holes to allow air to flow out of the gas flow passage.

The recess 2102B in which the diffuser 3000 is removably mounted may be modified to further diffuse the air and reduce noise. The recess 2102B, when viewed along the axis of aperture 2102A, may be broadened to allow for an increase in diffuser width (hence diffusion area), and sufficient space to install the ring of vent holes, as illustrated in FIGS. 78 and 79. FIGS. 78 and 79 show an enlarged view of the part shown in box A of FIG. 76.

Vent holes located in the recess 2102B may be formed using various techniques such as laser drilling, and/or with various shapes and arrangements. For example, the diameter of the vent holes may not be constant—one or more of the vent holes may have a smaller or larger rear radius than the front radius such that each aperture comprises a bore which tapers along its length, leading to different air flow dynamics and levels of noise. A rear radius which is larger than the front radius may be preferred as the opposite configuration may lead to air turbulence, hence noise, that is the vent cross sectional area increases along its length in the direction of the vent gas flow. The two opposite tapering vent arrangements are shown in FIG. 78. FIG. 78a shows vent holes with a larger hole entry (rear) radius and smaller exit (front) radius while FIG. 78b shows diffuser holes with a smaller rear radius than front radius. Diffuser material 3004 is located at the vent hole outlets.

The vent holes can be further modified such that the longitudinal axis of at least one vent hole is at an angle offset from the central axis of the aperture 2102A. This arrangement is illustrated in FIG. 79. Vent holes which are angled outwardly and/or laterally direct air draft both away from the user's face and also away from objects or people that may be directly in front of the mask. This not only increases the comfort of the user but also those in close vicinity to the user. FIGS. 79a and 79c show two examples in which a radially inner vent wall portion is inclined, whereas FIGS. 79b and 79d show two examples in which a radially outer vent wall is inclined. A further embodiment is envisaged in which both inner and outer vent hole walls are inclined, and/or where the vent is uniformly tapered along its length so that its longitudinal axis is inclined. In these figures, the vertical dotted line represents the central axis of the aperture 2102A (shifted across for clarity) while the diagonal dotted line represents the angle of the vent holes. The arrow A may be taken as an approximation or average of the direction of the resultant vent flow through the vent holes.

Providing vent holes in recess 2102B may necessitate recess 2102B being widened over the recess of say FIG. 24. FIGS. 78, 79a and 79b both show the non-widened recess. FIGS. 78, 79c, and 79d show the widened recess 2102B provided with the vent hole. The widened recess in FIG. 78 is shown in hatched lines. In FIG. 78a, dimension (a) denotes the width of the broadened recess 2102B broadened over the embodiment of FIG. 24 for example, whilst dimension (b) denotes the width of the original recess 2102B of the FIG. 24 example. These vent holes may be drilled in line with the central longitudinal axis of the aperture 2102A.

Changes to the recess 2102B may be implemented with changes to the curvature of the mask shell housing 2102. For example, a wider recess 2102B may require the curvature of the walls of the mask shell housing 2102 adjacent the recess 2102B to be displaced laterally. This wider recess is illustrated in dashed line B of FIG. 84 (the narrower recess is shown by dashed line A). This is because the seal width needs to remain substantially constant in order to seal effectively or sufficiently with a user's face. The depth of the seal housing also cannot easily be reduced or it will contact a user's nose. Therefore the curvature must change to allow for an increased width of recess 2102B. A wider recess 2102B may help to reduce noise as air exiting the vent holes is less likely to hit the side walls of the recess 2102B.

In this embodiment, the diffuser 3000, which need only be the ring of diffuser material 3004 as described above, is contained within the ring shaped recess 2102B of the mask shell housing 2102. The diffuser material 3004 could be arranged to float within that recess 2012B, that is, so as to be able to move between the mask frame 2178 and the rearmost surface of the recess 2012B. However, the diffuser material 3004 and recess 2102B must be together configured to resist any relative movement between the two components that is sufficient for there to be a direct flow path through the recess 2102B and around the diffuser material to atmosphere. Such a direct flow path is undesirable because if exhausted air bypasses the diffuser 3000 then it will not provide the draft and noise damping properties that are desirable.

Further, the diffuser material 3004 and recess 2102B must be further configured to avoid any part of the diffuser material 3004 being squashed or flattened so as to occlude vent flow through the diffuser material 3004. This embodiment therefore provides a diffuser cavity defined between the mask shell housing 2102 and the mask frame 2178, in which the diffuser material snugly fits, where the diffuser material 3004 has a slightly smaller volume than the diffuser cavity. For example, the diffuser 3000 can have a depth that is less that the depth between the rear wall of the recess 2102B and the internal surface of the mask frame 2178. This allows a gap between the vent holes and the diffuser 3000 as shown in FIG. 82, which helps to prevent or minimise condensate filling vent holes. The diffuser 3000 should however, have a depth that is greater than the distance between the front surface of the mask shell housing 2102 and the rear surface of the mask frame 2178, to prevent the formation of a direct flow path as described above. The diffuser 3000 may be able to slide back and forward within the recess 2102B.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes, or tends toward, a particular value, amount, or characteristic. For example, as the context may dictate, the term "generally linear" can mean something that departs from exactly parallel by less than or equal to 15°.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A seal for a respiratory mask comprising:
    an oral sealing portion configured to seal around a user's mouth, and a nasal sealing portion configured to seal on a lower surface of a user's nose and be fully positioned below a bridge of the user's nose, wherein the nasal sealing portion comprises:
    a first upward extension and a second upward extension, wherein each of the first and the second upward extensions has an internal wall configured to engage with a lateral side of the user's nose, and an external wall configured to provide structure to the nasal sealing portion, the internal and external walls being joined along an upper edge of the seal, wherein the external walls comprise:
        a pocket located in each of the first upward extension and the second upward extension and defined by the external wall, the pocket formed by an internal step on an interior surface of the external wall, and having a wall thickness that is less than a thickness of a surrounding portion of the external wall, an outer surface of a region of the external wall containing and immediately surrounding the pocket being smooth and continuous; and
        a thickened rib at least partially defining an upper edge of the pocket and extending along an upper portion of the external wall, wherein the thickened rib is proximate to but spaced from the upper edge of the seal, wherein the thickened rib has a wall thickness that is greater than the wall thickness of the pocket, wherein the thickened rib extends from a rear end of the external wall towards a front end of the seal; and
    suspension members that provide mechanical rigidity and structure to hold a shape of the first and the second upward extensions when the seal is worn by the user, wherein the thickened rib extends from each of a respective one of the suspension members to provide additional support to the seal.

2. The seal of claim 1, wherein the thickened rib narrows at opposed ends.

3. The seal of claim 1, wherein the thickened rib comprises an upper surface and a lower surface, the upper surface having a curved or serpentine shape along its length, and the lower surface having a curved or serpentine shape along its length that follows the shape of the upper surface.

4. The seal of claim 1, wherein the pocket is substantially teardrop shaped.

5. The seal of claim 1, wherein the pocket is located on an interior surface of the external walls.

6. The seal of claim 1, wherein the thickened rib is located on an interior surface of the external walls.

7. The seal of claim 1, wherein the thickened rib has varying thickness along its length.

8. The seal of claim 1, wherein the suspension members provide relatively rigid portions or elements of the seal adjacent or near a relatively thin nasal region.

9. The seal of claim 1, wherein the suspension members comprise thickened regions of a material of the seal.

10. The seal of claim 1, wherein the suspension members have a greater thickness than other portions of the first and the second upward extensions.

11. The seal of claim 1, wherein the suspension members have a thickness equal to a largest thicknesses of the seal.

12. The seal of claim 1, wherein the suspension members extend along an upper edge of the upwardly extending portions or a region or ridge that joins to nasal sealing surfaces of the internal wall along the upper edges of the upwardly extending portions.

13. The seal of claim 1, wherein the suspension members are sized and/or shaped and/or otherwise configured to transfer force from a rearward or user-contacting surface of the first and the second upward extensions toward or to a forward surface of the first and the second upward extensions.

14. The seal of claim 1, wherein the suspension members are sized and/or shaped and/or otherwise configured to transfer force from a rearward surface of the first and the second upward extensions toward or to another support portion of the seal, or any other components of the respiratory mask.

15. The seal of claim 1, wherein the suspension members provide support to a nasal region on the nasal sealing portion.

* * * * *